US012582309B2

(12) United States Patent
Hirohara

(10) Patent No.: US 12,582,309 B2
(45) Date of Patent: Mar. 24, 2026

(54) OPHTHALMIC APPARATUS

(71) Applicant: Topcon Corporation, Tokyo (JP)

(72) Inventor: Yoko Hirohara, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 497 days.

(21) Appl. No.: 18/091,382

(22) Filed: Dec. 30, 2022

(65) Prior Publication Data

US 2023/0218161 A1     Jul. 13, 2023

(30) Foreign Application Priority Data

Jan. 11, 2022     (JP) ................................. 2022-002356

(51) Int. Cl.
　　A61B 3/10　　　　(2006.01)
　　A61B 3/00　　　　(2006.01)
(52) U.S. Cl.
　　CPC ............ A61B 3/102 (2013.01); A61B 3/0091 (2013.01)
(58) Field of Classification Search
　　CPC ..... A61B 3/102; A61B 3/0091; A61B 3/1005; A61B 3/0008; A61B 3/12; A61B 3/14
　　USPC ........................................................ 351/206
　　See application file for complete search history.

(56) References Cited

U.S. PATENT DOCUMENTS

| | | | |
|---|---|---|---|
| 5,483,305 A | 1/1996 | Kohayakawa | |
| 5,777,718 A | 7/1998 | Kohayakawa | |
| 8,506,079 B2 | 8/2013 | Martinez et al. | |
| 11,191,431 B2 * | 12/2021 | Shimizu | ................. A61B 3/152 |

| | | | |
|---|---|---|---|
| 2009/0244485 A1 | 10/2009 | Walsh et al. | |
| 2010/0110377 A1 | 5/2010 | Maloca et al. | |
| 2011/0299034 A1 | 12/2011 | Walsh et al. | |

(Continued)

FOREIGN PATENT DOCUMENTS

| | | |
|---|---|---|
| CN | 110811536 A | 2/2020 |
| EP | 3075303 A1 | 10/2016 |

(Continued)

OTHER PUBLICATIONS

Extended European search report issued on May 25, 2023, in corresponding European patent Application No. 23150138.8, 8 pages.
Chinese Office Action issued Jul. 19, 2025, in corresponding Chinese Application No. 202310038138.X (with Machine Translation by Global Dossier), 18pp.

(Continued)

*Primary Examiner* — Mohammed A Hasan
(74) *Attorney, Agent, or Firm* — XSENSUS LLP

(57) ABSTRACT

An ophthalmic apparatus includes an objective lens, and an OCT optical system optical system is configured to project a measurement light onto a subject's left or right eye via an objective lens, and to detect interference light between returning light of the measurement light a reference light having traveled through a reference optical path. An optical axis switching member switches an optical axis of the OCT optical system to approximately coincide with a first or second measurement optical axis. A controller is configured to control the optical axis switching member. An intraocular parameter calculator calculates an intraocular parameter of the subject's left or right eye based on a detection result of the interference light acquired in a state where the optical axis of the OCT optical system is switched so that the optical axis of the OCT optical system approximately coincides with the first or second measurement optical axis.

18 Claims, 19 Drawing Sheets

(56) References Cited

U.S. PATENT DOCUMENTS

| | | | |
|---|---|---|---|
| 2012/0320338 A1 | 12/2012 | Hirose et al. | |
| 2013/0201449 A1 | 8/2013 | Walsh et al. | |
| 2015/0085252 A1 | 3/2015 | Fujimura et al. | |
| 2015/0085253 A1 | 3/2015 | Walsh et al. | |
| 2015/0109578 A1 | 4/2015 | Baranton et al. | |
| 2015/0138503 A1 | 5/2015 | Walsh et al. | |
| 2015/0208916 A1 | 7/2015 | Hayashi | |
| 2016/0345822 A1 | 12/2016 | Fujimura et al. | |
| 2017/0049318 A1 | 2/2017 | Walsh et al. | |
| 2017/0119247 A1 | 5/2017 | Walsh et al. | |
| 2017/0347872 A1* | 12/2017 | Ozaki | A61B 3/0083 |
| 2019/0090733 A1 | 3/2019 | Walsh et al. | |
| 2019/0183333 A1* | 6/2019 | Arieli | A61B 3/1005 |
| 2020/0046220 A1 | 2/2020 | Tatara | |
| 2020/0085292 A1 | 3/2020 | Fukuma et al. | |
| 2020/0226755 A1* | 7/2020 | Shimozato | G06T 7/0012 |
| 2021/0068651 A1* | 3/2021 | Yasuno | G01B 9/02091 |
| 2021/0076927 A1* | 3/2021 | Kobayashi | A61B 3/165 |
| 2021/0386285 A1 | 12/2021 | Walsh et al. | |
| 2021/0401286 A1 | 12/2021 | Walsh et al. | |
| 2022/0117486 A1* | 4/2022 | Yoshida | A61B 3/152 |
| 2022/0142475 A1* | 5/2022 | Hashimoto | A61B 3/0025 |
| 2023/0172447 A1 | 6/2023 | Walsh et al. | |
| 2024/0315551 A1 | 9/2024 | Walsh et al. | |
| 2025/0143569 A1 | 5/2025 | Walsh et al. | |

FOREIGN PATENT DOCUMENTS

| | | | | |
|---|---|---|---|---|
| EP | 3222204 A1 | 9/2017 | | |
| EP | 3884845 A1 | 9/2021 | | |
| JP | 6-304139 A | 11/1994 | | |
| JP | 2013-248376 A | 12/2013 | | |
| JP | 2014094313 A | 5/2014 | | |
| JP | 2015502234 A | 1/2015 | | |
| JP | 2016-187461 A | 11/2016 | | |
| JP | 6367563 B2 * | 8/2018 | ............. | A61B 3/152 |
| JP | 2019-62939 A | 4/2019 | | |
| JP | 2019171130 A | 10/2019 | | |
| JP | 2019208750 A | 12/2019 | | |
| JP | 6641730 B2 * | 2/2020 | | |
| JP | 2020-44027 A | 3/2020 | | |
| JP | 2020036717 A | 3/2020 | | |
| JP | 2020151094 A | 9/2020 | | |
| JP | 2021087874 A | 6/2021 | | |

OTHER PUBLICATIONS

Japanese Office Action issued Aug. 19, 2025, in corresponding Japanese Application No. 2022-002356 {with Machine Translation by Global Dossier), 12pp.

Office Action issued Jan. 13, 2026, in corresponding Japanese Patent Application No. 2022-002356, 8pp.

* cited by examiner

OPHTHALMIC APPARATUS

CROSS-REFERENCE TO RELATED APPLICATION

This application is based upon and claims the benefit of priority from Japanese Patent Application No. 2022-002356, filed Jan. 11, 2022; the entire contents of which are incorporated herein by reference.

FIELD

The disclose relates to an ophthalmic apparatus.

BACKGROUND

Ophthalmic apparatuses capable of performing a plurality of inspections and measurements for a subject's eye are known. The inspections and the measurements for the subject's eye include a subjective inspection and an objective measurement. The subjective inspection is to acquire the result based on the responses from the subject. The objective measurement is to acquire information on the subject's eye mainly by the use of a physical method without referring to the responses from the subject.

For example, Japanese Unexamined Patent Application Publication No. 2016-187461 discloses an ophthalmic apparatus capable of performing the subjective inspection and the objective measurement. In this ophthalmic apparatus, a refractive power measurement of the subject's eye, a keratometry of the subject's eye, photographing using optical coherence tomography, and a measurement using optical coherence tomography can be performed. This ophthalmic apparatus includes a common optical system for the left and right eye, and this optical system can be used to perform the subjective inspection and the objective measurement on one of the left and right eyes.

Further, for example, Japanese Unexamined Patent Application Publication No. 63-304139 discloses an ophthalmic apparatus capable of performing refractive power measurement on one of the left and right eyes using a single optical system while presenting a fixation target independently for each of the left and right eyes.

In contrast, for example, Japanese Unexamined Patent Application Publication No. 2019-062939 discloses an ophthalmic apparatus with two optical systems provided independently for the left and right eyes, and capable of simultaneously performing refractive power measurement and the keratometry for the left and right eyes using the two optical systems.

In addition, for example, U.S. Pat. No. 8,506,079 discloses an ophthalmic apparatus capable of simultaneously acquiring Hartmann images of the left and right eyes, and simultaneously measuring the wavefront aberration of the left and right eyes.

SUMMARY

One aspect of the embodiments is an ophthalmic apparatus, including: an objective lens; an OCT optical system configured to split light from a light source into measurement light and reference light, to project the measurement light onto a subject's left eye or a subject's right eye via the objective lens, the subject's left eye being arranged on a first measurement optical axis, the subject's right eye being arranged on a second measurement optical axis, and to detect interference light between returning light of the measurement light from the subject's left eye or the subject's right eye and the reference light having traveled through a reference optical path; an optical axis switching member configured to switch an optical axis of the OCT optical system so that the optical axis of the OCT optical system approximately coincides with any one of the first measurement optical axis and the second measurement optical axis; a controller configured to control the optical axis switching member; and an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis.

DETAILED DESCRIPTION

Figure 1:
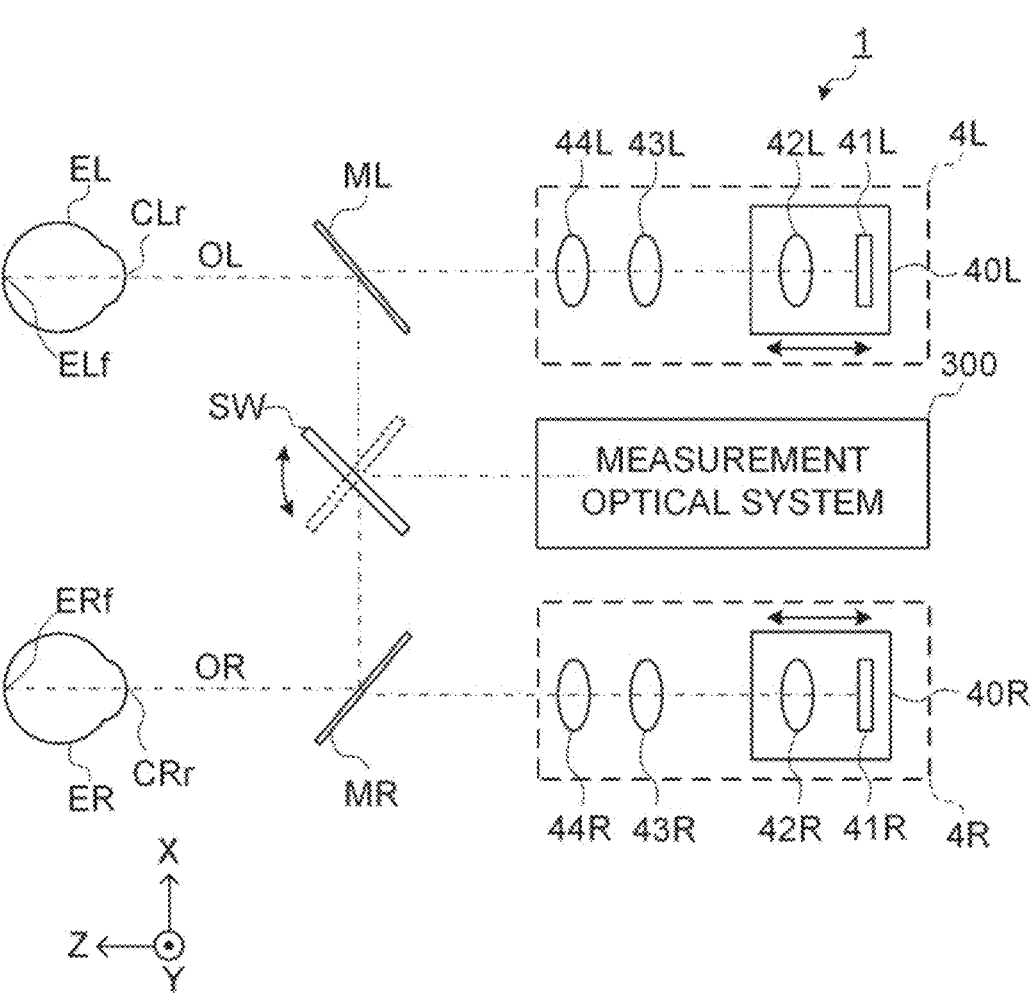
FIG. 1 is a schematic diagram illustrating an example of a configuration of an optical system of an ophthalmic apparatus according to a first embodiment.

The configurations disclosed in Japanese Unexamined Patent Application Publication No. 2016-187461 and Japanese Unexamined Patent No. 06-304193 are configurations for measuring one of the left and right eyes at a time. Thereby, they cannot measure the characteristics of both eyes with both eyes open. In contrast, the configuration disclosed in Japanese Unexamined Patent Application Publication No. 2019-062939 can simultaneously measure both eyes with both eyes open. However, it leads to larger apparatus and higher costs. In addition, the configuration disclosed in U.S. Pat. No. 8,506,079 may cause the apparatus to become larger when performing measurements other than wavefront aberration measurement, or may cause a decrease in measurement accuracy due to the inability to measure under suitable conditions when performing measurements other than wavefront aberration measurement.

According to some embodiments of the present invention, a new technique capable of measuring characteristics of both eyes with high precision and space saved at low cost can be provided.

Referring now to the drawings, exemplary embodiments of an ophthalmic apparatus according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic apparatus according to embodiments can sequentially perform predetermined inspection and/or measurement on both eyes with both eyes open while sharing an objective lens with a plurality of optical systems for performing the plurality of measurements with different measurement types. In particular, the ophthalmic apparatus according to the embodiments can sequentially perform OCT measurement on both eyes using a single OCT optical system and can calculate intraocular parameter(s) for each of both eyes. By sharing the objective lens and the OCT optical system for OCT measurement of both eyes, it is possible to reduce the size and cost of the apparatus.

In some embodiments, the ophthalmic apparatus further includes at least one of an objective measurement optical system for performing objective measurement different from OCT measurement or a subjective inspection optical system for performing subjective inspection. In such ophthalmic apparatuses, by sharing the objective lens with a plurality of optical systems corresponding to the type of inspections and measurements, the apparatus can be reduced the size and the cost.

The objective measurement is a method for measurement to acquire information on a subject's eye mainly by the use of a physical method without referring to the responses from the subject. The objective measurements include a measurement for acquiring the characteristics of the subject's eye and a photographing for acquiring an image of the subject's eye. Examples of the other objective measurements include a tonometry, a fundus photography, and the like. In some embodiments, the ophthalmic apparatus is capable of performing refractive power measurement (refractometry) and OCT measurement as the objective measurement. In some embodiments, the ophthalmic apparatus is capable of performing refractive power measurement, keratometry, and OCT measurement as the objective measurement.

In the following, a case where the ophthalmic apparatus according to the embodiments perform OCT on an anterior segment or a fundus will be described. Hereinafter, in the present embodiment, the case of using the spectral domain type OCT method will be described. However, the configuration according to the embodiments can also be applied to an ophthalmic apparatus using other type of OCT (for example, swept source type OCT or time domain OCT).

The subjective inspection is a method for measurement to acquire information using the responses from the subject. Examples of the subjective inspection include a visual field test, and a subjective refractometry such as a far vision test, a near vision test, a contrast test, a glare test or the like.

Hereinafter, a fundus conjugate position is a position substantially conjugate optically to a fundus of the subject's eye in a state where alignment is completed, and means a position conjugate optically to the fundus of the subject's eye or the vicinity of the position. Similarly, a pupil conjugate position is a position substantially conjugate optically to a pupil of the subject's eye in a state where alignment is completed, and means a position conjugate optically to the pupil of the subject's eye or the vicinity of the position.

Further, in the following embodiments, a horizontal direction (i.e., left/right direction) orthogonal to an optical axis of the optical system is regarded as the X direction, a vertical direction (i.e., up/down direction) orthogonal to the optical axis of the optical system is regarded as the Y direction, and the optical axis direction (i.e., front/back direction) of the optical system is regarded as the Z direction.

First Embodiment

<Configuration of Optical System>

Figure 2:
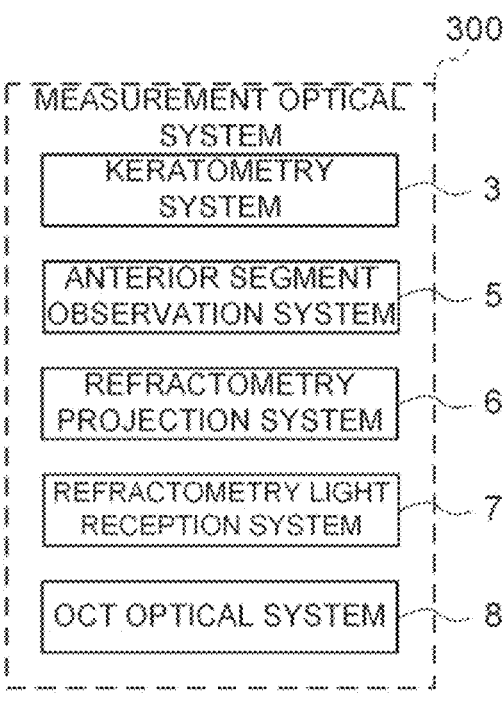
FIG. 2 is a schematic diagram illustrating an example of a configuration of the optical system of the ophthalmic apparatus according to the first embodiment.

FIGS. 1 and 2 illustrate examples of a configuration of an optical system of an ophthalmic apparatus according to a first embodiment. FIG. 1 schematically shows the configuration of the optical system of the ophthalmic apparatus according to the first embodiment when viewed from the upper side. FIG. 2 shows a functional block diagram representing an example of the configuration of a measurement optical system 300 in FIG. 1.

The ophthalmic apparatus 1 according to the first embodiment includes the measurement optical system 300, dichroic mirrors ML and MR, an optical axis switching member SW, a fixation projection system 4L, and a fixation projection system 4R. The measurement optical system 300 may include the dichroic mirrors ML and MR, the optical axis switching member SW, the fixation projection system 4L, and the fixation projection system 4R.

(Measurement Optical System 300)

The measurement optical system 300 includes an objective lens (not shown), and an optical system for measuring a subject's left eye EL and a subject's right eye ER via the objective lens. The subject's left eye EL is a left eye of the subject. The subject's right eye ER is a right eye of the subject. In measuring using the optical system described above, a measurement optical axis that has been adjusted so as to coincide with the optical axis of the measurement optical system 300 (optical axis of an OCT optical system 8) among the measurement optical axes OL and OR which are positioned at a distance from each other, passes through the objective lens. The subject's left eye EL is arranged on the measurement optical axis OL. The subject's right eye ER is arranged on the measurement optical axis OR.

As shown in FIG. 2, the measurement optical system 300 includes a keratometry system 3, an anterior segment observation system 5, a refractometry projection system 6, a refractometry light reception system 7, and the OCT optical system 8, in addition to the objective lens described above.

The keratometry system 3 is an optical system for measuring information representing the shape of a cornea CLr of the subject's left eye EL and information representing the shape of a cornea CRr of the subject's right eye ER. The keratometry system 3 is configured to project light for measuring corneal shape onto the subject's eye to be measured without going through the objective lens described above, and to receive returning light of the light for measuring corneal shape.

The anterior segment observation system 5 is configured to illuminate any one of an anterior segment of the subject's left eye and an anterior segment of the subject's right eye with illumination light, and to receive retuning light of the illumination light via the objective lens.

The refractometry projection system 6 projects light for refractometry onto any one of the subject's left eye EL and subject's right eye ER via the objective lens to project a measurement pattern (ring pattern) centered on the measurement optical axis OL or the measurement optical axis OR onto a fundus ELf or a fundus ERf.

The refractometry light reception system 7 is configured to receive returning light from the fundus ELf or the fundus ERf, via the objective lens.

The OCT optical system 8 is configured to split light from an OCT light source into reference light and measurement light, to project the measurement light onto any one of the subject's left eye EL positioned on the measurement optical axis OL or the subject's right eye ER positioned on the measurement optical axis OR via the objective lens, and detects interference light between returning light of the measurement light from the subject's left eye EL or the subject's right eye ER and the reference light traveling through a reference optical path.

(Dichroic Mirrors ML and MR)

Each of the dichroic mirrors ML and MR transmits light with wavelength components in the visible region, and reflects light with wavelength components in the near-infrared (or infrared) region. Here, the fixation light flux projected by the fixation projection systems 4L and 4R has a wavelength component in the visible region, and the light projected by the measurement optical system 300 has wavelength components in the near-infrared (or infrared) region.

The dichroic mirrors ML is arranged on the measurement optical axis OL. The dichroic mirror ML transmits a fixation light flux from the fixation projection system 4L, and guides it to the subject's left eye EL. Further, the dichroic mirror ML reflects light from the measurement optical system 300 toward the subject's left eye EL, and reflects returning light from the subject's left eye EL toward the measurement optical system 300. Similarly, the dichroic mirror MR is arranged on the measurement optical axis OR. The dichroic mirror MR transmits a fixation light flux from the fixation projection system 4R, and guides it to the subject's right eye ER. Further, the dichroic mirror MR reflects light from the measurement optical system 300 toward the subject's right eye ER, and reflects returning light from the subject's right eye ER toward the measurement optical system 300.

(Optical Axis Switching Member SW)

The optical axis switching member SW is positioned between the measurement optical system 300 and the dichroic mirrors ML and MR. The optical axis switching member SW is configured to guide the optical axis of the measurement optical system 300 (i.e., light from or to the measurement optical system 300) to any one of the dichroic mirror ML and the dichroic mirror MR.

In some embodiments, the optical axis switching member SW deflects the optical axis of the measurement optical system 300. For example, the optical axis switching member SW has one or more deflection surfaces that can change the deflection direction of the optical axis. In this case, the optical axis switching member SW guides the optical axis of the measurement optical system 300 to the dichroic mirror ML when an orientation of the deflection surface is in a first deflection direction, and guides the optical axis of the measurement optical system 300 to the dichroic mirror MR when the orientation of the deflection surface is in a second deflection direction. For example, the optical axis switching member SW has two or more deflection surfaces whose normal directions are different from each other, and is configured to be rotatable around a rotary axis extending in the Y axis direction. In FIG. 1, the optical axis switching member SW includes a switching mirror having two or more deflection surfaces formed on both sides and configured to be rotatable centered on the rotary axis extending in the Y axis direction. By rotating such the optical axis switching member SW centered on the rotary axis, the deflection direction of the optical axis of the measurement optical system 300 can be switched.

In some embodiments, the optical axis switching member SW is configured to be capable of inserting into or removing from the optical axis of the measurement optical system 300. For example, the optical axis switching member SW guides the optical axis of the measurement optical system 300 to one of the dichroic mirrors ML and MR when the optical axis switching member SW is positioned on the optical axis of the measurement optical system 300, and guides the optical axis of the measurement optical system 300 to another of the dichroic mirrors ML and MR when the optical axis switching member SW is removed from the optical axis of the measurement optical system 300.

In some embodiments, the optical axis switching member SW has the deflection surface that deflects the optical axis of the measurement optical system 300, and is configured to be capable of moving along the optical axis of the measurement optical system 300. For example, the optical axis switching member SW deflects the optical axis of the measurement optical system 300 to guide it to one of the dichroic mirrors ML and MR when the optical axis switching member SW is positioned at a first deflection position on the optical axis of the measurement optical system 300, and deflects the optical axis of the measurement optical system 300 to guide it to another of the dichroic mirrors ML and MR when the optical axis switching member SW is positioned at a second deflection position on the optical axis of the measurement optical system 300.

In some embodiments, the optical axis switching member SW switches the optical axis of the measurement optical system 300 at high speed so as to alternately approximately coincide with the measurement optical axis OL and the measurement optical axis OR. In other words, the optical axis switching member SW may switch the optical axis of the measurement optical system 300 at high speed so as to substantially simultaneously project light from the measurement optical system 300 onto both eyes. For example, the optical axis switching member SW can at least project the light from the measurement optical system 300 on one of both eyes, and can switch the optical axis of the measurement optical system 300 to another of both eyes by providing time to receive returning light of the light.

In the following, for convenience of explanation, the optical axis switching member SW is assumed to have two deflection surfaces formed on both sides and to guide the optical axis of the measurement optical system 300 to any one of the dichroic mirrors ML and MR by changing the orientation of the deflection surfaces through rotation centered on the rotary axis.

(Fixation Projection Systems 4L and 4R)

The fixation projection system 4L presents fixation target(s) to the subject's left eye EL by projecting the fixation light flux onto the fundus ELf of the subject's left eye EL. The fixation projection system 4L includes a fixation unit 40L and relay lenses 43L and 44L. The fixation unit 40L includes a liquid crystal panel 41L and a relay lens 42L. The liquid crystal panel 41L displays a pattern representing a fixation target under the control from a controller described below. By changing the display position of the fixation target on the screen of the liquid crystal panel 41L, the fixation position of the subject's left eye EL can be changed. Further, the fixation unit 40L is movable along an optical axis under the control from the controller described below.

Light from the liquid crystal panel 41L passes through the relay lenses 42L, 43L, and 44L, is transmitted through the dichroic mirror ML, and is projected onto the fundus ELf. In some embodiments, the fixation unit 40L can be moved in the optical axis direction independently of the relay lenses 43L and 44L.

Similarly, the fixation projection system 4R presents fixation target(s) to the subject's right eye ER by projecting the fixation light flux onto the fundus ERf of the subject's right eye ER. The fixation projection system 4R includes a fixation unit 40R and relay lenses 43R and 44R. The fixation unit 40R includes a liquid crystal panel 41R and a relay lens 42R. The liquid crystal panel 41R displays a pattern representing a fixation target under the control from the controller described below. By changing the display position of the fixation target on the screen of the liquid crystal panel 41R, the fixation position of the subject's right eye ER can be changed. Further, the fixation unit 40R is movable along an optical axis under the control from the controller described below.

Light from the liquid crystal panel 41R passes through the relay lenses 42R, 43R, and 44R, is transmitted through the dichroic mirror MR, and is projected onto the fundus ERf. In some embodiments, the fixation unit 40R can be moved in the optical axis direction independently of the relay lenses 43R and 44R.

The fixation unit 40L can be moved in the optical axis direction independently of the fixation unit 40R. In other words, the fixation units 40L and 40R can be independently moved in the optical axis direction in accordance with the respective refractive powers of the subject's left eye EL and the subject's right eye ER.

Examples of the fixation position of each of the subject's left eye EL and the subject's right eye ER include a position for acquiring an image centered at a macular region of the fundus, a position for acquiring an image centered at an optic disc, and a position for acquiring an image centered at the fundus center between the macular region and the optic disc. The display position of the pattern representing the fixation target can be arbitrarily changed.

The ophthalmic apparatus 1 can perform keratometry, refractometry, and OCT measurement on the subject's left eye EL using the measurement optical system 300 in a state where the fixation target is presented to the subject's left eye EL by the fixation projection system 4L. Further, the ophthalmic apparatus 1 can perform keratometry, refractometry, and OCT measurement on the subject's right eye ER using the measurement optical system 300 in a state where the fixation target is presented to the subject's right eye ER by the fixation projection system 4R. In some embodiments, the ophthalmic apparatus 1 sequentially performs at least one of keratometry, refractometry, or OCT measurement on the subject's left eye EL and the subject's right eye ER using the measurement optical system 300, in a state where the fixation targets are presented to the subject's left eye EL and the subject's right eye ER, respectively by the fixation projection systems 4L and 4R.

Such the ophthalmic apparatus 1 includes an optical axis adjusting unit configured to adjust an optical axis (axis of the optical path of measurement light) of the OCT optical system 8. The optical axis adjusting unit can deflect the measurement light or move the optical axis of the OCT optical system 8, by controlling optical element(s) on the path of the measurement light under the control from the controller described below. The controller is configured to control the optical axis adjusting unit so that the optical axis of the OCT optical system 8 approximately coincides with any one of the measurement optical axes OL and OR.

Further, the ophthalmic apparatus 1 includes a pupillary distance adjusting unit configured to change a distance in the X direction between the measurement optical axes OL and OR in accordance with a pupillary distance of the subject.

Figure 3:
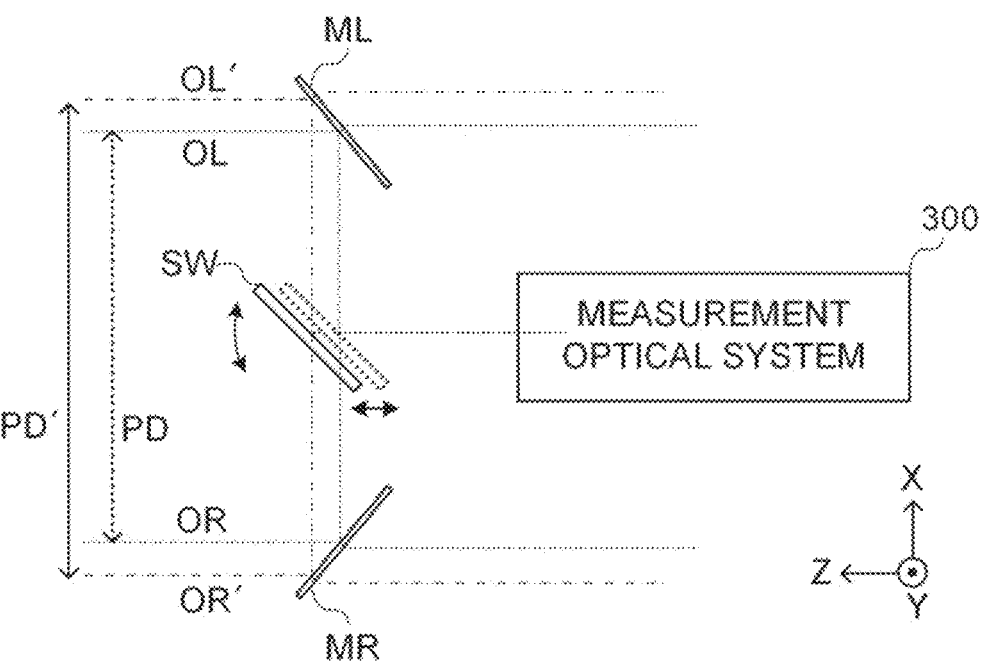
FIG. 3 is a schematic diagram for explaining the optical system of the ophthalmic apparatus according to the first embodiment.

FIG. 3 shows a diagram describing an example of the operation of the pupillary distance adjusting unit in the ophthalmic apparatus 1 according to the first embodiment. In FIG. 3, like reference numerals designate like parts as in FIG. 1, and the redundant explanation may be omitted as appropriate.

The pupillary distance adjusting unit changes the distance in the X direction between the measurement optical axes OL and OR, by moving the optical axis switching member SW along the measurement optical axis OL or the measurement optical axis OR (Z direction, optical axis of the measurement optical system 300). For example, when the optical axis switching member SW is in the initial position, the distance in the X direction between the measurement optical axes OL and OR is the pupillary distance PD. Here, while maintaining the deflection surface of the optical axis switching member SW constant, the optical axis switching member SW is moved along the measurement optical axis OL or the measurement optical axis OR from the initial position. As shown in FIG. 3, this changes positions of the optical axes deflected by the dichroic mirrors ML and MR, the measurement optical axis OL becomes the measurement optical axis OL', and the measurement optical axis OR becomes the measurement optical axis OR'. As a result, the distance in the X direction between the measurement optical axes OL' and OR' becomes the pupillary distance PD'. That is, the pupillary distance is changed.

In some embodiments, the pupillary distance is changed by moving the optical axis switching member SW in the X direction shown in FIG. 3.

In some embodiments, the optical axis adjusting unit moves the optical axis switching member SW along the measurement optical axis OL or the measurement optical axis OR so that the optical axis of the OCT optical system 8 approximately coincides with any one of the measurement optical axes OL and OR.

In some embodiments, the optical axis switching member SW is moved by a movement mechanism (not shown) under the control from the controller described below. In this case, the function of the pupillary distance adjusting unit is realized by the movement mechanism (not shown) (and the controller). In some embodiments, the optical axis switching member SW is manually moved by the movement mechanism not shown in the figure. In this case, the function of the pupillary distance adjusting unit is realized by the movement mechanism not shown in the figure.

In addition, the ophthalmic apparatus 1 includes an angle of convergence adjusting unit configured to change at least one of an orientation of the measurement optical axis OL or an orientation of the measurement optical axis OR in accordance with an angle of convergence of the subject. Here, the measurement optical axis OL enters the subject's left eye EL through its pupil, and the measurement optical axis OR enters the subject's right eye ER through its pupil.

Figure 4:
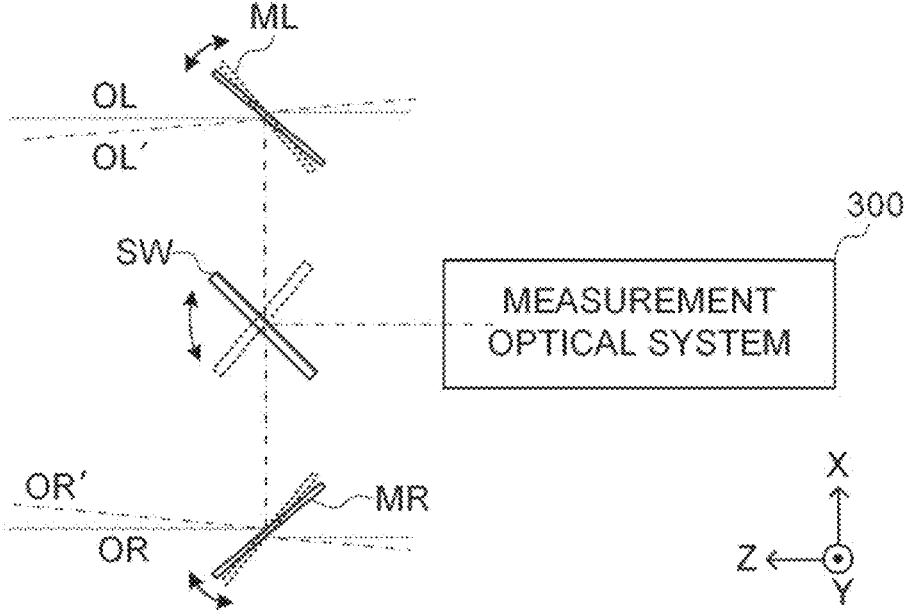
FIG. 4 is a schematic diagram for explaining the optical system of the ophthalmic apparatus according to the first embodiment.

FIG. 4 shows a diagram describing an example of the operation of the angle of convergence adjusting unit in the ophthalmic apparatus 1 according to the first embodiment. In FIG. 4, like reference numerals designate like parts as in FIG. 1, and the redundant explanation may be omitted as appropriate.

The angle of convergence adjusting unit changes at least one of orientations of the measurement optical axis OL or the measurement optical axis OR, by changing at least one of an orientation of the dichroic mirror ML or an orientation of the dichroic mirror MR. Here, the orientation of the dichroic mirror ML corresponds to an orientation (normal direction) of an optical path coupling plane of an optical path coupling member that couples an optical path (optical axis) of the measurement optical system 300 with an optical path (optical axis) of the fixation projection system 4L. Further, the orientation of the dichroic mirror MR corresponds to an orientation of an optical path coupling plane of an optical path coupling member that couples an optical path of the measurement optical system 300 with an optical path of the fixation projection system 4R.

For example, the optical path coupling plane (deflection surface) of the dichroic mirror ML is configured to be rotatable around a rotary axis extending in the Y axis direction. For example, the optical path coupling plane (deflection surface) of the dichroic mirror MR is configured to be rotatable around a rotary axis extending in the Y axis direction.

For example, when the orientation of the deflection surface of the dichroic mirror ML is in a first direction and the orientation of the deflection surface of the dichroic mirror MR is in a second direction, the respective orientations of the measurement optical axes OL and OR are approximately parallel to the optical axis direction of the measurement optical system 300. Here, the orientation of the deflection surfaces of each of the dichroic mirrors ML and MR is changed inward. Thereby, as shown in FIG. 4, the measurement optical axis OL deflected by the dichroic mirror ML becomes the measurement optical axis OL', and the measurement optical axis OR becomes the measurement optical axis OR'. That is, the angle of convergence is changed.

In some embodiments, the dichroic mirrors ML and MR are rotated by a movement mechanism (rotary mechanism) not shown in the figure, under the control from the controller described below. In this case, the function of the angle of convergence adjusting unit is realized by the movement mechanism not shown in the figure (and the controller). In some embodiments, the dichroic mirrors ML and MR are manually rotated by the movement mechanism (rotary mechanism) not shown in the figure. In this case, the function of the angle of convergence adjusting unit is realized by the movement mechanism not shown in the figure.

Further, the angle of convergence adjusting unit may change at least one of the orientations of the measurement optical axes OL and OR by adjusting a deflection angle of the deflection surface by the optical axis switching member SW. For example, by adjusting the deflection angle of the deflection surface(s) by the optical axis switching member SW, an incident direction of the optical axis of the measurement optical system 300 on the deflection surfaces of the dichroic mirrors ML and MR can be changed. As a result, the angle of convergence is changed.

In some embodiments, the ophthalmic apparatus 1 includes a height adjusting unit configured to change the orientation (deflection direction) of the deflection surface of the optical axis switching member SW, the orientation of the deflection surface (optical path coupling plane) of the dichroic mirror ML, and/or the orientation of the deflection surface of the dichroic mirror MR. This allows to adjust the arrangement direction of the measurement optical axes OL and OR. For example, when an arrangement direction (alignment direction) of the subject's left eye EL and the subject's right eye ER is not in the horizontal direction (X direction), the height adjusting unit described above allows the arrangement direction of the measurement optical axes OL and OR to be matched to the arrangement direction of the subject's left eye EL and subject's right eye ER. The movement mechanism for rotating the deflection surface of the optical axis switching member SW, the deflection surface (optical path coupling plane) of the dichroic mirror ML, and the deflection surface of the dichroic mirror MR is an example of the height adjusting unit.

Further, the ophthalmic apparatus 1 includes an arithmetic processor configured to calculate intraocular parameter(s) of the subject's eye based on a detection result of interference light acquired by the OCT optical system 8. Specifically, the arithmetic processor is configured to calculate an intraocular parameter of the subject's left eye EL based on a detection result of the interference light acquired in a state where the optical axis of the OCT optical system 8 is approximately coincides with the measurement optical axis OL, and to calculate an intraocular parameter of the subject's right eye ER based on a detection result of the interference light acquired in a state where the optical axis of the OCT optical system 8 is approximately coincides with the measurement optical axis OR.

The fixation projection system 4L is an example of the "first fixation optical system" according to the embodiments. The fixation projection system 4R is an example of the "second fixation optical system" according to the embodiments. The dichroic mirror ML is an example of the "first optical path coupling member" according to the embodiments. The dichroic mirror MR is an example of the "second optical path coupling member" according to the embodiments. The optical axis switching member SW (or optical axis switching member SW and the movement mechanism for rotating the optical axis switching member SW) is an example of the "optical axis switching member" according to the embodiments. The movement mechanism for rotating the dichroic mirrors ML and MR is an example of the angle of convergence adjusting unit. The angle of convergence adjusting unit is an example of the "first adjustment unit" according to the embodiments. The movement mechanism for rotating the deflection surface of the optical axis switching member SW, the deflection surface (optical path coupling plane) of the dichroic mirror ML, and the deflection surface of the dichroic mirror MR is an example of the height adjusting unit. The height adjusting unit is an example of the "second adjustment unit" according to the embodiments. The pupillary distance adjusting unit is an example of the "third adjustment unit" according to the embodiments.

Hereinafter, examples of the configuration of the measurement optical system 300 will be described. In the following, the subject's left eye EL and the subject's right eye ER may be referred to simply as the subject's eye.

Figure 5:
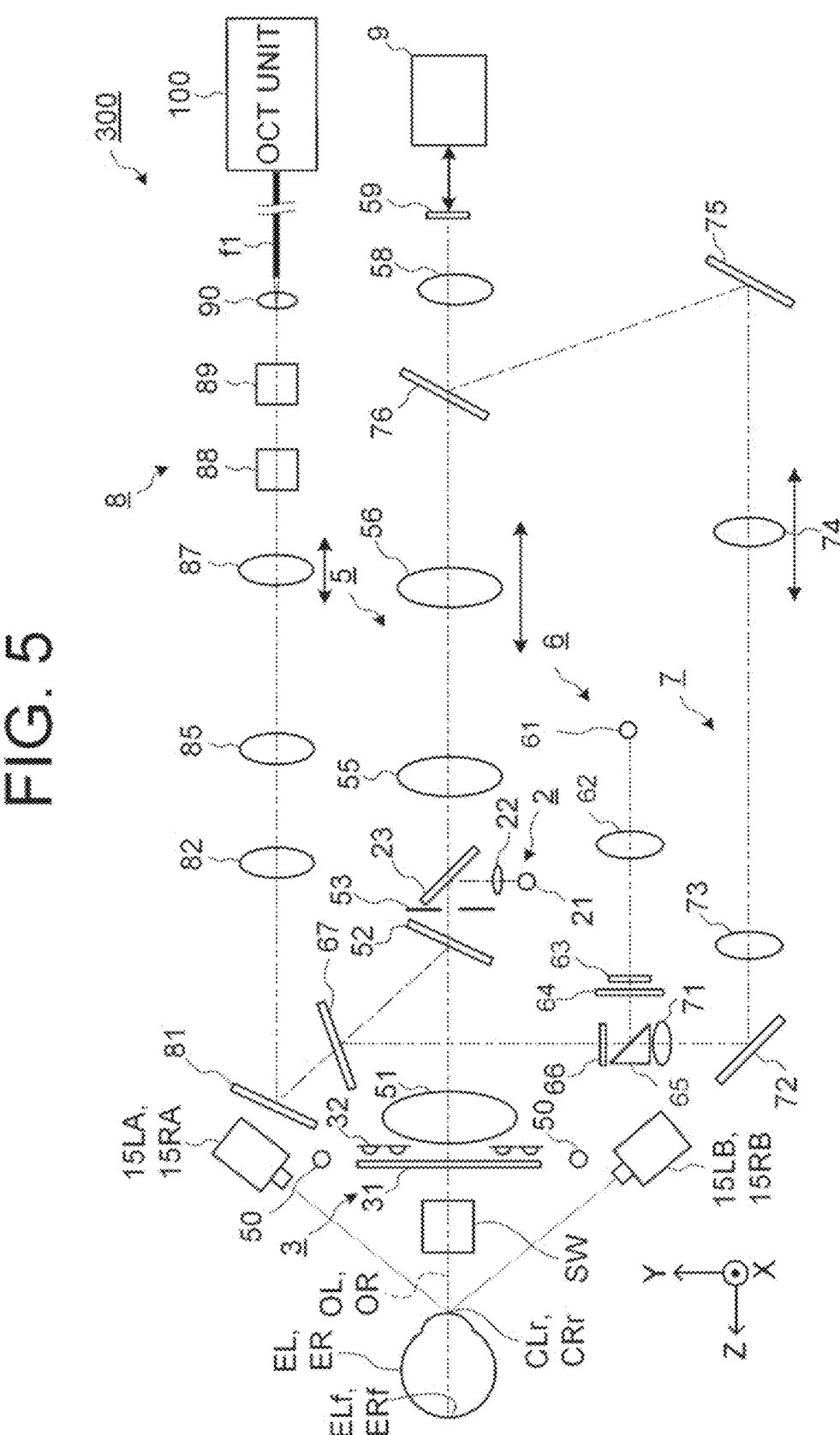
FIG. 5 is a schematic diagram illustrating an example of the configuration of the optical system of the ophthalmic apparatus according to the first embodiment.
Figure 6:
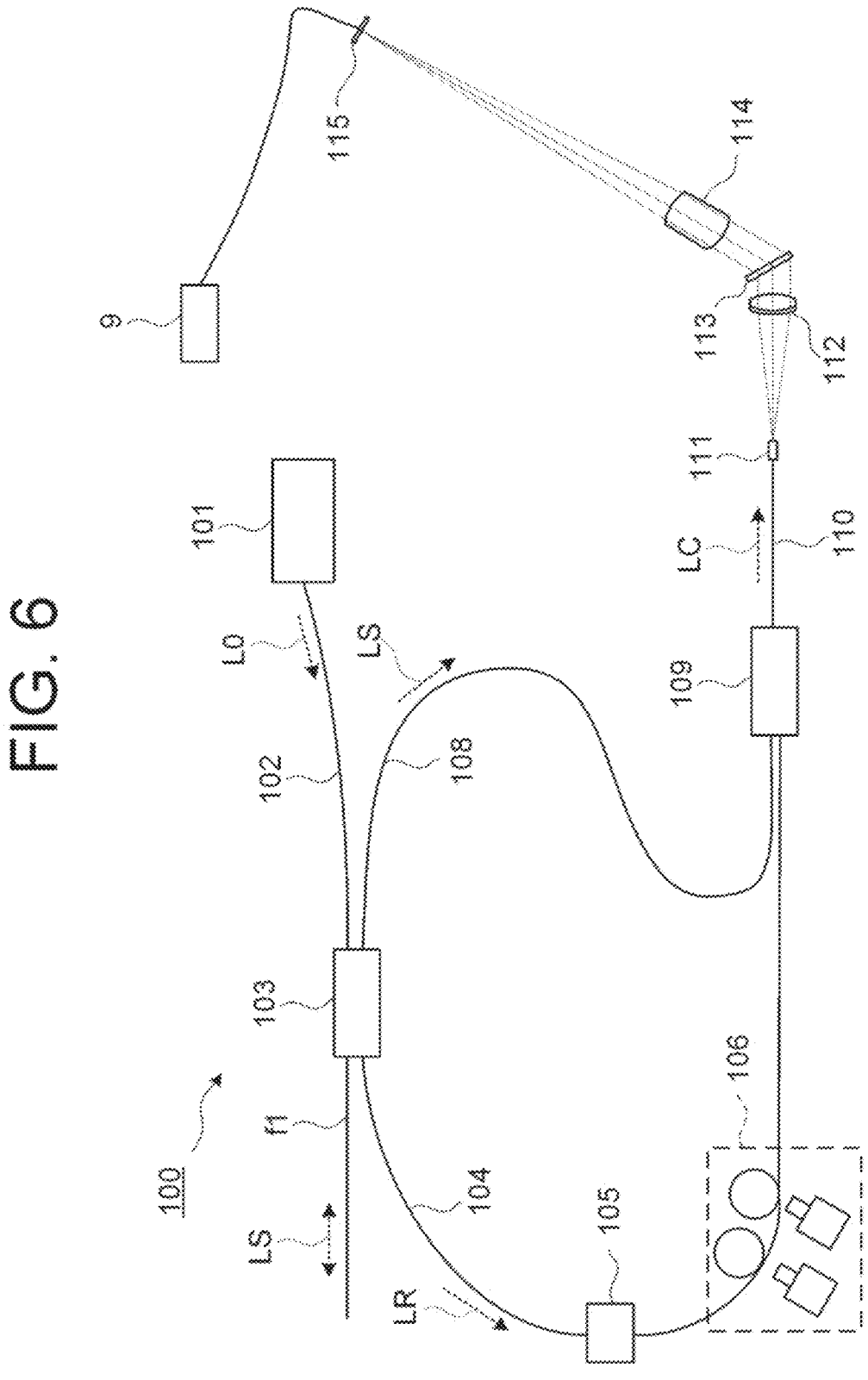
FIG. 6 is a schematic diagram illustrating an example of the configuration of the optical system of the ophthalmic apparatus according to the first embodiment.

FIGS. 5 to 6 show examples of the configuration of the measurement optical system 300 according to the first embodiment. FIG. 5 schematically shows an example of the configuration of the measurement optical system 300 when viewed from the lateral side (X direction). FIG. 6 schematically shows an example of the configuration of the OCT unit 100 in FIG. 5. It should be noted that, in FIG. 5, for convenience of explanation, anterior eye cameras are illustrated so that anterior eye cameras 15LA and 15RA are arranged in the X direction, and anterior eye cameras 15LB and 15 RB are arranged in the X direction. However, the configuration according to the embodiments is not limited to this. In addition, for convenience of explanation, the dichroic mirrors ML and MR shown in FIG. 1 are not shown in FIG. 5. In FIG. 5, parts similar to those in FIG. 1 are denoted by the same reference symbols, and description thereof is omitted as appropriate. In FIG. 6, parts similar to those in FIG. 5 are denoted by the same reference symbols, and description thereof is omitted as appropriate.

The measurement optical system 300 includes an optical system for observing any one of the subject's left eye EL and the subject's right eye ER, an optical system for inspecting any one of the subject's left eye EL and the subject's right eye ER, and a dichroic mirror that wavelength-separates the optical paths of these optical systems. The anterior segment observation system 5 is provided as the optical system for observing any one of the subject's left eye EL and the subject's right eye ER. The keratometry system 3, a refractometry optical system (refractive power measurement optical system), and the OCT optical system 8 are provided as the optical system for inspecting any one of the subject's left eye EL and the subject's right eye ER. The refractometry optical system includes the refractometry projection system 6 and the refractometry light reception system 7, as shown in FIG. 2.

In the first embodiment, the keratometry system 3, the refractometry projection system 6, the refractometry light reception system 7, and the OCT optical system 8 are shared by the inspection for the subject's left eye EL and the inspection for the subject's right eye ER. Further, the optical axis of the OCT optical system 8 is coaxially coupled with the optical axis of the refractometry optical system (refractometry projection system 6, refractometry light reception system 7).

Specifically, the measurement optical system 300 includes a XY alignment system 2, the keratometry system 3, the anterior segment observation system 5, the refractometry projection system 6, the refractometry light reception system 7, the OCT optical system 8, and the anterior segment cameras 15LA, 15RA, 15LB, and 15RB. Hereinafter, for example, it is assumed that light with 940 nm to 1000 nm is used in the anterior segment observation system 5, light with 830 nm to 880 nm is used in the refractometry optical system (refractometry projection system 6, refractometry light reception system 7), light with 800 nm to 900 nm is used in the OCT optical system 8. In this case, light with 400 nm to 700 nm can be used in the fixation projection systems 4L and 4R shown in FIG. 1. In some embodiments, light with 1000 nm to 1100 nm is used in the OCT optical system 8.

(Anterior Segment Observation System 5)

The anterior segment observation system 5 is configured to acquire a moving image of the anterior segment of the subject's left eye EL or the anterior segment of the subject's right eye ER that is on the measurement optical axis where the optical axis of the objective lens 51 (measurement optical system 300) is optically coaxially coupled. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's left eye EL or the anterior segment of the subject's right eye ER.

In some embodiments, the anterior segment illumination light source 50 includes a pair of illumination light sources for illuminating the anterior segment of the subject's left eye EL or the anterior segment of the subject's right eye ER from positions away from the measurement optical axes OL and OR. In some embodiments, the anterior segment illumination light source 50 includes a pair of illumination light sources for illuminating the anterior segment of the subject's left eye EL from positions away from the measurement optical axis OL and a pair of illumination light sources for illuminating the anterior segment of the subject's right eye ER from positions away from the measurement optical axis OR. In this case, one of the pair of illumination light sources for illuminating the anterior segment of the subject's left eye EL and one of the pair of illumination light sources for illuminating the anterior segment of the subject's right eye ER may be shared.

Light reflected from the anterior segment of the subject's left eye EL or the anterior segment of the subject's right eye ER passes through the objective lens 51, is transmitted through a dichroic mirror 52, passes through an hole part formed in a diaphragm (telecentric diaphragm) 53, is transmitted through a half mirror 23, passes through relay lenses 55 and 56, and is transmitted through a dichroic mirror 76. The dichroic mirror 52 couples the optical path of the refractometry optical system with the optical path of the anterior segment observation system 5. In other words, the dichroic mirror 52 separates the optical path of the refractometry measurement optical system from the optical path of the anterior segment observation system 5. The dichroic mirror 52 is disposed so that its optical path coupling plane for coupling these optical paths is inclined with respect to the optical axis of the objective lens 51. The light transmitted through the dichroic mirror 76 forms an image on an imaging surface of the imaging element 59 (area sensor) via an imaging lens 58. The imaging element 59 performs an imaging and a signal outputting at a predetermined rate. The output (video signal) of the imaging element 59 is input to a processor 9 described below. The processor 9 displays an anterior segment image of the subject's left eye EL or an anterior segment image of the subject's right eye ER based on this video signals on a display unit 270 described below. The anterior segment image of the subject's left eye EL and the anterior segment image of the subject's right eye ER are, for example, infrared moving images.

(Anterior Segment Cameras 15LA, 15RA, 15LB, and 15RB)

The anterior segment cameras 15LA and 15LB photograph the anterior segment of the subject's left eye EL. The anterior segment cameras 15LA and 15LB are, for example, video cameras for capturing moving images at a predetermined frame rate. The anterior segment cameras 15LA and 15LB substantially simultaneously photograph the anterior segments from different directions. For example, the anterior segment cameras 15LA and 15LB are used for position matching of the optical system relative to the subject's left eye EL.

The number of anterior segment cameras for photographing the anterior segment of the subject's left eye EL may be any two or more, as long as the configuration is capable of substantially simultaneously photographing the anterior segment from two different directions. Further, one anterior segment camera may also be the imaging element 59 in the anterior segment observation system 5.

The phrase "substantially simultaneously" indicates that the deviation in photography timings at a level where the eye movement is negligible is allowed in the photography with two or more anterior segment cameras. Thereby, images can be acquired using two or more anterior segment cameras when the subject's eye is in the same position (orientation).

The anterior segment cameras 15RA and 15RB photograph the anterior segment of the subject's right eye ER. The anterior segment cameras 15RA and 15RB are, for example, video cameras for capturing moving images at a predetermined frame rate. The anterior segment cameras 15RA and 15RB substantially simultaneously photograph the anterior segments from different directions. For example, the anterior segment cameras 15RA and 15RB are used for position matching of the optical system relative to the subject's right eye ER.

The number of anterior segment cameras for photographing the anterior segment of the subject's right eye ER may be any two or more, as long as the configuration is capable of substantially simultaneously photographing the anterior segment from two different directions. Further, one anterior segment camera may also be the imaging element 59 in the anterior segment observation system 5.

In some embodiments, a known Z alignment system using optical leverage method is provided in place of the anterior segment cameras 15LA and 15LB. In some embodiments, a known Z alignment system using optical leverage method is provided in place of the anterior segment cameras 15RA and 15RB.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's left eye EL or the subject's right eye ER that is on the measurement optical axis where the optical axis of the objective lens 51 (measurement optical system 300) is optically coaxially coupled. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's left eye EL or the subject's right eye ER through the anterior segment observation system 5. Reflected light from the cornea CLr of the subject's left eye EL or the cornea CRr of the subject's right eye ER is guided to the imaging element 59 through the anterior segment observation system 5.

Image (XY bright spot image) based on the reflected light from the cornea CLr is included in the anterior segment image of the subject's left eye EL. Image (XY bright spot image) based on the reflected light from the cornea CRr is included in the anterior segment image of the subject's right eye ER. For example, the processor 9 controls the display unit to display the anterior segment image including the XY bright spot image and an alignment mark on the display unit, for the subject's left eye EL or the subject's right eye ER. In the case of performing XY alignment manually, a user performs an operation for moving the optical system so as to guide the bright spot image in the alignment mark. In the case of performing XY alignment automatically, the processor 9 controls a mechanism for moving the optical system so as to cancel a displacement of the bright spot image relative to the alignment mark. In some embodiments, the processor 9 controls a mechanism for moving the optical system and a mechanism for moving the optical axis switching member SW and the dichroic mirrors ML and MR shown in FIG. 1 so as to cancel a displacement of the bright spot image relative to the alignment mark.

(Keratometry System 3)

The keratometry system 3 is configured to project a ring-shaped light flux (infrared light) for measuring a shape of the cornea CLr of the subject's left eye EL or a shape of the cornea CRr of the subject's right eye ER (corneal shape information) onto the cornea CLr or the cornea CRr. A kerato plate 31 is disposed between the objective lens 51, and the subject's left eye EL and the subject's right eye ER. A kerato-ring light source 32 is provided on the back side (objective lens 51 side) of the kerato plate 31. In the kerato plate 31, a kerato (keratometry) pattern (transmitting part, light transmitting part) that transmits light from the kerato-ring light source 32 is formed along a circumference centered on the optical axis of the objective lens 51 (measurement optical system 300). In some embodiments, in the kerato plate 31, a kerato pattern (transmitting part, light transmitting part) that transmits light from the kerato-ring light source 32 is formed along a circumference around the optical axis. It should be noted that the kerato pattern may be formed in an arc shape (a part of the circumference) around the optical axis. By illuminating the kerato plate 31 with light from the kerato-ring light source 32, the ring-shaped light fluxes (arc-like or circumferential (circular) measurement pattern) are projected onto the cornea CLr or the cornea CRr. The reflected light (kerato-ring image) from the cornea CLr or the cornea CRr is detected by the imaging element 59 along with the anterior segment image of the subject's left eye EL or the anterior segment image of the subject's right eye ER. The processor 9 calculates a corneal shape parameter representing a shape of the cornea CLr and a corneal shape parameter representing a shape of the cornea CRr, by performing a known calculation based on the kerato-ring images.

(Refractometry Projection System 6 and Refractometry Light Reception System 7)

The refractometry optical system includes the refractometry projection system 6 and the refractometry light reception system 7 which are used for refractive power measurement. The refractometry projection system 6 is configured to project light flux (a ring-shaped light flux, for example) (infrared light) for measuring refractive power onto the fundus ELf of the subject's left eye EL or the fundus ERf of the subject's right eye ER that is on the measurement optical axis where the optical axis of the objective lens 51 (measurement optical system 300) is optically coaxially coupled. The refractometry light reception system 7 is configured to receive returning light of the light flux for the refractive power measurement from the subject's left eye EL or returning light of the light flux for the refractive power measurement from the subject's right eye ER.

The refractometry projection system 6 is provided in an optical path branched by a perforated prism 65 provided in an optical path of the refractometry light reception system 7. A hole part formed in the perforated prism 65 is arranged at the pupil conjugate position of the subject's left eye EL or the subject's right eye ER on the measurement optical axis where the optical axis of the objective lens 51 (measurement optical system 300) is optically coaxially coupled. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position of the subject's left eye EL or the subject's right eye ER that is on the measurement optical axis where the optical axis of the objective lens 51 (measurement optical system 300) is optically coaxially coupled.

Light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the subject's left eye EL or the subject's right eye ER that is on the measurement optical axis having adjusted to approximately coincide with the optical axis of the objective lens 51. The rotary prism 66 is used for averaging the light quantity distribution of the ring-shaped light flux with respect to the blood vessel or the diseased site of the fundus or for reducing the speckle noise caused by the light source.

Returning light of the ring-shaped light flux projected onto the fundus ELf or the subject's left eye EL or the fundus ERf of the subject's right eye ER passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a dichroic mirror 76, and forms an image on the imaging surface of the imaging element 59 via the imaging lens 58.

The processor 9 calculates a refractive power value of the subject's left eye EL or the subject's right eye ER by performing the known calculation based on the output of the imaging element 59. Specifically, the processor 9 identifies the ring pattern image from the subject's left eye EL or the subject's right eye ER based on the output from the imaging element 59, and calculates a refractive power value of the subject's left eye EL or a refractive power value of the subject's right eye ER by performing the known calculation on the identified ring pattern image. By sequentially switching the optical axis of the refractometry optical system to each of the measurement optical axes OL and OR, the processor 9 can sequentially calculate the refractive power value of the subject's left eye EL and the refractive power value of the subject's right eye ER. For example, the refractive power value includes a spherical power, an astigmatic power, and an astigmatic axis angle, or an equivalent spherical power.

In some embodiments, the measurement optical system 300 includes the fixation projection systems 4L and 4R.

(OCT Optical System 8)

The OCT optical system 8 is an optical system for performing OCT measurement. For example, the position of the focusing lens 87 is adjusted so that an end face of an optical fiber f1 and an imaging site (fundus or anterior segment) are optically conjugate with each other based on the result of the refractometry performed before the OCT measurement.

The OCT optical system 8 is provided on the optical path wavelength-separated from the optical path of the refractometry optical system by the dichroic mirror 67. The optical axis of the OCT optical system 8 is coaxially coupled with the optical axis of the objective lens 51 (optical axis of the refractometry optical system), and can be adjusted so as to coincide with any one of the measurement optical axes OL and OR.

The OCT optical system 8 includes an OCT unit 100. As shown in FIG. 6, the OCT unit 100 is provided with an optical system for performing OCT measurement (OCT imaging, OCT scan) on any one of the subject's left eye EL and the scan a subject's right eye ER. This optical system has a configuration similar to that of a conventional spectral domain type OCT apparatus. That is, this optical system is configured to: split light (low coherence light) from a broadband light source into reference light and measurement light; make the measurement light having traveled through the subject's eye (OCT measurement site) and the reference light having traveled through a reference optical path interfere with each other to generate interference light; and detect spectral components of the interference light. The result of the detection (detection signal) is sent to the processor 9.

A light source unit 101 emits broadband, low-coherence light L0. The low coherence light L0, for example, has a wavelength components of a wavelength band (e.g., about 800 nm to 900 nm) in the near-infrared region, and has a temporal coherence length of about several tens of microm- eters. In addition, near-infrared light with a wavelength range that is not visible to the human eye, for example, 1040 nm to 1060 nm may be used as the low coherence light L0.

Hereafter, the light source unit 101 is assumed to output the low coherence light L0 with a wavelength component of 840 nm.

The light source unit 101 includes a light emission device, such as a super luminescent diode (SLD), an LED, a semiconductor optical amplifier (SOA), or the like.

The low coherence light L0 emitted from the light source unit 101 is guided to a fiber coupler 103 through an optical fiber 102. The fiber coupler 103 splits the low coherence light L0 into measurement light LS and reference light LR.

The reference light LR is guided through an optical fiber 104 and arrives at an attenuator (optical attenuator) 105. The attenuator 105 automatically adjusts the amount of the reference light LR having been guided through the optical fiber 104 under the control of the processor 9 using a known technology. The reference light LR whose light amount is adjusted by the attenuator 105 is guided to a polarization controller (polarization adjuster) 106 through the optical fiber 104, and arrives at the polarization controller 106. The polarization controller 106 is a device that applies external stress to the looped optical fiber 104 to thereby adjust the polarization state of the reference light LR having been guided through the optical the optical fiber 104. It should be noted that the configuration of the polarization controller 106 is not limited to this and any known technologies can be used. The reference light LR whose polarization state is adjusted by the polarization controller 106 arrives at a fiber coupler 109.

The measurement light LS generated by the fiber coupler 103 is guided to a collimator lens 90 (FIG. 6) through an optical fiber f1, and is made into a parallel light flux by the collimator lens 90. Further, the measurement light LS arrives at the dichroic mirror 67 via an optical path length changing unit 89, an optical scanner 88, the focusing lens 87, the relay lenses 85 and 82, and the reflective mirror 81.

In some embodiments, the focusing lens 87 and the optical scanner 88 are housed in a single unit that is movable in the optical axis direction. This allows the focusing lens 87 and the optical scanner 88 to move in the optical axis direction, while maintaining the optical positional relation- ship between the focusing lens 87 and the optical scanner 88. By configuring the focusing lens 87 and the optical scanner 88 in such a way that they can be moved together, it is possible to adjust the optical system while maintaining the conjugate relationship between the optical scanner 88 and the subject's eye. Further, in this configuration, the magni- fication relationship between the pupil of the subject's eye and the optical scanner 88 can be easily changed by chang- ing the focal length f of the focusing lens 87.

In some embodiments, the focusing lens 87 and the optical scanner 88 are moved independently in the unit in the optical axis direction. In some embodiments, the focusing lens 87 and the optical scanner 88 are moved independently or integrally in the optical axis direction under control from the processor 9. For example, the pupil of the subject's eye is placed at the focal position of the objective lens 51 and the deflection surface of the optical scanner 88 is placed at the focal position of the focusing lens 87. In other words, when the optical scanner 88 is placed at the focal position of the focusing lens 87, the pupil conjugate relationship is main- tained and the deflection surface of the optical scanner 88 is placed at the pupil conjugate position.

The optical path length changing unit 89 changes an optical path length of the measurement light LS. By chang- ing the optical path length of the measurement light LS, a difference between the optical path length of the reference light LR and the optical path length of the measurement light LS can be changed. For example, the optical path length changing unit 89 includes a retroreflector that can move along the optical path of the measurement light LS and the returning light of the measurement light LS, and changes the optical path length of the measurement light LS by moving the retroreflector.

The optical scanner 88 deflects the measurement light LS in a one-dimensionally or two-dimensional manner.

In some embodiments, the optical scanner 88 includes a first galvano mirror and a second galvano mirror. The first galvano mirror deflects the measurement light LS so as to scan the OCT measurement site in the horizontal direction (X direction) orthogonal to the optical axis of the OCT optical system 8. The second galvano mirror deflects the measurement light LS deflected by the first galvano mirror so as to scan the OCT measurement site in the vertical direction (Y direction) orthogonal to the optical axis of the OCT optical system 8. Examples of scan modes of the measurement light LS performed by the optical scanner 88 like this include a horizontal scan, a vertical scan, a cross scan, a radial scan, a circle scan, a concentric scan, a helical (spiral) scan, a Lissajous scan, and the like.

In some embodiments, the optical scanner 88 includes a MEMS scanner (MEMS mirror scanner) that deflects the measurement light LS in a two-dimensional manner. The MEMS scanner deflects the measurement light LS so as to scan the OCT measurement site in the horizontal and vertical directions orthogonal to the optical axis of the OCT optical system 8.

It should be noted that the optical scanner 88 may also include a polygon mirror, a rotating mirror, a dove prism, a double dove prism, a rotation prism, or the like, other than the galvanometer mirror and the MEMS scanner.

The measurement light LS arrived at the dichroic mirror 67 is transmitted through the dichroic mirror 67, is reflected by the dichroic mirror 52, and is refracted by the objective lens 51. The measurement light LS refracted by the objective lens 51 is deflected by the optical axis switching member SW toward the dichroic mirror ML or the dichroic mirror MR. The measurement light LS deflected by the dichroic mirror ML or the dichroic mirror MR is irradiated onto the OCT measurement site of the subject's left eye EL or the subject's right eye ER. The measurement light LS is scat- tered (and reflected) at various depth positions of the OCT measurement site. Back-scattered light of the measurement light LS from the OCT measurement site reversely advances along the same path as the outward path, and is guided to the fiber coupler 103, and arrives at the fiber coupler 109 through an optical fiber 108.

Figure 8:
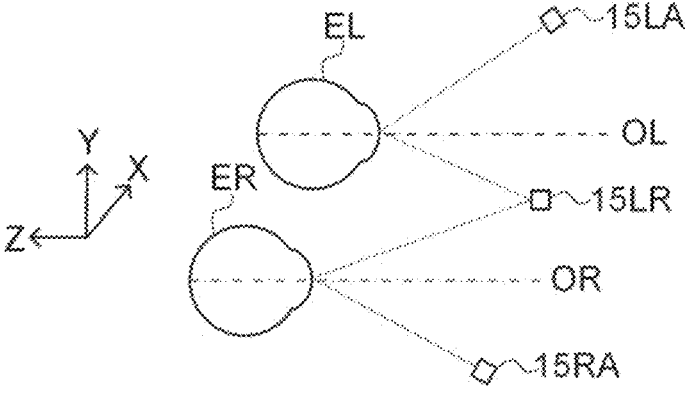
FIG. 8 is a schematic diagram for explaining the optical system of the ophthalmic apparatus according to the first embodiment.

The fiber coupler 109 causes the back-scattered light of the measurement light LS and the reference light LR, the reference light LR having passed through the attenuator 105, and the like, to interfere with each other. Interference light LC thus generated is guided through an optical fiber 110 and is output from an exit end 111. Further, the interference light LC is collimated into a parallel light flux (beam) by a collimator lens 112, is spectrally divided (spectrally decom- posed) by a diffraction grating (spectroscope) 113, is con- verged by a zoom optical system 114, and is projected onto the light receiving surface of a CCD image sensor 115. Note that although FIG. 8 illustrates the diffraction grating 113 of a transmission type, it is also possible to use a spectrally decomposing element of any other type, such as a diffraction grating of reflection type.

The CCD image sensor 115 is a line sensor, for example, with an array of two or more light receiving elements (detectors). The CCD image sensor 115 detects each spectral component of the dispersed interference light LC, and converts it into electric charge(s). The CCD image sensor 115 accumulates the electric charges to generate a detection signal, and sends the signal to the processor 9.

Although a Michelson interferometer is employed in the present embodiment, it is possible to employ any type of interferometer such as Mach-Zehnder-type as appropriate. In place of the CCD image sensor, an image sensor of other type, such as a complementary metal-oxide semiconductor (CMOS) image sensor, may be used.

Further, the configuration as shown in FIG. 5 is configured to change the difference between the optical path length of the measurement light LS and the optical path length of the reference light LR by changing the optical path length of the measurement light LS by the optical path length changing unit 89. However, the configuration according to the embodiments is not limited to this. For example, by changing the optical path length of the reference light LR using a known method, the configuration may be configured to change the difference between the optical path length of the measurement light LS and the optical path length of the reference light LR.

The processor 9 can calculate the refractive power value of the subject's left eye EL from the result of the measurement obtained using the refractometry optical system, and can move the refractometry light source 61 in the optical axis direction to a position where the fundus ELf, the refractometry light source 61, and the imaging element 59 are conjugate with each other, based on the calculated refractive power value. Further, the processor 9 can calculate the refractive power value of the subject's right eye ER from the result of the measurement obtained using the refractometry optical system, and can move the refractometry light source 61 in the optical axis direction to a position where the fundus ERf, the refractometry light source 61, and the imaging element 59 are conjugate with each other, based on the calculated refractive power value. In some embodiments, the processor 9 moves the focusing lens 74 to a position corresponding to a composite refractive power value (e.g., intermediate power) obtained from the refractive power value of the subject's left eye EL and the refractive power value of the subject's right eye ER.

In some embodiments, the processor 9 moves the focusing lens 87 and the optical scanner 88 in its optical axis direction in conjunction with the movement of the focusing lens 74. In some embodiments, the processor 9 moves the liquid crystal panel 41L (fixation unit 40L) in its optical axis direction in conjunction with the movement of the refractometry light source 61 and the focusing lens 74. In some embodiments, the processor 9 moves the liquid crystal panel 41R (fixation unit 40R) in its optical axis direction in conjunction with the movement of the refractometry light source 61 and the focusing lens 74.

In the above embodiments, the function of at least one of the focusing lens 74 or the focusing lens 87 may be realized by a liquid crystal lens or a liquid lens.

The configuration of the optical system of the ophthalmic apparatus 1 according to the embodiments is not limited to the configuration shown in FIGS. 1 to 6.

<Example of Arrangement of Anterior Segment Cameras>

Figure 7:
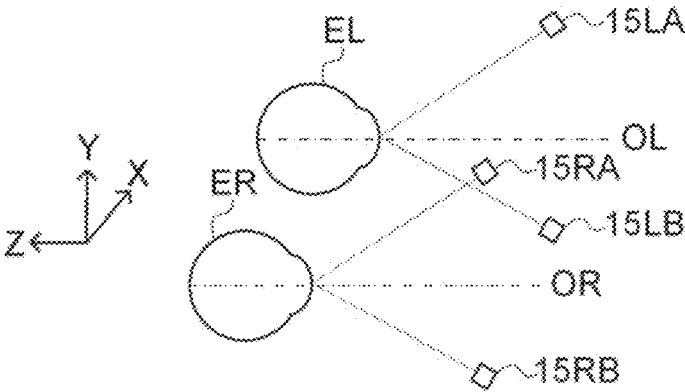
FIG. 7 is a schematic diagram for explaining the optical system of the ophthalmic apparatus according to the first embodiment.

FIG. 7 schematically shows an example of the arrangement of the anterior segment cameras 15LA, 15RA, 15LB, and 15RB.

As shown in FIG. 7, for example, the anterior segment cameras 15LA and 15LB are arranged so that the anterior segment camera 15LA photographs the subject's left eye EL from a direction that forms a positive angle in the Y direction with reference to the measurement optical axis OL and the anterior segment camera 15LB photographs the subject's left eye EL from a direction that forms a negative angle in the Y direction with reference to the measurement optical axis OL. The anterior segment cameras 15LA and 15LB may be arranged so that the anterior segment camera 15LA photographs the subject's left eye EL from a direction that forms a positive angle in the X direction with reference to the measurement optical axis OL and the anterior segment camera 15LB photographs the subject's left eye EL from a direction that forms a negative angle in the X direction with reference to the measurement optical axis OL.

In the same way, the anterior segment cameras 15RA and 15RB are arranged so that the anterior segment camera 15RA photographs the subject's right eye ER from a direction that forms a positive angle in the Y direction with reference to the measurement optical axis OR and the anterior segment camera 15RB photographs the subject's right eye ER from a direction that forms a negative angle in the Y direction with reference to the measurement optical axis OR. The anterior segment cameras 15RA and 15RB may be arranged so that the anterior segment camera 15RA photographs the subject's right eye ER from a direction that forms a positive angle in the X direction with reference to the measurement optical axis OR and the anterior segment camera 15RB photographs the subject's right eye ER from a direction that forms a negative angle in the X direction with reference to the measurement optical axis OR.

A part of the functions of anterior segment cameras 15LA, 15RA, 15LB, and 15RB may be realized by a single anterior segment camera.

FIG. 8 schematically shows an example of the arrangement when the functions of the anterior segment cameras 15LB and 15RB in FIG. 1 are realized by an anterior segment camera 15LR.

The anterior segment camera 15LR is configured to capture an image of the anterior segment of the subject's left eye EL and the anterior segment of the subject's right eye ER. As shown in FIG. 8, for example, the anterior segment cameras 15LA and 15LR are arranged so that the anterior segment camera 15LA photographs the subject's left eye EL from a direction that forms a positive angle in the Y direction with reference to the measurement optical axis OL and the anterior segment camera 15LR photographs the subject's left eye EL from a direction that forms a negative angle in the Y direction with reference to the measurement optical axis OL. The anterior segment cameras 15LA and 15LR may be arranged so that the anterior segment camera 15LA photographs the subject's left eye EL from a direction that forms a positive angle in the X direction with reference to the measurement optical axis OL and the anterior segment camera 15LR photographs the subject's left eye EL from a direction that forms a negative angle in the X direction with reference to the measurement optical axis OL.

In the same way, the anterior segment cameras 15RA and 15LR are arranged so that the anterior segment camera 15RA photographs the subject's right eye ER from a direction that forms a positive angle in the Y direction with reference to the measurement optical axis OR and the anterior segment camera 15LR photographs the subject's right eye ER from a direction that forms a negative angle in the Y direction with reference to the measurement optical axis OR. The anterior segment cameras 15LR and 15RA may be arranged so that the anterior segment camera 15LR photographs the subject's right eye ER from a direction that forms a positive angle in the X direction with reference to the measurement optical axis OR and the anterior segment camera 15RA photographs the subject's right eye ER from a direction that forms a negative angle in the X direction with reference to the measurement optical axis OR.

The ophthalmic apparatus 1 according to the embodiments can perform refractometry (refractive power measurement) using the refractometry optical system and OCT measurement using the OCT optical system 8, while sharing the objective lens with at least the refractometry optical system and the OCT optical system 8. Each of the refractometry and the OCT measurement can be performed sequentially on either the subject's left eye or the subject's right eye. In some embodiments, before performing OCT measurement on one of the subject's left eye EL and the subject's right eye ER, the optical path length of the reference optical path is adjusted by controlling the OCT optical system 8 based on the axial length and the refractive power of another of the subject's left eye EL and subject's right eye ER. This allows to set the measurement environment estimated from the measurement environment of another subject's eye prior to performing OCT measurement on one subject's eye. As a result, the time required for OCT measurement can be shortened.

The ophthalmic apparatus 1 according to the first embodiment can adjust the optical axis (axis of the optical path of the measurement light) of the OCT optical system 8.

<Example of Adjustment of OCT Optical System 8>

Figure 9A:
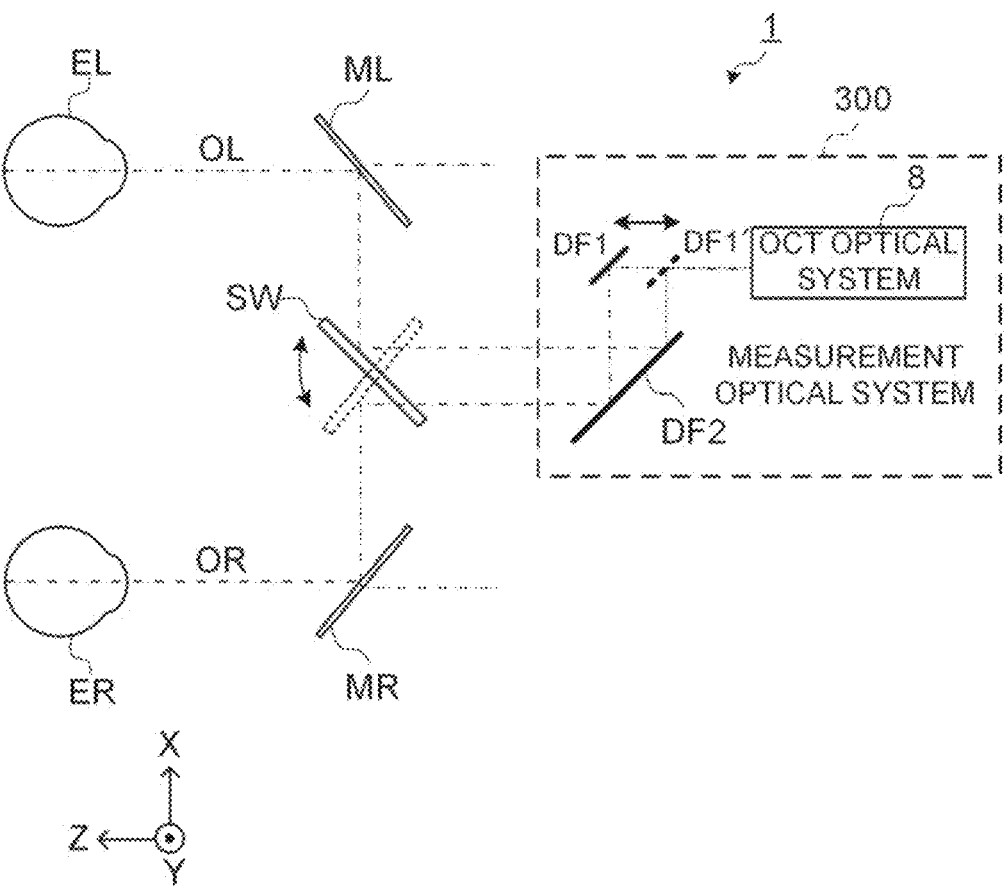
FIG. 9A is a schematic diagram for explaining the optical system of the ophthalmic apparatus according to the first embodiment.

FIG. 9A shows a diagram describing a first adjustment example of the OCT optical system 8 according to the first embodiment. In FIG. 9A, like reference numerals designate like parts as in FIG. 1. The same description may not be repeated.

The measurement optical system 300 includes deflection members DF1 and DF2. The deflection member DF1 deflects the optical axis of the OCT optical system 8 toward the deflection member DF2. The deflection member DF2 deflects the optical axis deflected by the deflection member DF1 toward the optical axis switching member SW. For example, by moving the deflection member DF1 in the optical axis direction, the optical axis of the OCT optical system 8 can be adjusted so as to approximately coincide with one of the measurement optical axes OL and OR from another of the measurement optical axes OL and OR. For example, at the position of the deflection member DF1', the optical axis of the OCT optical system 8 can be approximately coincided with the measurement optical axis OL, and at the position of the deflection member DF1, the optical axis of the OCT optical system 8 can be approximately coincided with the measurement optical axis OR.

For example, the ophthalmic apparatus 1 can approximately coincide with the optical axis of the OCT optical system 8 with any one of the measurement optical axes OL and OR, by moving the deflection member DF1 in accordance with the pupillary distance of the subject.

In FIG. 5, the reflective mirror 81 is an example of the deflection member DF1. The dichroic mirror 52 is an example of the deflection member DF2.

Figure 9B:
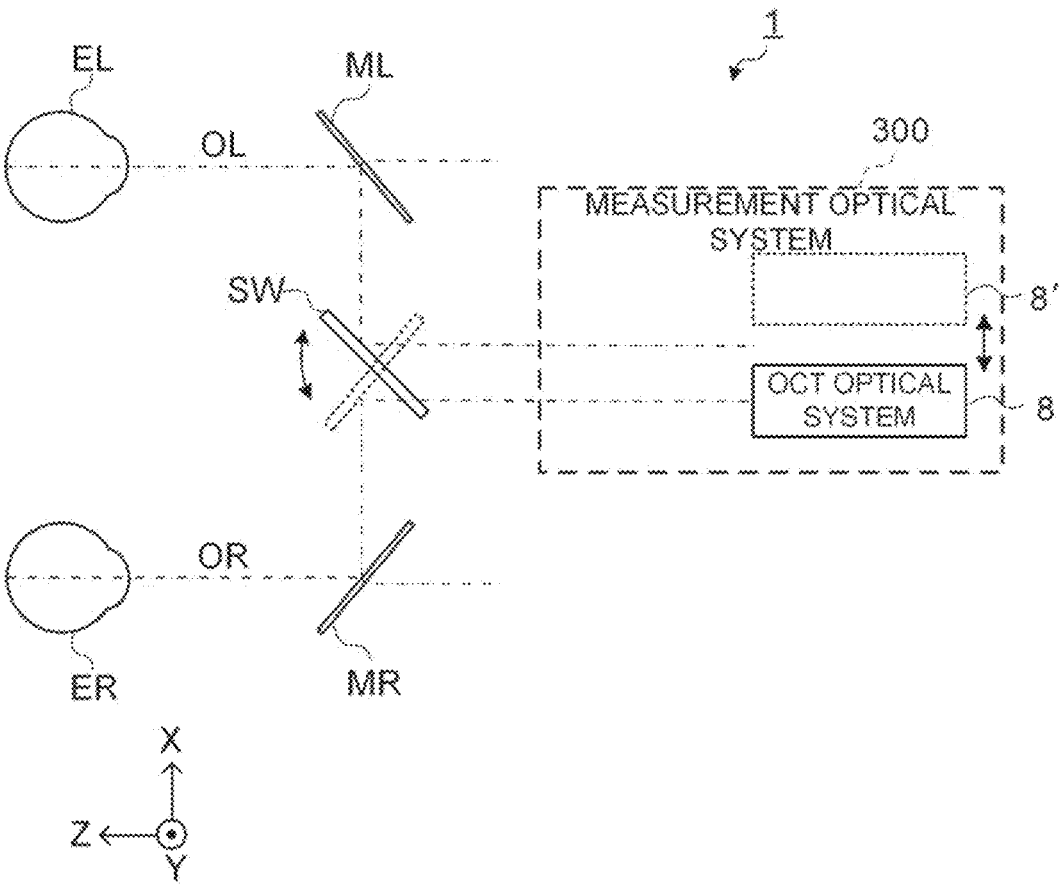
FIG. 9B is a schematic diagram for explaining the optical system of the ophthalmic apparatus according to the first embodiment.

FIG. 9B shows a diagram describing a second adjustment example of the OCT optical system 8 according to the first embodiment. In FIG. 9B, like reference numerals designate like parts as in FIG. 1. The same description may not be repeated.

The measurement optical system 300 (ophthalmic apparatus 1) includes a movement mechanism that moves the OCT optical system 8 under the control from the controller described below. For example, this movement mechanism moves the OCT optical system 8 (specifically, the OCT unit 100) independently of optical elements arranged on the path from the objective lens 51 to the collimator lens 90. For example, by moving the OCT unit 100 in a direction intersection the optical axis of the OCT optical system 8, the optical axis of the OCT optical system 8 can be adjusted so as to approximately coincide with one of the measurement optical axes OL and OR from another of the measurement optical axes OL and OR. For example, at the position of the OCT optical system 8', the optical axis of the OCT optical system 8 can be approximately coincided with the measurement optical axis OL, and at the position of OCT optical system 8, the optical axis of the OCT optical system 8 can be approximately coincided with the measurement optical axis OR.

For example, the ophthalmic apparatus 1 can approximately coincide with the optical axis of the OCT optical system 8 with any one of the measurement optical axes OL and OR, by moving the position of the optical axis of the OCT optical system 8 (OCT unit 100) in accordance with the pupillary distance of the subject.

Further, as a third adjustment example of the optical axis of the OCT optical system 8 according to the first embodiment, the deflection direction of the OCT optical system 8 can be changed using the optical member arranged on the path of the measurement light. Examples of the optical member include the reflective mirror 81 shown in FIG. 5, the dichroic mirror 52 shown in FIG. 5, and a reflective mirror not shown. For example, the optical axis of OCT optical system 8 is adjusted by changing the deflection direction of the optical axis of the OCT optical system 8 deflected by the optical member based on a pupillary distance of the subject.

<Configuration of Processing System>

The processing system of the ophthalmic apparatus 1 will be described.

Figure 10:
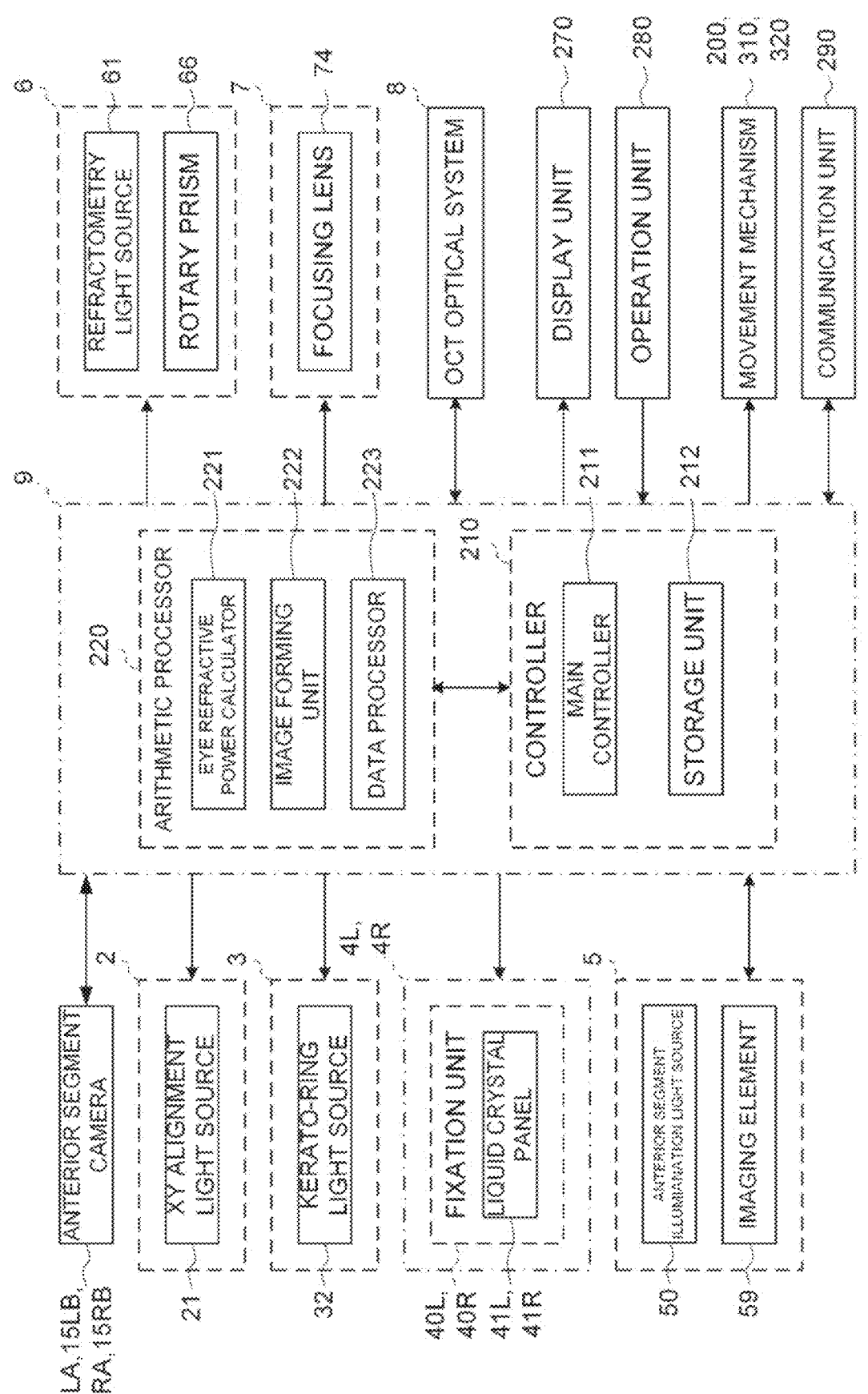
FIG. 10 is a schematic diagram illustrating an example of a configuration of a processing system of the ophthalmic apparatus according to the first embodiment.
Figure 11:
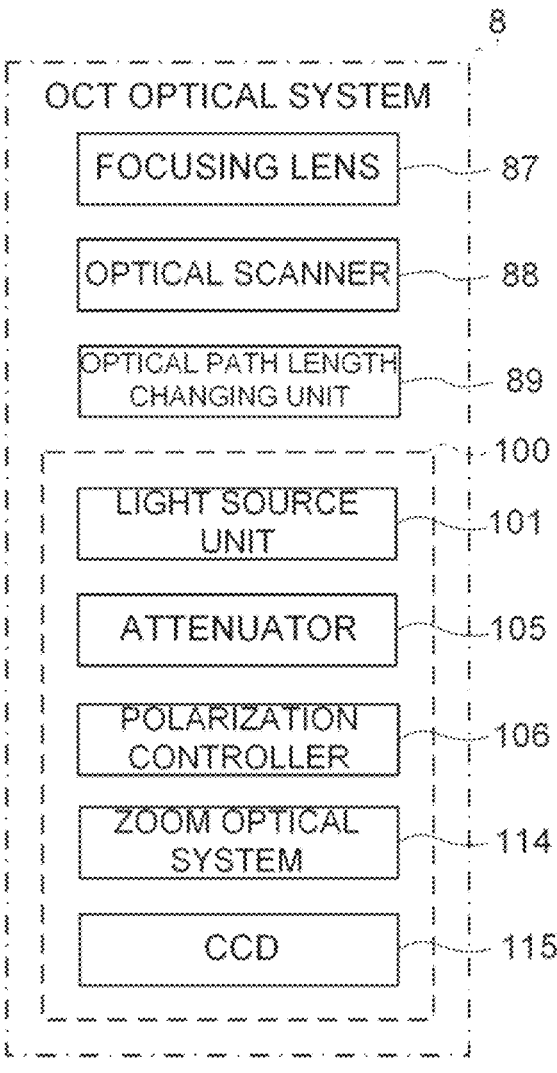
FIG. 11 is a schematic diagram illustrating an example of a configuration of the processing system of the ophthalmic apparatus according to the first embodiment.

FIGS. 10 and 11 show examples of a functional configuration of a processing system of the ophthalmic apparatus 1. FIG. 10 shows an example of a functional block diagram illustrating the processing system of the ophthalmic apparatus 1. FIG. 11 shows an example of a functional block diagram of the OCT optical system in FIG. 10. In FIGS. 10 and 11, like reference numerals designate like parts as in FIG. 1 or FIG. 5. The same description may not be repeated.

The processor (processing unit) 9 controls each part of the ophthalmic apparatus 1. Further, the processor 9 is capable of performing various types of arithmetic processing. The functions of the processor 9 are realized by processing circuitry. The processor 9 includes one or more processors. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processor 9 realizes the function according to the embodiments, for example, by reading out a computer program stored in a storage circuit or a storage device and executing the computer program.

In some embodiments, the processor 9 includes a single processor that realize the functions according to the embodiments. In some embodiments, the processor 9 includes a plurality of processors, each of the processors realizing one or more functions according to the embodiments.

The processor 9 includes a controller 210 and the arithmetic processor 220. Further, the ophthalmic apparatus 1 includes movement mechanisms 200, 310, and 320, a display unit 270, an operation unit 280, and a communication unit 290.

The movement mechanism 200 is a mechanism for moving a head unit in the X direction, the Y direction, and the Z direction, the head unit housing the optical systems such as the anterior segment cameras 15LA, 15LB, 15RA, 15RB, the XY alignment system 2, the keratometry system 3, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

The movement mechanism 310 moves the optical axis switching member SW as shown in FIG. 3. For example, the movement mechanism 310 has the same configuration as the movement mechanism 200. The controller 210 (main controller 211) controls the movement mechanism 310 by sending a control signal to the actuator.

The movement mechanism 320 independently rotates each of the dichroic mirrors ML and MR around the rotary axis, as shown in FIG. 4. For example, the movement mechanism 320 is provided with an actuator that generates driving force for rotating each of the dichroic mirrors ML and MR and a transmission mechanism that transmits the driving force to the dichroic mirrors ML and MR. The controller 210 (main controller 211) controls the movement mechanism 320 by sending a control signal to the actuator.

Although not shown in the figures, the ophthalmic apparatus 1 can include a mechanism for adjusting the optical axis of the OCT optical system 8 shown in FIGS. 9A and 9B. For example, the mechanism described above has the same configuration as the movement mechanism 200 or 320. The controller 210 (main controller 211) controls the mechanism described above by sending a control signal to the actuator.

(Controller 210)

The controller 210 includes a processor and controls each part of the ophthalmic apparatus 1. The controller 210 includes a main controller 211 and a storage unit 212. The storage unit 212 stores, in advance, a computer program for controlling the ophthalmic apparatus 1. Examples of the computer programs include a program for controlling the anterior segment cameras, a program for controlling the XY alignment system, a program for controlling the keratometry system, a program for controlling the fixation projection system, a program for controlling the anterior segment observation, a program for controlling the refractometry, a program for controlling the OCT measurement, a program for arithmetic processing, a program for user interface, a program for controlling the communication, and the like. The main controller 211 operates according to the computer programs, and thereby the controller 210 performs the control processing.

The main controller 211 performs various controls of the ophthalmic apparatus, as a measurement controller. Examples of the control for the anterior segment cameras 15LA, 15LB, 15RA, and 15RB include exposure adjustment, gain adjustment, frame rate adjustment, imaging timing adjustment, imaging range adjustment, imaging magnification adjustment, synchronization control for the anterior segment cameras 15LA and 15LB, synchronization control for the anterior segment cameras 15RA and 15RB, and synchronization control for the anterior segment cameras 15LA, 15LB, 15RA, and 15RB.

The anterior segment cameras 15LA and 15LB substantially simultaneously photograph the anterior segment of the subject's left eye EL from different directions. The main controller 211 controls the data processor 223 described below to identify a three-dimensional position of the subject's left eye EL from two photographic image acquired by the anterior segment cameras 15LA and 15LB. The data processor 223 identifies a characteristic position corresponding to a characteristic site of the anterior segment of the subject's left eye EL, by analyzing the each of the two photographic images substantially simultaneously obtained by the anterior segment cameras 15LA and 15LB and applying a known trigonometry, as disclosed in Japanese Unexamined Patent No. 2013-248376. The characteristic site of the anterior segment is, for example, the center of the pupil. Further, the data processor 223 identifies the three-dimensional position of the subject's left eye EL based on the identified characteristic position. In this example, the position of the center of the pupil is approximated to the position of the subject's eye. It should be noted that by using the distance between the corneal apex and the pupil in the subject's eye, or the distance between the corneal apex and the pupil in the standard eye (eye model, mean value, etc.), the position of the corneal apex can be obtained as the position of the subject's eye.

The anterior segment cameras 15RA and 15RB substantially simultaneously photograph the anterior segment of the subject's right eye ER from different directions. The main controller 211 controls the data processor 223 described below to identify a three-dimensional position of the subject's right eye ER from two photographic image acquired by the anterior segment cameras 15RA and 15RB. The data processor 223 identifies a characteristic position corresponding to a characteristic site of the anterior segment of the subject's right eye ER, by analyzing the each of the two photographic images substantially simultaneously obtained by the anterior segment cameras 15RA and 15RB and applying a known trigonometry. Further, the data processor 223 identifies the three-dimensional position of the subject's right eye ER based on the identified characteristic position.

The main controller 211 can perform position matching of the optical system of apparatus relative to the subject's left eye EL and the subject's right eye ER, by controlling the movement mechanism 200 based on the three-dimensional position of the subject's left eye EL and the three-dimensional position of the subject's right eye ER, the three-dimensional positions being identified by the data processor 223. In addition, the main controller 211 can perform adjustment of the pupillary distance and adjustment of the angle of convergence, by controlling the movement mechanisms 310 and 320 based on the identified three-dimensional position of the subject's left eye EL and the identified three-dimensional position of the subject's right eye ER. Further, the main controller 211 can perform optical axis adjustment to approximately coincide the optical axis of the OCT optical system 8 (i.e., optical axis of the measurement optical system 300 or optical axis of the objective lens 51) with any one of the measurement optical axes OL and OR based on the identified three-dimensional position of the subject's left eye EL or the identified three-dimensional position of the subject's right eye ER.

Examples of control for the XY alignment system 2 include control of the XY alignment light source 21, and the like. Examples of the control of the XY alignment light source 21 include turning on and off of the light source, adjustment of an amount of light, adjustment of aperture, and the like. Thereby, the XY alignment light source 21 can be switched between lighting and non-lighting, or the amount of light can be changed. The main controller 211 acquires a signal detected by the imaging element 59, and identifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image relative to a predetermined target position (XY alignment).

Examples of control for the keratometry system 3 include control of the kerato-ring light source 32, and the like. Examples of the control of the kerato-ring light source 32 include turning on and off of the light source, adjustment of an amount of light, adjustment of aperture, and the like. Thereby, the kerato-ring light source 32 can be switched between lighting and non-lighting, or the amount of light can be changed. The main controller 211 controls the arithmetic processor 220 to perform a known calculation on a kerato-ring image detected by the imaging element 59. Thereby, corneal shape parameters of the subject's eye are obtained.

Examples of control for the fixation projection systems 4L and 4R include control for the liquid crystal panels 41L and 41R, movement control for the fixation units 40L and 40R, and the like. Examples of the control of the liquid crystal panels 41L and 41R include displaying on and off of the fixation target, switching the fixation target in accordance with the type of the inspection or the measurement, switching the display position of the fixation target, and the like.

Further, for example, the fixation projection systems 4L and 4R are provided with movement mechanisms that move the liquid crystal panels 41L and 41R (or fixation units 40L and 40R) in the optical axis directions, respectively. As is the case with the movement mechanism 200, each of the movement mechanisms is provided with an actuator that generates driving force for moving the movement mechanism and a transmission mechanism that transmits the driving force from the actuator to the movement mechanism. The main controller 211 controls the movement mechanism by sending a control signal to the actuator to move at least each of the liquid crystal panels 41L and 41R in the optical axis direction. Thereby, the positions of the liquid crystal panels 41L and 41R are adjusted so that the liquid crystal panel 41L and the fundus ELf are optically conjugate and the liquid crystal panel 41R and the fundus ERf are optically conjugate, respectively.

Examples of the control for the anterior segment observation system 5 include control for an anterior segment illumination light source 50, control for a lens movement mechanism that moves the relay lens 56, control for the imaging element 59, and the like. Examples of control for the anterior segment illumination light source 50 include turning on and off the light source, adjustment of an amount of light, adjustment of aperture, and the like. Thereby, the anterior segment illumination light source 50 is switched between lighting and non-lighting, or the amount of light is changed. As is the case with the movement mechanism 200, the lens movement mechanism is provided with an actuator that generates driving force for moving the lens movement mechanism and a transmission mechanism that transmits the driving force from the actuator to the movement mechanism. The main controller 211 controls the movement mechanism by sending a control signal to the actuator to move the relay lens 56 in the optical axis direction. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of light amount, and the like. Thereby, the refractometry light source 61 can be switched between lighting and non-lighting, or the amount of light can be changed. For example, the refractometry projection system 6 includes a movement mechanism that moves the refractometry light source 61 in the optical axis direction. As is the case with the movement mechanism 200, each of the movement mechanisms is provided with an actuator that generates driving force for moving the movement mechanism and a transmission mechanism that transmits the driving force from the actuator to the movement mechanism. The main controller 211 controls the movement mechanism by sending a control signal to the actuator to move the refractometry light source 61 in the optical axis direction. Examples of the control for the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control for the focusing lens 74, and the like. Examples of the control for the focusing lens 74 include control of moving the focusing lens 74 in the optical axis direction. For example, the refractometry light reception system 7 includes a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 in the optical axis direction respectively, depending on the refractive power of the subject's left eye EL, the refractive power of the subject's right eye ER, or a synthetic refractive power of the refractive power of the subject's left eye EL and the refractive power of the subject's right eye ER, for example, so that the refractometry light source 61, the fundus ELf or the fundus ERf, and the imaging element 59 are optically conjugate with each other.

Examples of control for the OCT optical system 8 include control for the light source unit 101, control for the attenuator 105, control for the polarization controller 106, control for the zoom optical system 114, control for the CCD image sensor 115, control for the focusing lens 87, control for the optical scanner 88, control for the optical path length changing unit 89, and the like.

Examples of the control for the light source unit 101 include turning on and off the light source, adjustment of the amount of light, adjustment of an aperture, and the like. Examples of the control for the attenuator 105 include adjustment of the light amount of the reference light LR, and the like. Examples of the control for the polarization controller 106 include adjustment of the polarization state of the reference light LR, and the like. Examples of the zoom optical system 114 include control for the optical magnification, and the like. Examples of the control for the CCD image sensor 115 include adjustment of exposure of the CCD image sensor 115, adjustment of gain of the CCD image sensor 115, adjustment of detecting rate of the CCD image sensor 115, and the like. The main controller 211 acquires a signal detected by the CCD image sensor 115 and controls the arithmetic processor 220 to perform processing such as forming image based on the acquired signal and the like.

Examples of the control for the focusing lens 87 include control of moving the focusing lens 87 in the optical axis direction, and the like. For example, the OCT optical system 8 includes a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction.

In some embodiments, a holding member that holds the focusing lens 74 and the focusing lens 87, and the driver that drives the holding member are provided in the ophthalmic apparatus 1. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74.

Examples of control for the optical scanner 88 include setting the scan mode to scan the measurement site with a predetermined scan pattern, control for the scan range, control for the scan speed, and the like. By controlling the scan range (scan start position and scan end position), an angle range of the deflection surface that deflects the measurement light LS can be controlled. By controlling the scan speed, a change speed of the angle of the deflection surface can be controlled. The main controller 211 controls at least one of the scan mode, the scan range, or the scan speed, by outputting control signal(s) to the optical scanner 88.

Examples of the control for the optical path length changing unit 89 include control of the optical path length of the measurement light LS, and the like. The main controller 211 controls the optical path length changing unit 89 to change the optical path length of the measurement light LS by outputting control signal(s) to the optical path length changing unit 89.

Further, the main controller 211 performs a process of writing data in the storage unit 212 and a process of reading out data from the storage unit 212.

(Storage Unit 212)

The storage unit 212 stores various types of data. Examples of the data stored in the storage unit 212 include a measurement result of the objective measurement (result of OCT measurement), image data of the OCT image, image data of the anterior segment image, a result of the subjective inspection, subject's eye information, and the like. The subject's eye information includes information on the subject such as patient ID and name, and information on the subject's eye such as identification information of the left eye/right eye. The storage unit 212 further stores various types of programs and data to run the ophthalmic apparatus.

(Arithmetic Processor 220)

The arithmetic processor 220 includes a processor, and performs various kinds of arithmetic processes. A storage unit not shown (for example, the storage unit 212) stores, in advance, a computer program for performing various kinds of arithmetic processes. The processor operates according to the computer programs, and thereby the processor realizes the functions of each part that performs the various kinds of arithmetic processes.

As shown in FIG. 10, the arithmetic processor 220 includes an eye refractive power calculator 221, an image forming unit 222, and the data processor 223.

The eye refractive power calculator 221 calculates a refractive power value of the subject's left eye EL and the subject's right eye ER, respectively, based on the results of the refractometry sequentially performed on the both eyes. The image forming unit 222 forms the OCT image data based on the detection result of the interference light LC acquired using the OCT optical system 8. The data processor 223 performs various kinds of data processing (e.g., image processing) and various kinds of analysis on the measurement result (detection result of the interference light LC, etc.) obtained using the optical system included in the ophthalmic apparatus 1 and/or the OCT image formed by the image forming unit 222.

(Eye Refractive Power Calculator 221)

The eye refractive power calculator 221 analyzes a ring image (pattern image) acquired by receiving the returning light of the ring-shaped light flux (ring-shaped measurement pattern) by the imaging element 59, the ring-shaped light flux being projected onto the fundus ELf by the refractometry projection system 6, and calculates the refractive power value of the subject's left eye EL. Further, the eye refractive power calculator 221 analyzes a ring image (pattern image) acquired by receiving the returning light of the ring-shaped light flux by the imaging element 59, the ring-shaped light flux being projected onto the fundus ERf by the refractometry projection system 6, and calculates the refractive power value of the subject's right eye ER. For example, for each ring image, the eye refractive power calculator 221 obtains a position of the center of gravity of the ring image from the brightness distribution in the image representing the ring image, obtains brightness distributions along a plurality of scanning directions extending radially from the position of the center of gravity, and identifies a ring image from these brightness distributions. Subsequently, the eye refractive power calculator 221 obtains an approximate ellipse of the identified ring image and obtains a spherical power, an astigmatic power, and an astigmatic axis angle by assigning a major axis and a minor axis of the approximate ellipse to a known formula. Alternatively, the eye refractive power calculator 221 can obtain the eye refractive power parameter based on deformation and displacement of the ring image with respect to the reference pattern.

Further, the eye refractive power calculator 221 calculates a corneal refractive power, a corneal astigmatism power, and a corneal astigmatic axis angle of the subject's left eye EL based on the kerato-ring image of the subject's left eye EL acquired by the anterior segment observation system 5. Further, the eye refractive power calculator 221 calculates a corneal refractive power, a corneal astigmatism power, and a corneal astigmatic axis angle of the subject's right eye ER based on the kerato-ring image of the subject's right eye ER acquired by the anterior segment observation system 5. For example, for each of the kerato-ring images, the eye refractive power calculator 221 calculates a corneal curvature radius of the steepest meridian and/or the flattest meridian of the anterior surface of the cornea by analyzing the kerato-ring image and calculates above parameters based on the corneal curvature radius.

(Image Forming Unit 222)

The image forming unit 222 forms the image data of the OCT image (tomographic image) of the subject's eye based on the detection result of the interference light LC acquired using the CCD image sensor 115. That is, the image forming unit 222 forms the image data of the subject's eye based on the detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A-lines. Here, the A-lines are the paths of the measurement light LS within the subject's eye.

In order to improve the image quality, it is possible to repeatedly perform scan with the same pattern a plurality of times to collect a plurality of data sets, and to compose (i.e., average) the plurality of data sets.

(Data Processor 223)

The data processor 223 performs various kinds of data processing (e.g., image processing) and various kinds of analysis processing on the tomographic image formed by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye by performing known image processing such as interpolation processing for interpolating pixels between tomographic images. In the case of displaying an image based on the volume data, the data processor 223 performs rendering processing on the volume data so as to form a pseudo three-dimensional image viewed from a specific line-of-sight direction.

The data processor 223 performs known image processing such as interpolation for interpolating pixels between the OCT images (tomographic images) formed by the image forming unit 222 to form the image data of the three-dimensional image of the fundus or the anterior segment. It should be noted that the image data of the three-dimensional image means image data in which the positions of pixels are defined in a three-dimensional coordinate system. Examples of the image data of the three-dimensional image include image data defined by voxels three-dimensionally arranged. Such image data is referred to as volume data or voxel data. To display an image based on volume data, the data processor 223 performs image rendering processing (e.g., volume rendering, maximum intensity projection (MIP)) on the volume data to form image data of a pseudo three-dimensional image taken from a specific view direction. The pseudo three-dimensional image is displayed on a display device such as the display unit 270.

Further, stack data of a plurality of tomographic images may be formed as the image data of the three-dimensional image. The stack data is image data formed by three-dimensionally arranging tomographic images along a plurality of scan lines based on positional relationship of the scan lines. That is, the stack data is image data obtained by representing tomographic images, which are originally defined in their respective two-dimensional coordinate systems, by a single three-dimensional coordinate system. That is, the stack data is image data formed by embedding tomographic images into a single three-dimensional space.

The data processor 223 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as a B-mode image or a C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set in a predetermined direction. Examples of the part of the three-dimensional data set include partial data corresponding to a specific layer. An image having a viewpoint on the front side of the subject's eye, such as the C-mode image, the projection image, and the shadowgram, is called a front image (en-face image).

The data processor 223 can build (form) the B-mode image or the front image (blood vessel emphasized image, angiogram) in which retinal blood vessels and choroidal blood vessels are emphasized (highlighted), based on data (for example, B-scan image data) acquired in time series by performing OCT scan. For example, the OCT data in time series can be acquired by repeatedly scanning substantially the same site of the subject's eye.

In some embodiments, the data processor 223 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 223 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 223 is also included in the OCT image.

Further, the data processor 223 identifies the characteristic position corresponding to the characteristic site of the anterior segment, by analyzing each of the two photographic images substantially simultaneously obtained using the two or more anterior segment cameras, as described above. The data processor 223 calculates the three-dimensional position of the characteristic site (i.e., three-dimensional position of the subject's eye) by applying a known trigonometry to the positions of the two anterior segment cameras and the identified characteristic position corresponding to the characteristic site in the two photographic images. The calculated three-dimensional position can be used for the position matching of the optical system with respect to the subject's eye.

Furthermore, the ophthalmic apparatus 1 can measure the intraocular parameter(s) by performing OCT scan on the subject's left eye EL and the subject's right eye ER. Examples of the intraocular parameter include an axial length, a thickness of a predetermined layer region, a distance between predetermined sites, and the like.

In the first embodiment, the data processor 223 is assumed to calculate the axial length as the intraocular parameter calculator. In this case, the data processor 223 can calculate a distance between a position corresponding to the corneal apex and a position corresponding to Retinal Pigment Epithelium (hereinafter referred to as RPE) layer, as the axial length, based on the detection result of the interference light LC acquired by performing OCT scan. For example, the data processor 223 identifies the position of the corneal apex and the position of the RPE layer by identifying the positions of the local maximal values of the intensity of the interfering signal corresponding the detection result of the interference light LC, and the distance between the identified two positions as the axial length. For example, the data processor 223 performs segmentation processing on the OCT image formed based on the detection result of the interference light LC, identifies the position of the corneal apex and the position of the RPE layer from a plurality of identified layer regions, and calculates the distance between the identified two positions as the axial length.

(Display Unit 270, Operation Unit 280)

Upon receiving control of the controller 210, the display unit 270 displays information, as a user interface unit.

The operation unit 280 is used to operate the ophthalmic apparatus, as the user interface unit. The operation unit 280 includes various types of hardware keys (the joystick, buttons, switches, etc.) provided in the ophthalmic apparatus. Further, the operation unit 280 may include various kinds of software keys (buttons, icons, menus, etc.) displayed on the touch panel type display screen.

At least part of the display unit 270 and the operation unit 280 may be integrally configured. A typical example of this is the touch-panel display screen.

(Communication Unit 290)

The communication unit 290 has the function of communicating with an external device (not shown). The communication unit 290 includes a communication interface according to the mode of communication with the external device. Examples of the external device includes an eyeglass lens measurement device for measuring the optical properties of lenses. The eyeglass lens measurement device measures the power of the eyeglass lens worn by the subject, or the like and inputs the measurement data to the ophthalmic apparatus 1. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processor 9, for example.

The member and the mechanism for adjusting the optical axis of the OCT optical system 8 in any one of the first to third adjustment examples is an example of the "optical axis adjusting unit" according to the embodiments. The data processor 223 is an example of the "intraocular parameter calculator" according to the embodiments. The anterior segment cameras 15LA, 15LB, 15RA, 15RB, and 15LR are examples of the "two or more imaging units" according to the embodiments. The anterior segment camera 15LA is an example of the "first imaging unit" according to the embodiments. The anterior segment camera 15LR is an example of the "second imaging unit" according to the embodiments. The anterior segment camera 15RA is an example of the "third imaging unit" according to the embodiments. The refractometry projection system 6 and the refractometry light reception system 7 are an example of the "refractive power measurement optical system" according to the embodiments.

<Operation Example>

The operation of the ophthalmic apparatus 1 according to the first embodiment will be described.

Figure 12:
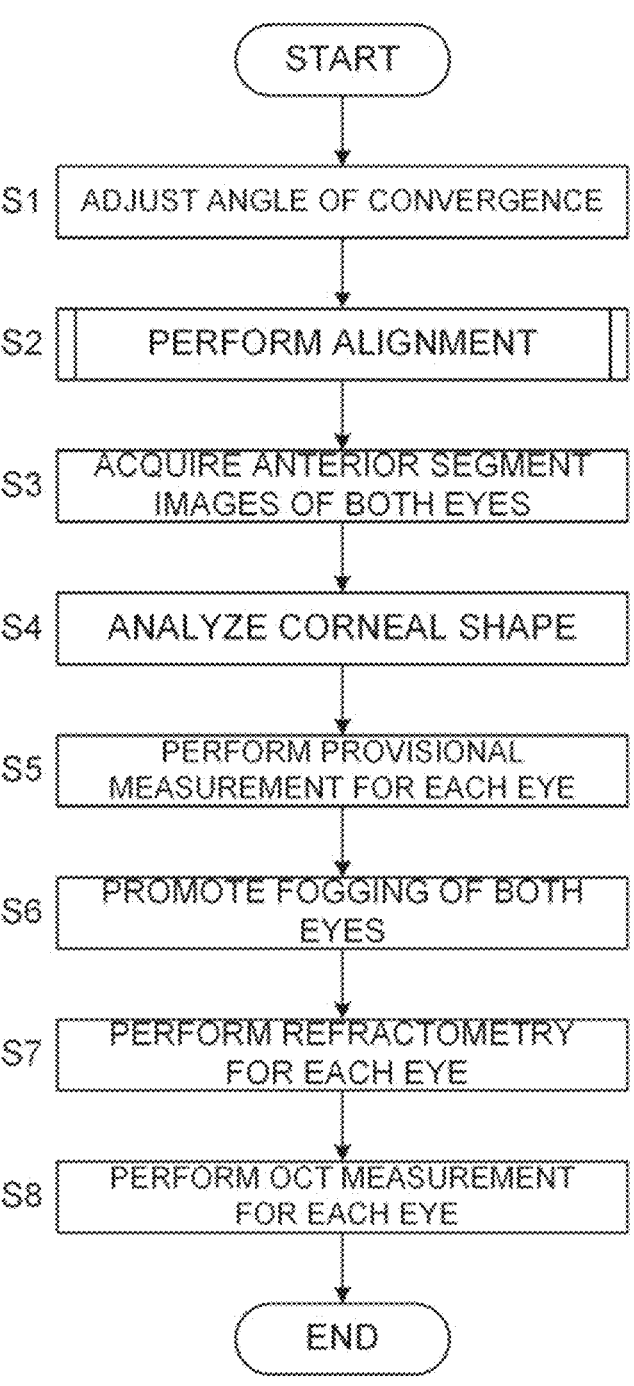
FIG. 12 is a schematic diagram illustrating a flow of an operation example of the ophthalmic apparatus according to the first embodiment.
Figure 13:
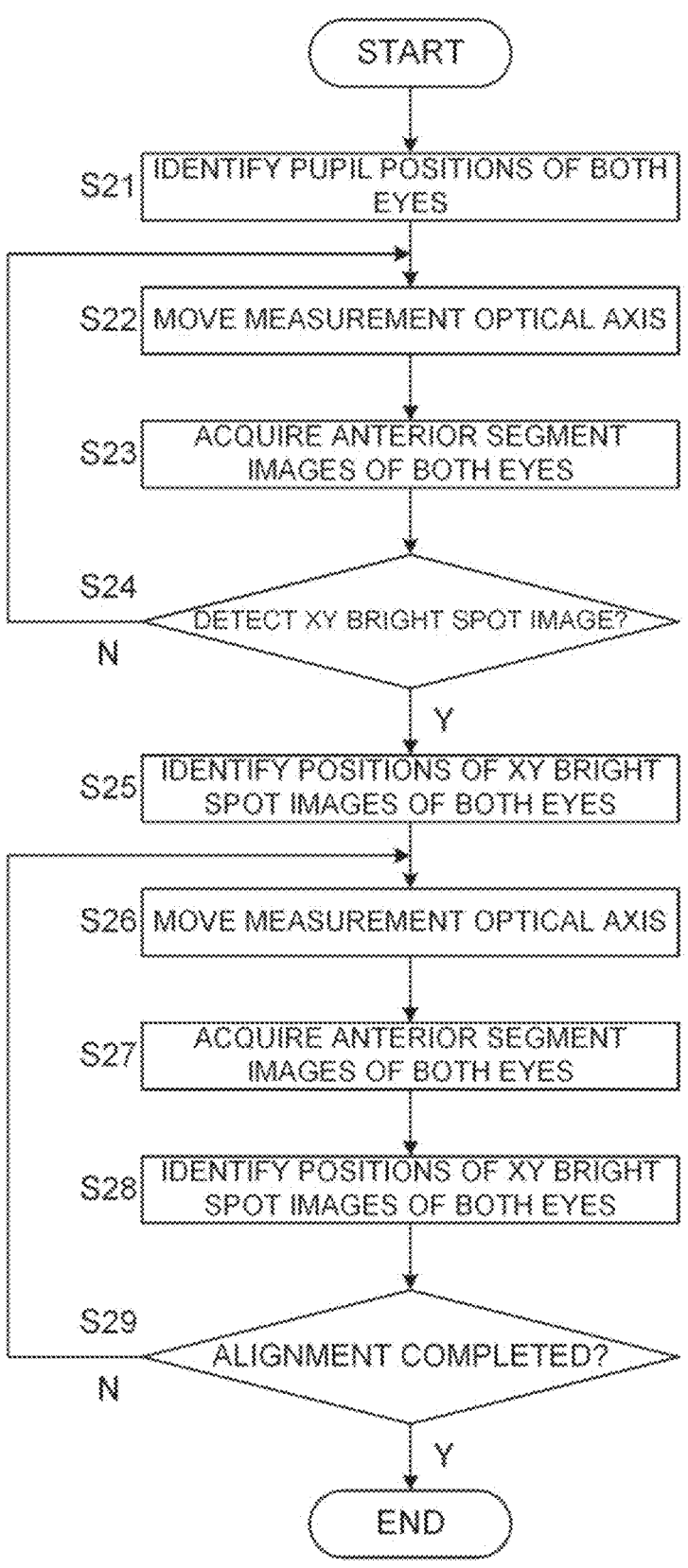
FIG. 13 is a schematic diagram illustrating a flow of an operation example of the ophthalmic apparatus according to the first embodiment.

FIGS. 12 and 13 illustrate examples of the operation of the ophthalmic apparatus 1. FIG. 12 shows a flowchart of an example of the operation of the ophthalmic apparatus 1 in the case of performing refractometry and OCT measurement sequentially. FIG. 13 shows a flow chart of an example of the operation of step S2 in FIG. 12. The storage unit 212 stores computer programs for realizing the processing shown in FIG. 12 and FIG. 13. The main controller 211 operates according to the computer programs, and thereby the main controller 211 performs the processing shown in FIG. 12 and FIG. 13.

Here, it is assumed that prior to the start of the flow shown in FIG. 12, it has been determined in advance to perform the inspection either in near vision state or far vision state.

(S1: Adjust Angle of Convergence)

First, the main controller 211 controls the movement mechanism 320 that rotates the dichroic mirrors ML and MR in accordance with the predetermined optotype distance corresponding to a near vision state or far vision state, and adjusts the angle of convergence.

The dichroic mirrors ML and MR change the deflection direction of the optical axes deflected by the optical axis switching member SW, as shown in FIG. 4.

(S2: Perform Alignment)

Subsequently, the main controller 211 performs alignment. The details of step S2 will be described below.

In step S2, the position matching of the measurement optical system 300 relative to the subject's left eye EL and the subject's right eye ER is performed.

(S3: Acquire Anterior Segment Images of Both Eyes)

Next, the main controller 211 controls the anterior segment observation system 5 to acquire the anterior segment images of both eyes.

Specifically, the main controller 211 controls the keratometry system 3 to turn the kerato-ring light source 32 on to project a ring-shaped light flux onto the cornea CLr of the subject's left eye EL. Subsequently, the main controller 211 controls the anterior segment illumination light source 50 to turn the anterior segment illumination light source 50 on to illuminate the anterior segment of the subject's left eye EL. After that, the main controller 211 captures the light receiving result of returning light of the illumination light on the imaging surface of the imaging element 59 to acquire the anterior segment image of the subject's left eye EL. Here, in the anterior segment image, the anterior segment of the subject's left eye EL with a superimposed kerato-ring image is depicted. Similarly, the main controller 211 controls the keratometry system 3 to turn the kerato-ring light source 32 on to project a ring-shaped light flux onto the cornea CRr of the subject's right eye ER. Subsequently, the main controller 211 controls the anterior segment illumination light source 50 to turn the anterior segment illumination light source 50 on to illuminate the anterior segment of the subject's right eye ER. After that, the main controller 211 captures the light receiving result of returning light of the illumination light on the imaging surface of the imaging element 59 to acquire the anterior segment image of the subject's right eye ER. Here, in the anterior segment image, the anterior segment of the subject's right eye ER with a superimposed kerato-ring image is depicted.

(S4: Analyze Corneal Shape)

Next, the main controller 211 controls the eye refractive power calculator 221 to analyze the anterior segment image of both eyes acquired in step S3. The eye refractive power calculator 221 identifies each of the kerato-ring images of the subject's left eye EL and the subject's right eye ER depicted in the anterior segment image, and calculates the corneal refractive power, the corneal astigmatism, and the corneal astigmatic axis angle from the identified kerato-ring image for each of the subject's left eye EL and the subject's right eye ER.

(S5: Perform Provisional Measurement for Each Eye)

Next, the main controller 211 performs provisional measurement for the refractometry for each eye. In the provisional measurement, a focusing state in the refractometry optical system is changed in accordance with the respective refractive powers of the subject's left eye EL and the subject's right eye ER. In the refractometry (main measurement), the respective refractive powers of the subject's left eye EL and the subject's right eye ER are measured while promoting the fogging of the subject's left eye EL and the subject's right eye ER with reference to the focusing state that are changed in the provisional measurement.

For example, each of the refractometry light source 61, and the focusing lenses 74 and 87 is moved in the optical axis direction and is arranged at a position corresponding to the refractive power of the subject's eye. First, the main controller 211 turns the refractometry light source 61 on and starts rotating the rotary prism 66.

Here, the provisional measurement is assumed to be performed on the subject's right eye ER after the provisional measurement is performed on the subject's left eye EL.

Next, the main controller 211 controls the refractometry optical system to project the ring-shaped measurement pattern light flux onto the subject's left eye EL. The ring image based on the returning light of the measurement pattern light flux from the subject's left eye EL is imaged on the imaging surface of the imaging element 59.

The main controller 211 determines whether or not the ring image based on the returning light from the fundus detected by the imaging element 59 has been acquired. For example, the main controller 211 detects a position (pixel) of the edge of the image that is formed based on the returning light detected by the imaging element 59, and determines whether or not the width (difference between outer diameter and inner diameter) of the image is greater than or equal to a predetermined value. Alternatively, the main controller 211 may determine whether or not the ring image has been acquired by determining whether or not a ring can be formed based on points (image) having a predetermined height (ring diameter) or more.

When it is determined that the ring image has been acquired, the eye refractive power calculator 221 analyzes the ring image based on the returning light of the measurement pattern light flux projected onto the subject's left eye EL by a known method and calculates a provisional spherical power S and a provisional astigmatic power C, for the subject's left eye EL.

Based on the obtained provisional spherical power S and the obtained provisional astigmatic power C, the main controller 211 moves the refractometry light source 61, the focusing lens 74, and the liquid crystal panel 41 to positions of the equivalent spherical power (S+C/2).

Once again, the main controller 211 causes the ring-shaped measurement pattern light flux to be projected onto the subject's left eye EL. The ring image based on the returning light of the measurement pattern light flux from the subject's left eye EL is imaged on the imaging surface of the imaging element 59. The main controller 211 determines whether or not the ring image based on the returning light from the fundus ELf detected by the imaging element 59 has been acquired.

When it is determined that the ring image has been acquired, the eye refractive power calculator 221 analyzes the ring image based on the returning light of the measurement pattern light flux projected onto the subject's left eye EL by a known method and calculates a provisional spherical power S and a provisional astigmatic power C, for the subject's left eye EL.

Subsequently, for the subject's right eye ER, a provisional spherical power S and a provisional astigmatism power C are obtained in the same way. In this case, as described above, the optical axis of the refractometry optical system is switched by the optical axis switching member SW.

The main controller 211 controls the eye refractive power calculator 221 to calculate an intermediate power position of the subject's left eye EL and the subject's right eye ER. For example, the intermediate power position may be a position corresponding to an intermediate power ((ESR+ESL)/2) between the equivalent spherical power ESL of the subject's left eye EL and the equivalent spherical power ESR of the subject's right eye ER.

The main controller 211 moves the refractometry light source 61, the focusing lens 74, and the liquid crystal panel 41 to the positions of the intermediate power. The moved position is a position corresponding to the provisional far point.

In some embodiments, without obtaining the intermediate power position, the main controller 211 moves the refractometry light source 61, the focusing lens 74, and the liquid crystal panel 41 to positions corresponding to the equivalent spherical powers, in the provisional measurement of each of the subject's left eye EL and the subject's right eye ER.

(S6: Promote Fogging of Both Eyes)

Next, the main controller 211 promotes the fogging of both eyes by further moving the liquid crystal panel 41 from the position obtained in the provisional measurement in step S5 to the fogging position.

(S7: Perform Eye Refractometry for Each Eye)

Subsequently, the main controller 211 performs refractometry for each eye.

Here, the refractometry is assumed to be performed on the subject's right eye ER after the refractometry is performed on the subject's left eye EL.

Specifically, the main controller 211 turns the refractometry light source 61 on, in case that the refractometry light source 61 has been off. In addition, in case that the rotation of the rotary prism 66 has been stopped, the main controller 211 starts rotating the rotary prism 66. When measuring in the far vision state, the fixation target is at a position corresponding to the far point obtained in step S5, as described above. When measuring in the near vision state, the fixation target is at a predetermined fixed position.

The main controller 211 controls the refractometry projection system 6 and the refractometry light reception system 7 to acquire the ring image, similar to the provisional measurement in step S5. In other words, the refractometry optical system projects the measurement pattern light flux for the subject's left eye so that the position corresponding to the intermediate power between the refractive power of the subject's left eye EL and the refractive power of the subject's right eye ER becomes the focal position, and acquires the ring image. The main controller 211 controls the eye refractive power calculator 221 to calculate a spherical power, an astigmatic power, and an astigmatic axis angle from the analysis result obtained of the ring image and the movement amount of the focusing lens 74. The calculated spherical power, the astigmatic power, and the astigmatic axis angle are stored in the storage unit 212.

Subsequently, for the subject's right eye ER, the refractometry is performed in the same way. In this case, as described above, the optical axis of the refractometry optical system is switched by the optical axis switching member SW.

In other words, the refractometry optical system is configured to project the measurement pattern light flux along the measurement optical axis OL onto the subject's left eye EL via the objective lens 51, to project the measurement pattern light flux along the measurement optical axis OR onto the subject's right eye ER via the objective lens 51, and to detect the returning light of the measurement pattern light flux from the subject's left eye EL and the returning light of the measurement pattern light flux from the subject's right eye ER. The eye refractive power calculator 221 calculates the refractive power of the subject's left eye EL based on the light receiving result of the returning light of the measurement pattern light flux from the subject's left eye EL, and calculates the refractive power of the subject's right eye ER based on the light receiving result of the returning light of the measurement pattern light flux from the subject's right eye ER.

In some embodiments, in step S7, acquisition of the anterior segment images in step S3 and analysis of the corneal shape in step S4 are performed simultaneously. In some embodiments, alignment in step S2 is performed before proceeding to step S8.

(S8: Perform OCT Measurement for Each Eye)

Subsequently, the main controller 211 controls the OCT optical system 8 to perform OCT measurement for each eye.

Here, the OCT measurement is assumed to be performed on the subject's right eye ER after the OCT measurement is performed on the subject's left eye EL.

For example, the main controller 211 causes the fixation target for OCT measurement to be presented to the subject's left eye EL, and controls the OCT optical system 8 to perform OCT provisional measurement to acquire a tomographic image for adjustment for adjusting a reference position of the measurement range in the depth direction. Specifically, the main controller 211 controls the optical scanner 88 to deflect the measurement light LS having been generated based on the light L0 emitted from the light source unit 101 to scan a predetermined site (for example, fundus) of the subject's left eye EL with the deflected measurement light LS. The detection result of the interference light LC obtained by scanning with the measurement light LS is fed to the image forming unit 222. The image forming unit 222 forms a tomographic image (OCT image) of the subject's left eye EL from the obtained interference signal.

Subsequently, the main controller 211 adjusts the reference position of the measurement range in the depth direction (Z direction). For example, the main controller 211 controls the data processor 223 to identify a predetermined site (for example, sclera) in the obtained tomographic image, and sets a position separated by a predetermined distance in the depth direction from the identified position of the predetermined site as the reference position of the measurement range. Alternatively, a predetermined position determined in advance so that the optical path lengths of the measurement light LS and the reference light LR substantially coincide may be set as the reference position of the measurement range.

Next, the main controller 211 performs control of adjusting focusing and of adjusting polarization. For example, the main controller 211 controls the OCT unit 100 to perform OCT measurement, after moving the focusing lens 87 by a predetermined distance.

The main controller 211 controls the data processor 223 to determine the focus state of the measurement light LS based on the detection result of the interference light acquired by the OCT measurement. For example, the data processor 223 calculates a predetermined evaluation value for the image quality of the OCT image, and determines whether or not the calculated evaluation value is equal to or less than a threshold. In some embodiments, the focus adjustment is continued until the calculated evaluation value becomes equal to or less than the threshold. That is, when the evaluation value is equal to or less than the threshold, it is determined that the focus state of the measurement light LS is appropriate. And the focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements as described above. In addition, while performing this monitoring process, the focusing lens 87 is moved to find the position of the focusing lens 87 in which the interference intensity is maximized. With the focus adjustment thus performed, the focusing lens 87 can be guided to the position where the interference intensity is optimized.

Further, the data processor 223 determines the polarization state of at least one of the measurement light LS and the reference light LR by analyzing the detection result of the interference light obtained by the OCT measurement.

For example, the main controller 211 performs repetitive OCT measurements while controlling the polarization controller 106 according to a predetermined algorithm. In some embodiments, the main controller 211 controls the attenuator 105 to change an attenuation of the reference light LR. The data processor 223 analyzes the detection results of the interference light LC repeatedly acquired by the OCT measurements to calculate predetermined evaluation values relating to the image quality of OCT images and to determine whether or not the calculated evaluation value is equal to or less the threshold. The threshold is set in advance. Polarization adjustment is continued until the calculated evaluation value becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

When the adjustment of the position in the depth direction, the focus adjustment, and the polarization adjustment are completed, the main controller 211 controls the optical scanner 88 to scan a predetermined site of the fundus of the subject's left eye EL with the measurement light LS. For example, the detection signal obtained by scanning with the measurement light LS is fed to the image forming unit 222. The image forming unit 222 forms a tomographic image of the fundus based on the obtained detection signal.

Subsequently, for the subject's right eye ER, the OCT measurement is performed in the same way. In this case, as described above, the optical axis of the OCT optical system 8 is switched by the optical axis switching member SW.

In some embodiments, before performing OCT measurement using the measurement light LS on one of the subject's left eye EL and the subject's right eye ER, the main controller 211 controls the OCT optical system 8 to adjust the optical path length of the reference optical path based on the axial length and the refractive power of another of the subject's left eye EL and subject's right eye ER. In other words, in light of the fact that the optical path length of the reference optical path, which is one of the measurement environments for OCT measurement, can be associated with the axial length and the refractive power of the subject's eye, and that the optical path length of the reference optical path is often almost the same in the left and right eye, from the optical path length of the reference optical path at the time of OCT measurement for one of the subject's eyes performed first, the optical path length of the reference optical path at the time of OCT measurement for another of the subject's eyes to be performed next is identified from the axis length and the refractive power of the another of the subject's eyes, and is adjusted to the identified optical path length. This allows to significantly reduce the time required for OCT measurements for both eyes.

For each of the subject's left eye EL and the subject's right eye ER, the main controller 211 controls the data processor 223 to calculate the distance between the position corresponding to the corneal apex and the position corresponding to the RPE layer as the axial length, based on the obtained detection signal or the obtained tomographic image. The data processor 223 can calculate the intraocular parameter other than the axial length. For example, the main controller 211 controls the OCT optical system 8 to scan the fundus or the cornea (anterior segment) sequentially or simultaneously. The main controller 211 controls the data processor 223 to calculate the distance between the position corresponding to the corneal apex and the position corresponding to the RPE layer as the axial length, based on the detection signal or the tomographic image obtained by scanning the cornea and the detection signal or the tomographic image obtained by scanning the fundus. A method for calculating such an axis length is disclosed in Japanese Unexamined Patent Application Publication No. 2020-044027, for example.

This terminates the operation of the ophthalmic apparatus 1 (END).

In some embodiments, after performing steps S1 to S8 for one of the far vision and the near vision, by performing steps S1 to S8 for the other of the far vision and the near vision, the inspection is performed in both the far vision and the near vision.

Step S2 in FIG. 12 is performed as shown in FIG. 13.
(S21: Identify Pupil Positions of Both Eyes)

First, the main controller 211 identifies the characteristics positions of both eyes from the photographic images obtained by controlling the anterior segment cameras 15LA, 15RA, 15LB, 15 RB. In the present embodiment, the pupil position is identified as the characteristic position.

Specifically, the main controller 211 controls the anterior segment cameras 15LA and 15LB to substantially simultaneously photograph the subject's left eye EL from different directions, and to obtain two photographic images (anterior segment images). In the same manner, the main controller 211 controls the anterior segment cameras 15RA and 15RB to substantially simultaneously photograph the subject's right eye ER from different directions, and to obtain two photographic images. In some embodiments, the two photographic images of the subject's left eye EL and the two photographic images of the subject's right eye ER are photographed substantially simultaneously.

The process of identifying the pupil position of the subject's right eye ER is the same as the process of identifying the pupil position of the subject's left eye EL. In the following, the process of identifying the pupil position of the subject's left eye EL will be mainly described.

The main controller 211 controls the data processor 223 that functions as a characteristic position identifying unit, to analyze the two photographic images obtained by the anterior segment cameras 15LA and 15LB and to identify the pupil position (pupil center position or position of the center of gravity of pupil) of the subject's left eye EL.

In this case, for each of the photographic images, the data processor 223 identifies an image region (pupil region) corresponding to the pupil based on the distribution of pixel values (luminance values etc.). Generally, the pupil is represented with lower luminance compared to other sites, and therefore, the pupil region may be identified by searching an image region with low luminance. At this time, the pupil region may be identified by taking the shape of the pupil into consideration. That is, it is possible to configure such that the pupil region is identified by searching for a substantially circular image region with low luminance.

Next, the data processor 223 identifies the center position of the identified pupil region. As described above, the pupil is substantially circular; therefore, it is possible to identify the contour of the pupil region, to identify the center position of this contour (an approximate circle or an approximate ellipse thereof), and to treat this as the pupil center position. Instead, by obtaining the center of gravity of the pupil region, this position may be used as the position of the center of gravity of the pupil.

The data processor 223 can sequentially identify the characteristic position for the photographic images sequentially obtained by the anterior segment cameras 15LA and 15LB. Moreover, the data processor 223 may identify the pupil position every one or more arbitrary number of frames for the photographic images sequentially obtained by the anterior segment cameras 15LA and 15LB.

Subsequently, the data processor 223, as a three-dimensional position calculator, identifies the three-dimensional position of the characteristic position as the three-dimensional position of the subject's eye, based on the positions of the anterior segment cameras 15LA and 15LB and the identified pupil positions. For example, the data processor 223 calculates the three-dimensional position of the subject's eye by applying a known trigonometry to the positions of the two anterior segment cameras 15LA and 15LB (these are known) and the pupil positions in the two photographic images, as disclosed in Japanese Unexamined Patent Application Publication No. 2013-248376.

The pupil position of the subject's right eye ER can also be identified by the same process as above.
(S22: Move Measurement Optical Axis)

The main controller 211 controls the movement of the measurement optical system 300, the adjustment of the pupillary distance using the optical axis switching member SW, and the positions of the fixation targets presented by the fixation projection systems 4L and 4R, based on the pupil positions of both eyes identified in step S21.

Specifically, the pupillary distance is identified from the pupil positions of both eyes identified in step S21. For example, the main controller 211 adjusts at least one of the movement mechanism 200, the movement mechanism 310, or the fixation projection systems 4L and 4R, so that the pupil positions of both eyes identified in step S21 are closest to (i.e., coincide with) each of the known measurement optical axes OL and OR. The main controller 211 can change the relative position of the measurement optical system 300 relative to the subject's left eye EL and the subject's right eye ER, by controlling the movement mechanism 200. The main controller 211 can move the optical axis switching member SW to change the distance between the measurement optical axis OL and the measurement optical axis OR, by controlling the movement mechanism 310. The main controller 211 can change the fixation position (presented position of the fixation target) of each of the subject's left eye EL and the subject's right eye ER, by controlling the fixation projection systems 4L and 4R.

As a result, the position of the subject's left eye EL in the X and Y directions is adjusted so as to approximately coincide with the position of the measurement optical axis OL in the X and Y directions, and the distance in the Z direction is adjusted to a predetermined working distance.

In some embodiments, the main controller 211 determines whether or not the arrangement direction of the subject's left eye EL and the subject's right eye ER is parallel to the X direction (i.e., whether or not the heights of both eyes are misaligned), based on the pupil positions of both eyes identified in step S21. In this case, the main controller 211 can change at least one of the deflection direction of the optical axis switching member SW, or the deflection directions of the dichroic mirrors ML and MR, by controlling the movement mechanisms 310 and 320 based on the pupil positions of both eyes identified in step S21.

In some embodiments, when it is determined that the arrangement direction of the subject's left eye EL and the subject's right eye ER is not parallel to the X direction, the main controller 211 can control the display unit 270 to prompt the subject to tilt his or her face. The main controller 211 may prompt the subject to tilt his or her face by outputting sound.

(S23: Acquire Anterior Segment Images of Both Eyes)

Subsequently, the main controller 211 turns the XY alignment light source 21 on, and then controls the anterior segment cameras 15LA, 15RA, 15LB, and 15RB again to acquire the anterior segment images of both eyes in which the XY bright spot images based on the reflected light from the XY alignment light source 21 are depicted.

(S24: Detect XY Bright Spot Image?)

Next, the main controller 211 controls the data processor 223 to detect the XY bright spot images for the anterior segment images of both eyes acquired in step S23.

For example, the data processor 223 detects whether or not the XY bright spot images are depicted based on pixel values, for each of the two anterior segment images of the subject's left eye EL and the two anterior segment images of the subject's right eye ER. When it is detected by the data processor 223 that the XY bright spot images are depicted in all of the above four anterior segment images (S24: Y), the operation of the ophthalmic apparatus 1 proceeds to step S25. When it is detected by the data processor 223 that the XY bright spot image is not depicted in at least one of the above four anterior segment images (S24: N), the operation of the ophthalmic apparatus 1 proceeds to step S22.

(S25: Identify Positions of XY Bright Spot Images of Both Eyes)

When the XY bright spot images are detected in the anterior segment images of both eyes in step S24 (S24: Y), the main controller 211 controls the data processor 223 to identify the positions of the XY bright spot images of both eyes detected in step S24. In step S25, the same identification process as in step S21 is used to identify the positions of the XY bright spot images. In other words, instead of the pupil positions of both eyes identified in step S21, the positions of the XY bright spot images are identified in step S25.

(S26: Move Measurement Optical Axis)

The main controller 211 controls the movement of the measurement optical system 300, the adjustment of the pupillary distance using the optical axis switching member SW shown in FIG. 3, and the positions of the fixation targets presented by the fixation projection systems 4L and 4R, based on the positions of the XY bright spot images of both eyes identified in step S25.

In the step S26, the adjustment of the measurement optical axes is performed in the same manner as in step S22.

(S27: Acquire Anterior Segment Images of Both Eyes)

Subsequently, the main controller 211 controls the anterior segment cameras 15LA, 15RA, 15LB, and 15RB to acquire the anterior segment images of both eyes.

(S28: Identify Positions of XY Bright Spot Images of Both Eyes)

Next, the main controller 211 controls the data processor 223 to identify the positions of the XY bright spot images from the anterior segment images of both eyes acquired in step S27, in the same way as in step S25.

(S29: Alignment Completed?)

Next, the main controller 211 determine whether or not the respective positions of the XY bright spot images of both eyes identified in step S28 are within predetermined alignment completion ranges.

When it is determined that the respective positions of the XY bright spot images of both eyes are within the predetermined alignment completion ranges (S29: Y), the processing of step S2 in FIG. 12 is terminated (END). When it is determined that at least one of the positions of the XY bright spot images of both eyes is not within the predetermined alignment completion ranges (S29: N), the operation of the ophthalmic apparatus 1 proceeds to step S26.

As described above, in step S2 of FIG. 12, the main controller 211 is configured to change the relative position of the OCT optical system 8 relative to the subject's left eye EL and the subject's right eye ER, and to change the orientation of the measurement optical axis OL, the orientation of the measurement optical axis OR, and the distance between the measurement optical axes OL and OR so that the measurement optical axis OL coincides with a visual axis of the subject's left eye EL and the measurement optical axis OR coincides with a visual axis of the subject's right eye ER, based on two or more images obtained by the two or more anterior segment units.

As explained above, according to the first embodiment, the optical axis of the measurement optical system 300 (specifically, the optical axis of the OCT optical system 8, the optical axis of the refractometry optical system coaxially coupled with the optical axis of the OCT optical system 8) is switched so as to approximately coincide with the any one of the measurement optical axes OL and OR located at a distance from each other, using the optical axis switching member SW. Thereby, the OCT measurement can be performed on both eyes in sequence with both eyes open. This allows to provide an ophthalmic apparatus capable of measuring characteristics of both eyes with high precision and space saved at low cost. In particular, it is possible to reduce the size and cost of the optical system of the ophthalmic apparatus capable of performing OCT measurements on both eyes.

Second Embodiment

In the first embodiment, the case has been described in which the fixation projection systems 4L and 4R are provided in the transmission direction of the dichroic mirrors ML and MR. However, the configuration of the ophthalmic apparatus according to the embodiments is not limited thereto. For example, the measurement optical system may include a common fixation projection system for both eyes.

In the following, the ophthalmic apparatus according to a second embodiment will be described focusing on differences from the ophthalmic apparatus 1 according to the first embodiment.

Figure 14:
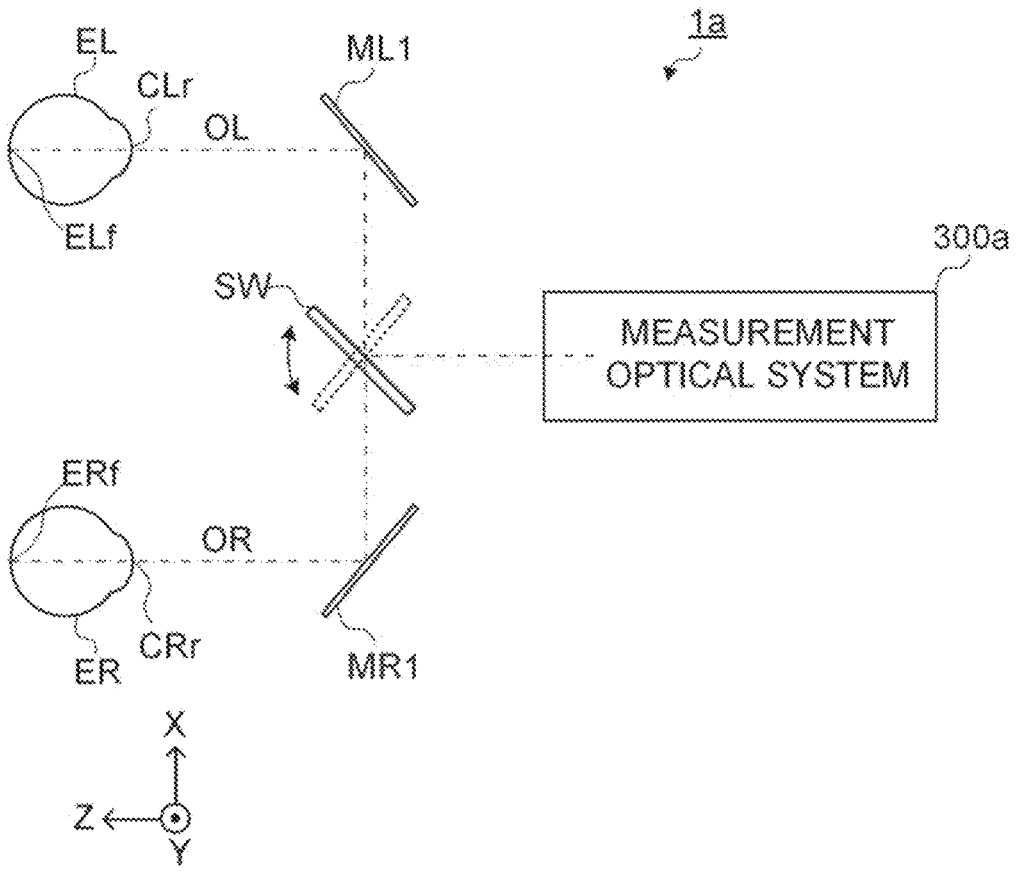
FIG. 14 is a schematic diagram illustrating an example of a configuration of the optical system of the ophthalmic apparatus according to a second embodiment.
Figure 15:
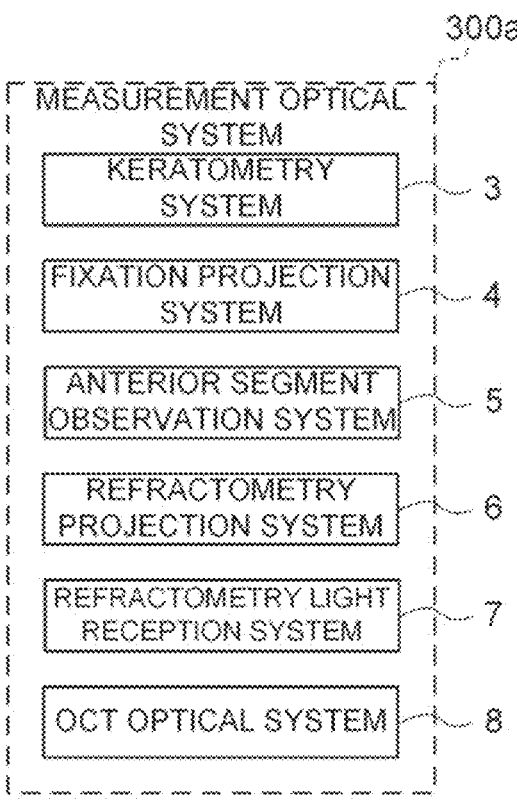
FIG. 15 is a schematic diagram illustrating an example of a configuration of the optical system of the ophthalmic apparatus according to the second embodiment.

FIGS. 14 and 15 show examples of a configuration of an optical system of the ophthalmic apparatus according to the second embodiment. FIG. 14 schematically shows the configuration of the optical system of the ophthalmic apparatus according to the second embodiment when viewed from the upper side, as in FIG. 1. FIG. 15 shows a functional block diagram representing a configuration example of a measurement optical system 300a in FIG. 14.

The difference between the configuration of the ophthalmic apparatus 1a according to the second embodiment and the configuration of the ophthalmic apparatus 1 according to the first embodiment is mainly that a reflective mirror ML1 is provided instead of the dichroic mirror ML, that a reflective mirror MR1 is provided instead of the dichroic mirror MR, and that the measurement optical system 300a is provided instead of the measurement optical system 300 and the fixation projection systems 4L and 4R.

The reflective mirror ML1 deflects the measurement optical axis OL deflected by the optical axis switching member SW toward the subject's left eye EL. The reflective mirror MR1 deflects the measurement optical axis OR deflected by the optical axis switching member SW toward the subject's right eye ER.

As shown in FIG. 15, the measurement optical system 300a includes the keratometry system 3, the fixation projection system 4, the anterior segment observation system 5, the refractometry projection system 6, the refractometry light reception system 7, and the OCT optical system 8.

Similar to the ophthalmic apparatus 1, the ophthalmic apparatus 1a also includes the optical axis adjusting unit, the pupillary distance adjusting unit, and the angle of convergence adjusting unit.

Figure 16:
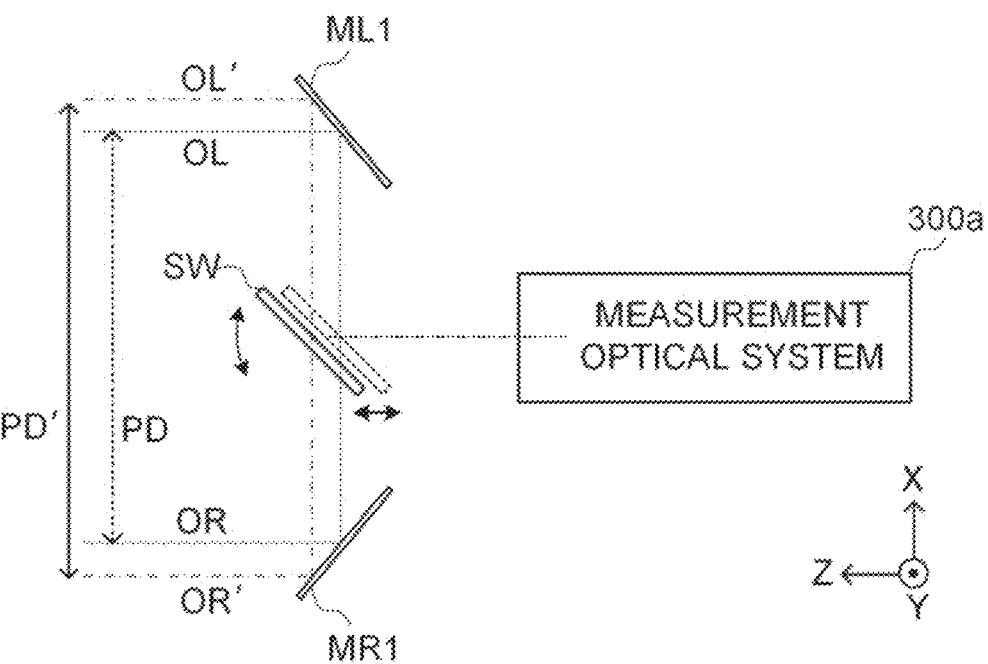
FIG. 16 is a schematic diagram for explaining the optical system of the ophthalmic apparatus according to the second embodiment.

FIG. 16 shows a diagram describing an example of the operation of the ophthalmic apparatus 1a according to the second embodiment. In FIG. 16, like reference numerals designate like parts as in FIG. 3 or FIG. 14. The same description may not be repeated.

As in the first embodiment, the pupillary distance adjusting unit changes the distance in the X direction between the measurement optical axes OL and OR, by moving the optical axis switching member SW along the measurement optical axis OL or the measurement optical axis OR (Z direction, optical axis of the measurement optical system 300a). As shown in FIG. 16, this changes positions of the optical axes deflected by the reflective mirrors ML1 and MR1, the measurement optical axis OL becomes the measurement optical axis OL', and the measurement optical axis OR becomes the measurement optical axis OR'. As a result, the distance in the X direction between the measurement optical axes OL' and OR' becomes the pupillary distance PD'. That is, the pupillary distance is changed.

In some embodiments, the pupillary distance is changed by moving the optical axis switching member SW in the X direction shown in FIG. 16.

In some embodiments, the optical axis switching member SW is moved by a movement mechanism (not shown) under the control from the controller described below. In this case, the function of the pupillary distance adjusting unit is realized by a controller and a movement mechanism not shown in the figure. In some embodiments, the optical axis switching member SW is manually moved by the movement mechanism not shown in the figure. In this case, the function of the pupillary distance adjusting unit is realized by the movement mechanism not shown in the figure.

Figure 17:
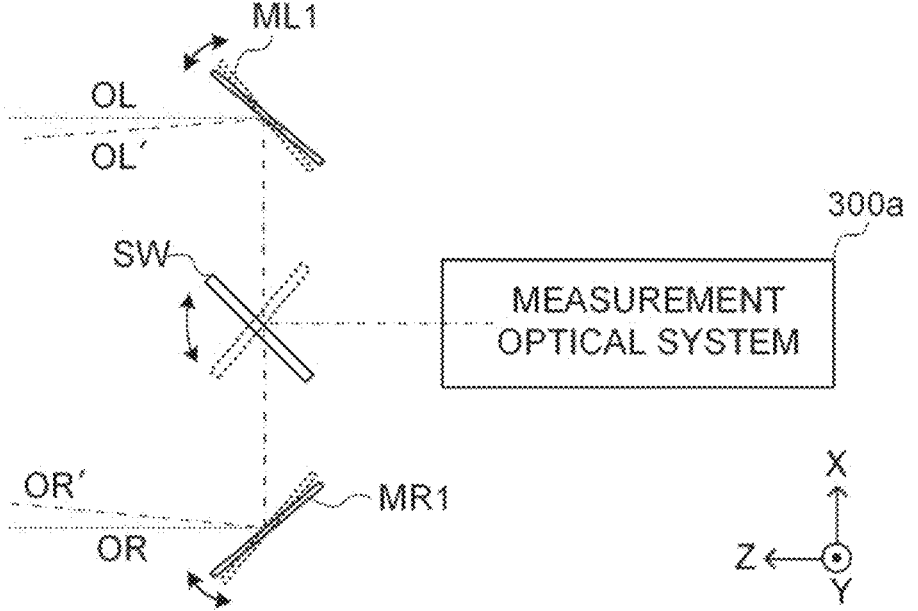
FIG. 17 is a schematic diagram for explaining the optical system of the ophthalmic apparatus according to the second embodiment.

FIG. 17 shows a diagram describing an example of the operation of the angle of convergence adjusting unit in the ophthalmic apparatus 1a according to the second embodiment. In FIG. 17, like reference numerals designate like parts as in FIG. 4 or FIG. 14. The same description may not be repeated.

As in the first embodiment, the angle of convergence adjusting unit changes at least one of the measurement optical axis OL or the measurement optical axis OR, by changing at least one of an orientation of the reflective mirror ML1 or an orientation of the reflective mirror MR1.

For example, the deflection surface of the reflective mirror ML1 is configured to be rotatable around a rotary axis extending in the Y axis direction. For example, the deflection surface of the reflective mirror MR1 is configured to be rotatable around a rotary axis extending in the Y axis direction. Thereby, as shown in FIG. 17, the measurement optical axis OL deflected by the reflective mirror ML1 becomes the measurement optical axis OL', and the measurement optical axis OR becomes the measurement optical axis OR'. That is, the angle of convergence is changed.

In some embodiments, the reflective mirrors ML1 and MR1 are rotated by a movement mechanism (rotary mechanism) not shown in the figure, under the control from the controller described below. In this case, the function of the angle of convergence adjusting unit is realized by the controller and the movement mechanism not controller and shown in the figure. In some embodiments, the reflective mirrors ML1 and MR1 are manually rotated by the movement mechanism (rotary mechanism) not shown in the figure. In this case, the function of the angle of convergence adjusting unit is realized by the movement mechanism not shown in the figure.

Figure 18:
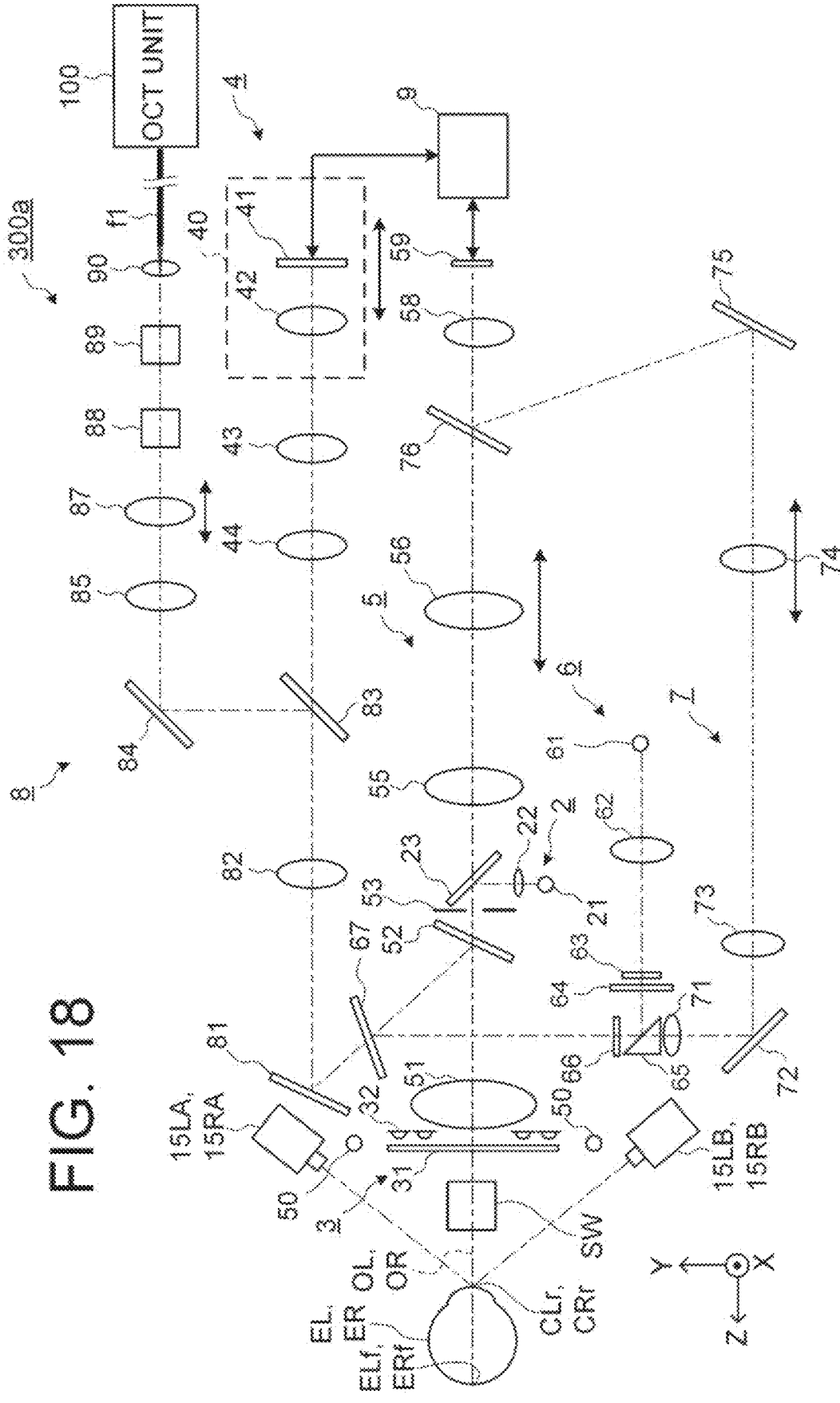
FIG. 18 is a schematic diagram illustrating an example of a configuration of the optical system of the ophthalmic apparatus according to the second embodiment.

FIG. 18 shows an example of the configuration of the measurement optical system 300a according to the second embodiment. FIG. 18 schematically shows an example of the configuration of the measurement optical system 300a when viewed from the lateral side (X direction), as in FIG. 5. In FIG. 18, like reference numerals designate like parts as in FIG. 5 or FIG. 14. The same description may not be repeated.

The difference between the configuration of the measurement optical system 300a and the configuration of the measurement optical system 300 is that a dichroic mirror 83, a reflective mirror 84, and the fixation projection system 4 are provided between the relay lens 82 and the relay lens 85, and that an optical path of the fixation projection system 4 is coaxially coupled with the optical path of the OCT optical system 8 by the dichroic mirror 83.

The dichroic mirror 83 transmits light with wavelength components in the visible region, and reflects light with wavelength components in the near-infrared (or infrared) region. As described above, the fixation projection system 4 is positioned in the transmission direction of the dichroic mirror 83, and the OCT optical system 8 is positioned in the reflection direction of the dichroic mirror 83. Specifically, the dichroic mirror 83 is placed between the relay lens 82 and the fixation projection system 4, and the reflective mirror 84 is placed between the dichroic mirror 83 and the OCT optical system 8.

The fixation projection system 4 presents fixation target(s) to the subject's left eye EL or the subject's right eye ER on the measurement optical axis by projecting the fixation light flux onto the fundus ELf of the subject's left eye EL or the fundus ERf of the subject's right eye ER. Here, the measurement optical axis is coaxially coupled with the optical axis of the objective lens 51 (measurement optical system 300a). The fixation projection system 4 includes a fixation unit 40 and relay lenses 43 and 44. The fixation unit 40 includes a liquid crystal panel 41 and a relay lens 42. The liquid crystal panel 41 displays a pattern representing a fixation target under the control from the controller. By changing the display position of the fixation target on the screen of the liquid crystal panel 41, the fixation position of the subject's left eye EL or the subject's right eye ER can be changed. Further, the fixation unit 40 is movable along an optical axis under the control from the controller.

Light from the liquid crystal panel 41 passes through the relay lenses 42, 43, and 44, is transmitted through the dichroic mirror 83, and is projected onto the subject's eye in the same path as the measurement light LS from OCT optical system 8.

In some embodiments, the fixation unit 40 can be moved in the optical axis direction independently of the relay lenses 43 and 44.

Also, in the second embodiment, the optical axis of the OCT optical system 8 can be adjusted as in the first embodiment. For example, by using the reflective mirror 84 as the deflection member DF1 and the dichroic mirror 83 as the deflection member DF2, the optical axis of the OCT optical system 8 can be adjusted as shown in the first adjustment example in FIG. 9A. Also, in the second embodiment, the optical axis of the OCT optical system 8 can be adjusted, as shown in the second adjustment example in FIG. 9B. In addition, in the third adjustment example, where the deflection direction of the optical axis of the OCT optical system 8 is changed by optical member in the path of the measurement light, the reflective mirror 81, the dichroic mirror 52, the dichroic mirror 83, the reflective mirror 84, which are shown in FIG. 18, or a reflective mirror not shown in the figure can be used as an example of the optical member.

The fixation projection system 4 is an example of the "fixation optical system" according to the embodiments. The dichroic mirror 83 is an example of the "optical path coupling member" according to the embodiments. The reflective mirror ML1 is an example of the "first reflection member" according to the embodiments. The reflective mirror MR1 is an example of the "second reflection member" according to the embodiments. The angle of convergence adjusting unit is an example of the "first adjustment unit" according to the embodiments. The movement mechanism for rotating the deflection surface of the optical axis switching member SW, the deflection surface of the reflective mirror ML1, and the deflection surface of reflective mirror MR1 is an example of the "second adjustment unit" according to the embodiments.

Figure 19:
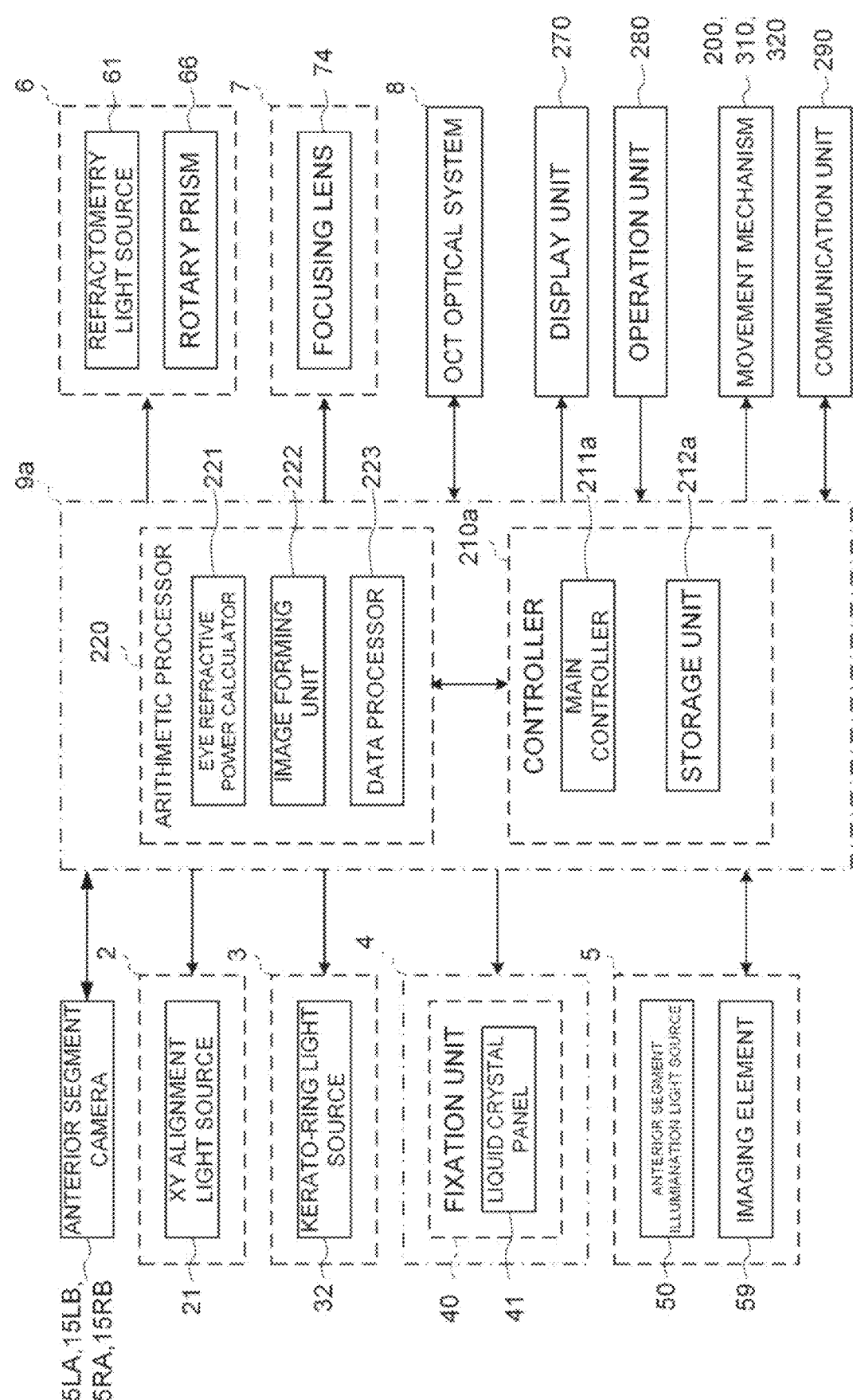
FIG. 19 is a schematic diagram illustrating an example of a configuration of a processing system of the ophthalmic apparatus according to the second embodiment.

FIG. 19 shows an example of a functional configuration of a processing system of the ophthalmic apparatus 1a according to the second embodiment. FIG. 19 shows an example of a functional block diagram illustrating the processing system of the ophthalmic apparatus 1a. In FIG. 19, like reference numerals designate like parts as in FIG. 10 or FIG. 18. The same description may not be repeated.

The difference between the configuration of the processing system of the ophthalmic apparatus 1a and the configuration of the processing system of the ophthalmic apparatus 1 shown in FIG. 10 is that the fixation projection system 4 is provided in place of the fixation projection systems 4L and 4R, and that a processor 9a is provided in place of the processor 9.

The difference between the configuration of the processor 9a and the configuration of the processor 9 shown in FIG. 10 is that a controller 210a is provided in place of the controller 210. The controller 210a includes a main controller 211a and a storage unit 212a. The main controller 211a can perform the same control as the main controller 211, except that the main controller 211a controls the fixation projection system 4 instead of the control for the fixation projection systems 4L and 4R by the main controller 211. The storage unit 212a stores the same programs as the storage unit 212, except the program using for controlling the fixation projection systems 4L and 4R.

The operation of the ophthalmic apparatus 1a according to the second embodiment is almost the same as that of the ophthalmic apparatus 1 according to the first embodiment shown in FIG. 12 and FIG. 13, except for the control for the fixation projection system 4.

In the second embodiment, the OCT measurement can be performed on one eye at a time in sequence in a state where the same fixation target is presented to both eyes with both eyes open.

Specifically, instead of the control performed by the main controller 211 in which the fixation target is independently presented to the subject's left eye EL and the subject's right eye ER by the fixation projection systems 4L and 4R, the main controller 211a controls the fixation projection system 4 so as to present the same fixation target to the subject's left eye EL and the subject's right eye ER.

For example, when the inspection is performed in the far vision state in step S7 of FIG. 12, the main controller 211a presents the fixation target to both eyes from a position corresponding to the provisional spherical power S and the provisional astigmatism power C (or equivalent spherical power) on the more plus side (far vision side) among the provisional spherical power S and the provisional astigmatic power C (or equivalent spherical power) of the subject's left eye EL and the provisional spherical power S and the provisional astigmatic power C (or equivalent spherical power) of the subject's right eye ER which are obtained in step S5 of FIG. 12.

For example, when the inspection is performed in the near vision state in step S7 of FIG. 12, the main controller 211a presents the fixation target to both eyes from the same position as in the case of inspection in the far vision state. In some embodiments, in case that the subject is monovision, the main controller 211a presents the fixation target to both eyes from a position corresponding to the provisional spherical power S and the provisional astigmatism power C (or equivalent spherical power) on the more minus side (near vision side) among the provisional spherical power S and the provisional astigmatic power C (or equivalent spherical power) of the subject's left eye EL and the provisional spherical power S and the provisional astigmatic power C (or equivalent spherical power) of the subject's right eye ER which are obtained in step S5 of FIG. 12. At this time, the main controller 211a can, if necessary, control the reflective mirrors ML1 and MR1 to adjust the angle of convergence.

It should be noted that as in step S22 of FIG. 13, the main controller 211a determines whether or not the arrangement direction of the subject's left eye EL and the subject's right eye ER is parallel to the X direction (i.e., whether or not the heights of both eyes are misaligned), based on the pupil positions of both eyes identified in step S21. In this case, the main controller 211a can adjust the arrangement direction of the measurement optical axes OL and OR as the second adjustment unit, by changing the deflection direction of the reflective mirror ML1, the deflection direction of the reflective mirror MR1, and/or the orientation of the deflection surface of the optical axis switching member SW, based on the pupil positions of both eyes identified in step S21.

In some embodiments, the main controller 211a can perform refractometry as if both eyes were looking at the fixation target by switching the optical axis at high speed using the optical axis switching member SW. In this case, the main controller 211a acquires a plurality of ring images based on the returning light of the measurement pattern light flux of the left and right eyes when the optical axis is switched, and analyzes the images on which the acquired ring images are superimposed to calculate the refractive power value(s).

In some embodiments, a horopter or trial lens may be placed in front of both eyes in the configuration according to the second embodiment.

As explained above, according to the second embodiment, an ophthalmic apparatus capable of measuring characteristics of both eyes with high precision and space saved at low cost can be provided, as in the first embodiment. In particular, it is possible to reduce the size and cost of the optical system of the ophthalmic apparatus capable of performing OCT measurements on both eyes.

Third Embodiment

In the first embodiment, the case has been described in which the fixation projection systems 4L and 4R are provided in the transmission direction of the dichroic mirrors ML and MR. However, the configuration of the ophthalmic apparatus according to the embodiments is not limited thereto. For example, a common optotype (visual target) presenting unit for both eyes may be arranged in the transmission direction of the dichroic mirrors ML and MR.

In the following, the ophthalmic apparatus according to the third embodiment will be described focusing on differences from the ophthalmic apparatus 1 according to the first embodiment.

Figure 20:
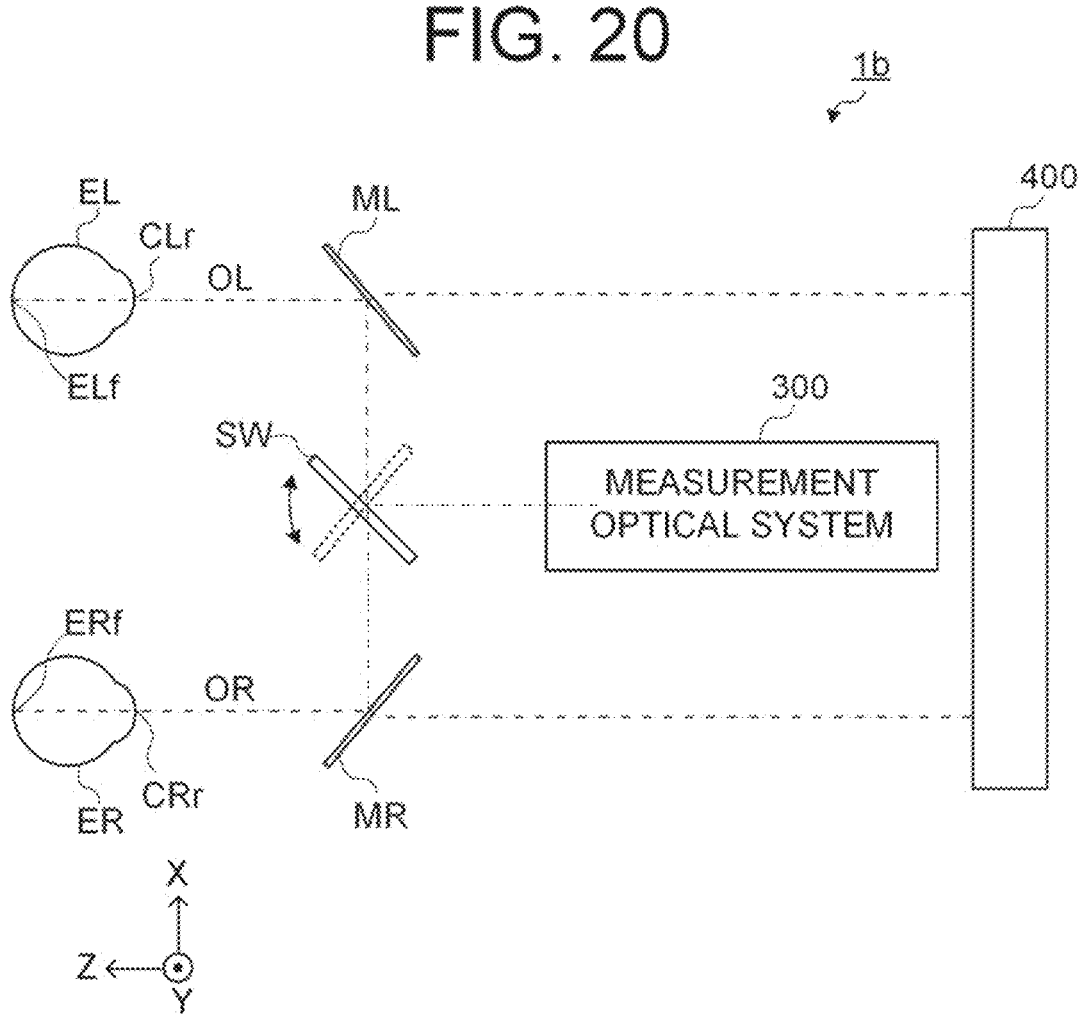
FIG. 20 is a schematic diagram illustrating an example of a configuration of an optical system of the ophthalmic apparatus according to a third embodiment.

FIG. 20 shows an example of a configuration of an optical system of the ophthalmic apparatus according to the third embodiment. FIG. 20 schematically shows the configuration of the optical system of the ophthalmic apparatus according to the third embodiment when viewed from the upper side, as in FIG. 1.

The difference between the configuration of the optical system of the ophthalmic apparatus 1b according to the third embodiment and the configuration of the optical system of the ophthalmic apparatus 1 according to the first embodiment is that an optotype presenting unit 400 is provided in place of the fixation projection systems 4L and 4R.

The optotype presenting unit 400 includes an optotype chart. For example, the optotype chart is a transmissive type optotype chart that is placed between the light source for illumination and the subject's eye and represents the fixation target(s). In some embodiments, the optotype chart is a transparent film on which the optotype is printed. Examples of the fixation target include landscape chart and dot optotype (visual target).

The controller turns the light source for illumination on to illuminate the optotype chart with light from the light source for illumination, when the refractometry is performed. The light transmitted through the optotype chart is transmitted through the dichroic mirrors ML and MR as the fixation light, and is projected onto the subject's left eye EL and the subject's right eye ER.

The dichroic mirror ML is an example of the "first optical path coupling member" according to the embodiments. The dichroic mirror MR is an example of the "second optical path coupling member" according to the embodiments.

Figure 21:
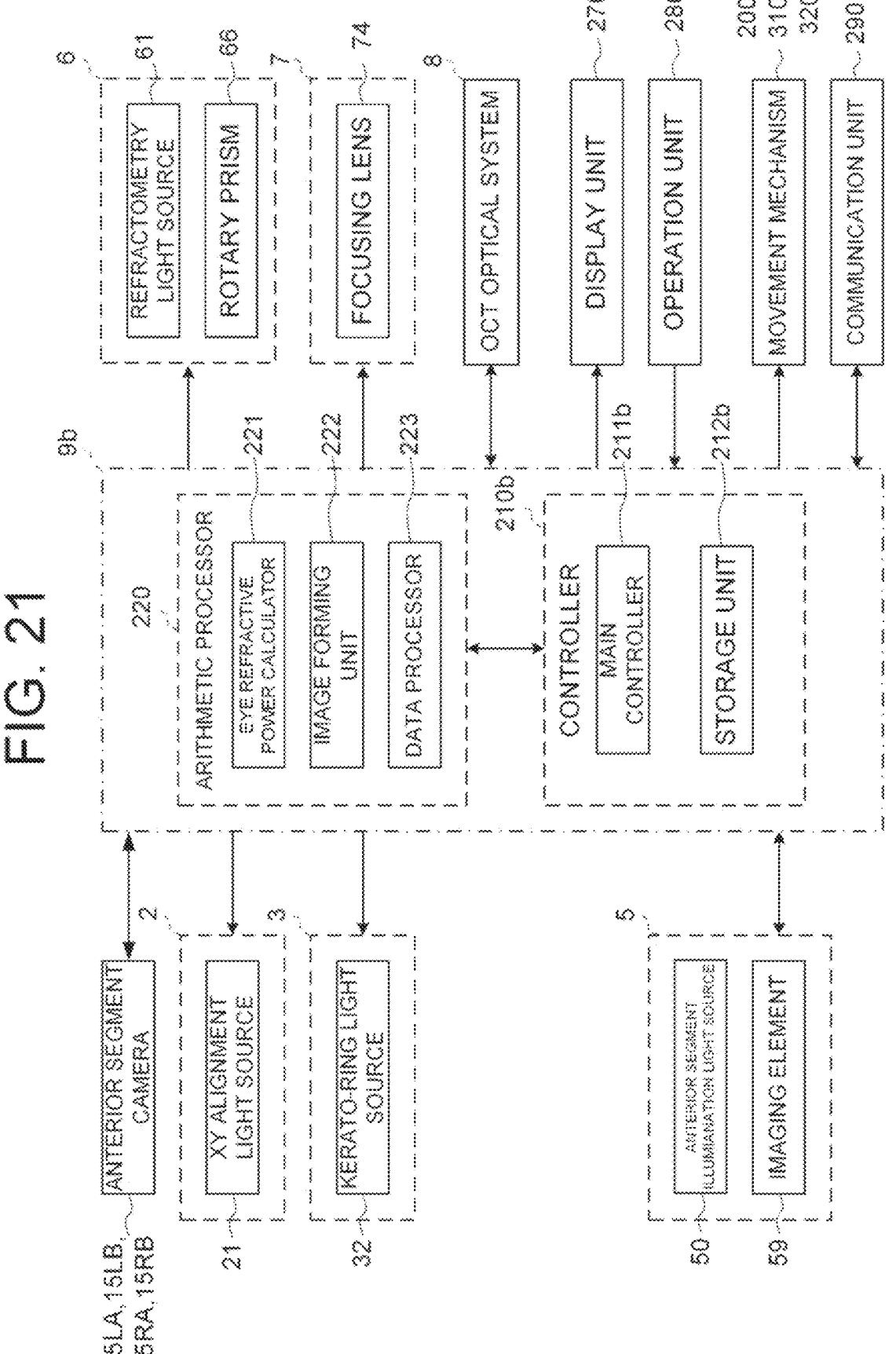
FIG. 21 is a schematic diagram illustrating an example of a configuration of a processing system of the ophthalmic apparatus according to the third embodiment.

FIG. 21 shows an example of a configuration of a processing system of the ophthalmic apparatus 1b according to the third embodiment. FIG. 21 shows an example of a functional block diagram illustrating the processing system of the ophthalmic apparatus 1b. In FIG. 21, like reference numerals designate like parts as in FIG. 10 or FIG. 20. The same description may not be repeated.

The difference between the configuration of the processing system of the ophthalmic apparatus 1b and the configuration of the processing system of the ophthalmic apparatus 1 shown in FIG. 10 is that the fixation projection systems 4L and 4R are omitted, and that a processor 9b is provided in place of the processor 9.

The difference between the configuration of the processor 9b and the configuration of the processor 9 shown in FIG. 10 is that a controller 210b is provided in place of the controller 210. The controller 210b includes a main controller 211b and a storage unit 212b. The main controller 211b can perform the same control as the main controller 211, except that the control for the fixation projection systems 4L and 4R by the main controller 211 is omitted. The storage unit 212b stores the same programs as the storage unit 212, except the program using for controlling the fixation projection systems 4L and 4R.

The operation of the ophthalmic apparatus 1b according to the third embodiment is almost the same as that of the ophthalmic apparatus 1 according to the first embodiment shown in FIG. 12 and FIG. 13, except that the control for the fixation projection systems 4L and 4R is omitted.

In the third embodiment, the same fixation target is presented to both eyes in the refractometry, the keratometry, and the OCT measurement. In other words, the refractometry can be performed on one eye at a time in sequence in a state where the same fixation target is presented to both eyes with both eyes open. In addition, the OCT measurement can be performed on one eye at a time in sequence in a state where the same fixation target is presented to both eyes with both eyes open.

In some embodiments, the optotype presenting unit 400 presents the optotype by the operation of the examiner. In some embodiments, the optotype presenting unit 400 presents the optotype under the control from the main controller 211b. In this case, the main controller 211b controls the optotype presenting unit 400 in the same way as the control for the fixation projection system 4 according to the second embodiment.

In some embodiments, a horopter or trial lens may be placed in front of both eyes in the configuration according to the third embodiment.

As explained above, according to the third embodiment, an ophthalmic apparatus capable of measuring characteristics of both eyes with high precision and space saved at low cost can be provided, as in the first embodiment. In particular, it is possible to reduce the size and cost of the optical system of the ophthalmic apparatus capable of performing OCT measurements on both eyes.

[Actions]

The ophthalmic apparatus according to the embodiments will be described.

The first aspect of the embodiments is an ophthalmic apparatus (1, 1a, 1b) including an objective lens (51), an OCT optical system (8), an optical axis switching member (SW), a controller (210, 210a, 210b, main controller 211, 211a, 211b), an intraocular parameter calculator (data processor 223). The OCT optical system is configured to split light (L0) from a light source (light source unit 101) into measurement light (LS) and reference light (LR), to project the measurement light onto a subject's left eye (EL) or a subject's right eye (ER) via the objective lens, the subject's left eye being arranged on a first measurement optical axis (measurement optical axis OL), the subject's right eye being arranged on a second measurement optical axis (measurement optical axis OR), and to detect interference light (LC) between returning light of the measurement light from the subject's left eye or the subject's right eye and the reference light having traveled through a reference optical path. The optical axis switching member is configured to switch an optical axis of the OCT optical system so that the optical axis of the OCT optical system approximately coincides with any one of the first measurement optical axis and the second measurement optical axis. The controller is configured to control the optical axis switching member. The intraocular parameter calculator is configured to calculate an intraocular parameter (for example, axial length) of the subject's left eye based on a detection result of the interference light acquired in a state where the optical axis of the OCT optical system is switched so that the optical axis of the OCT optical system approximately coincides with the first measurement optical axis, and to calculate an intraocular parameter (for example, axial length) of the subject's right eye based on a detection result of the interference light acquired in a state where the optical axis of the OCT optical system is switched so that the optical axis of the OCT optical system approximately coincides with the second measurement optical axis.

According to such an aspect, the OCT measurement can be performed on both eyes with both eyes open, using a single OCT optical system. Thereby, an ophthalmic apparatus capable of measuring characteristics of both eyes with high precision and space saved at low cost can be provided.

In the second aspect of the embodiments, in the first embodiment, before performing OCT measurement using the measurement light on one of the subject's left eye and the subject's right eye, the controller is configured to control the OCT optical system to adjust an optical path length of the reference optical path based on an axial length and a refractive power of another of the subject's left eye and the subject's right eye.

According to such an aspect, before performing OCT measurement on one of subject's left eye and the subject's right eye, the measurement environment estimated from the measurement environment of another of subject's left eye and the subject's right eye can be set, and the time required for OCT measurement can be shortened.

In the third aspect of the embodiments, in the first aspect or the second aspect, the optical axis switching member deflects an optical path of the measurement light. The ophthalmic apparatus according the present aspect further includes: a first fixation optical system (fixation projection system 4L) configured to project a first fixation light flux onto the subject's left eye; a first optical path coupling member (dichroic mirror ML) configured to optically couple the optical path of the measurement light deflected by the optical axis switching member with an optical path of the first fixation light flux; a second fixation optical system (fixation projection system 4R) configured to project a second fixation light flux onto the subject's right eye; and a second optical path coupling member (dichroic mirror MR) configured to optically couple the optical path of the measurement light deflected by the optical axis switching member with an optical path of the second fixation light flux.

According to such an aspect, the OCT measurement can be performed with both eyes open while independently presenting the fixation target to subject's left eye and the subject's right eye, respectively, with a simple configuration.

In the fourth aspect of the embodiments, in the first aspect or the second aspect, the optical axis switching member deflects an optical path of the measurement light. The ophthalmic apparatus according to the present aspect further includes: a fixation optical system (4) configured to project a fixation light flux onto any one of the subject's left eye and the subject's right eye; an optical path coupling member (dichroic mirror 83) configured to optically couple an optical path of the fixation light flux with an optical path of the measurement light, and to guide the fixation light flux to the objective lens; a first reflection member (reflective mirror ML1) configured to deflect the optical path of the measurement light deflected by the optical axis switching member toward the subject's left eye; a second reflection member (reflective mirror MR1) configured to deflect the optical path of the measurement light deflected by the optical axis switching member toward the subject's right eye.

According to such an aspect, the OCT measurements can be performed with both eyes open while presenting the same fixation target to both eyes using a common fixation projection system for both eyes.

In the fifth aspect of the embodiments, in the first aspect or the second aspect, the optical axis switching member deflects an optical path of the measurement light. The ophthalmic apparatus according to the present aspect further includes: a first optical path coupling member (dichroic mirror ML) configured to deflect the optical path of the measurement light deflected by the optical axis switching member toward the subject's left eye, and to transmit a first fixation light flux from a transmission direction to guide the first fixation light flux to the subject's left eye; a second optical path coupling member (dichroic mirror MR) configured to deflect the optical path of the measurement light deflected by the optical axis switching member toward the subject's right eye, and to transmit a second fixation light flux from a transmission direction to guide the second fixation light flux to the subject's right eye.

According to such an aspect, a common fixation projection system for both eyes can be located outside of the apparatus, and the OCT measurement can be performed with both eyes open while presenting the same fixation target to both eyes.

In the sixth aspect of the embodiments, the ophthalmic apparatus, in the third aspect or the fifth aspect, further includes a first adjustment unit (angle of convergence adjusting unit, movement mechanism for rotating the dichroic mirrors ML and MR) configured to change an orientation of the first measurement optical axis and an orientation of the second measurement optical axis, by changing an orientation of an optical path coupling plane of the first optical path coupling member and an orientation of an optical path coupling plane of the second optical path coupling member.

According to such an aspect, the OCT measurement can be performed with both eyes open while adjusting the angle of convergence, with a simple configuration.

In the seventh aspect of the embodiments, the ophthalmic apparatus, in the third aspect, the fifth aspect, or the sixth aspect, further includes a second adjustment unit (height adjusting unit, movement mechanism for rotating the deflection surface of the optical axis switching member SW, the deflection surface (optical path coupling plane) of the dichroic mirror ML, and the deflection surface of the dichroic mirror MR) configured to change an arrangement direction of the first measurement optical axis and the second measurement optical axis, by changing a deflection direction of the optical axis switching member, an orientation of an optical path coupling plane of the first optical path coupling member, and an orientation of an optical path coupling plane of the second optical path coupling member.

According to such an aspect, when the arrangement direction of the first measurement optical axis and the second measurement optical axis is not parallel to the arrangement direction of the subject's left eye and the subject's right eye, the arrangement direction of the first measurement optical axis and the second measurement optical axis can be aligned in the arrangement direction of the subject's left eye and the subject's right eye with a simple configuration.

In the eighth aspect of the embodiments, the ophthalmic apparatus, in the fourth aspect, further includes a first adjustment unit (angle of convergence adjusting unit, movement mechanism for rotating the reflective mirrors ML1 and MR1) configured to change an orientation of the first measurement optical axis and an orientation of the second measurement optical axis, by changing an orientation of a reflective surface of the first reflection member and an orientation of a reflective surface of the second reflection member.

According to such an aspect, the OCT measurement can be performed with both eyes open while adjusting the angle of convergence, with a simple configuration.

In the ninth aspect of the embodiments, the ophthalmic apparatus, in the fourth aspect or the eighth aspect, further includes a second adjustment unit (height adjusting unit, movement mechanism for rotating the deflection surface of the optical axis switching member SW, the deflection surface of the dichroic mirror ML1, and the deflection surface of the dichroic mirror MR1) configured to change an arrangement direction of the first measurement optical axis and the second measurement optical axis, by changing a deflection direction of the optical axis switching member, an orientation of a reflective surface of the first reflection member, and an orientation of a reflective surface of the second reflection member.

According to such an aspect, when the arrangement direction of the first measurement optical axis and the second measurement optical axis is not parallel to the arrangement direction of the subject's left eye and the subject's right eye, the arrangement direction of the first measurement optical axis and the second measurement optical axis can be aligned in the arrangement direction of the subject's left eye and the subject's right eye with a simple configuration.

In the tenth aspect of the embodiments, the ophthalmic apparatus, in any one of the third aspect to the ninth aspect, further includes a third adjustment unit (pupillary distance adjusting unit, movement mechanism 310) configured to change a distance between the first measurement optical axis and the second measurement optical axis, by moving the optical axis switching member along the first measurement optical axis or the second measurement optical axis.

According to such an aspect, the first measurement optical axis and the second measurement optical axis can be aligned with the pupillary distance of the subject with a simple configuration.

In the eleventh aspect of the embodiments, the ophthalmic apparatus, in any one of the first aspect to the tenth aspect, further includes: two or more imaging units (anterior segment cameras 15LA, 15LB, 15RA, and 15RB) configured to photograph an anterior segment of the subject's left eye and an anterior segment of the subject's right eye from different directions each other; and a movement mechanism (200) configured to move at least the OCT optical system three-dimensionally. The controller is configured to change a relative position of the OCT optical system relative to the subject's left eye and the subject's right eye, and to change an orientation of the first measurement optical axis, an orientation of the second measurement optical axis, and a distance between the first measurement optical axis and the second measurement optical axis so that the first measurement optical axis coincides with a visual axis of the subject's left eye and the second measurement optical axis coincides with a visual axis of the subject's right eye, based on two or more images obtained by the two or more imaging units.

According to such an aspect, the position matching of the ophthalmic apparatus capable of performing OCT measurement on both eyes with both eyes open can be performed with a simple configuration and a wide dynamic range.

In the twelfth aspect of the embodiments, in the eleventh aspect, the two or more imaging units includes: a first imaging unit (anterior segment camera 15LA) configured to photograph the anterior segment of the subject's left eye; a second imaging unit (anterior segment camera 15LR) configured to photograph the anterior segment of the subject's left eye and the anterior segment of the subject's right eye; and a third imaging unit (anterior segment camera 15RA) configured to the anterior segment of the subject's right eye.

According to such an aspect, the number of anterior segment cameras can be reduced, and the OCT measurement can be performed on both eyes with both eyes open at a lower cost.

In the thirteenth aspect of the embodiments, the ophthalmic apparatus, in any one of the first aspect to the twelfth aspect, further includes a refractive power measurement optical system (refractometry projection system 6, and refractometry light reception system 7) and an eye refractive power calculator (221). The refractive power measurement optical system is configured to project a first measurement pattern light flux along the first measurement optical axis onto the subject's left eye via the objective lens, to project a second measurement pattern light flux along the second measurement optical axis onto the subject's right eye via the objective lens, and to detect returning light of the first measurement pattern light flux from the subject's left eye and returning light of the second measurement pattern light flux from the subject's right eye. The eye refractive power calculator is configured to a refractive power of the subject's left eye based on a light receiving result of the returning light of the first measurement pattern light flux and a refractive power of the subject's right eye based on a light receiving result of the returning light of the second measurement pattern light flux.

According to such an aspect, the refractometry can be performed on both eyes with both eyes open.

In the fourteenth aspect of the embodiments, in the thirteenth aspect, the refractive power measurement optical system is configured to project the first measurement pattern light flux and the second measurement pattern light flux so that a focal position is at a position corresponding to an intermediate power between the refractive power of the subject's left eye and the refractive power of the subject's right eye.

According to such an aspect, the refractometry can be performed on both eyes, even when the refractive powers of both eyes are different.

<Others>

The above-described embodiments are merely examples for carrying out the present invention. Those who intend to implement the present invention can apply any modification, omission, addition, or the like within the scope of the gist of the present invention.

Further, in the embodiments described above, the case has been described in which the ophthalmic apparatus performs OCT on the fundus. However, the configuration of the ophthalmic apparatus according to the embodiments is not limited thereto. For example, the present invention can be applied to ophthalmic apparatuses that perform OCT on the fundus and the anterior segment.

Further, in the embodiments described above, the case has been described in which the optical axis switching member SW turns back the optical axis in XZ plane. However, the configuration of the ophthalmic apparatus according to the embodiments is not limited thereto. For example, the optical axis switching member SW may be configured to turn back the optical axis in the Y direction (up direction or down direction to the subject). In this case, the pupillary distance adjusting unit can adjust the pupillary distance by moving or rotating the dichroic mirrors ML and MR.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
an objective lens;
an Optical Coherence Tomography (OCT) optical system configured to split light from a light source into measurement light and reference light, to project the measurement light onto a subject's left eye or a subject's right eye via the objective lens, the subject's left eye being arranged on a first measurement optical axis, the subject's right eye being arranged on a second measurement optical axis, and to detect interference light between returning light of the measurement light from the subject's left eye or the subject's right eye and the reference light having traveled through a reference optical path;

an optical axis switching member including a movable optical deflection surface and configured to switch an optical axis of the OCT optical system so that the optical axis of the OCT optical system approximately coincides with any one of the first measurement optical axis and the second measurement optical axis;

processing circuitry configured as a controller configured to control the optical axis switching member; and the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis, wherein before performing OCT measurement using the measurement light on one of the subject's left eye and the subject's right eye, the controller is configured to control the OCT optical system to adjust an optical path length of the reference optical path based on an axial length and a refractive power of another of the subject's left eye and the subject's right eye.

2. The ophthalmic apparatus of claim 1, wherein the optical axis switching member is configured to deflect an optical path of the measurement light, and the ophthalmic apparatus further includes:

a first fixation optical system including a first lens and configured to project a first fixation light flux onto the subject's left eye;

a first optical path coupling member including a first dichroic mirror and configured to optically couple the optical path of the measurement light deflected by the optical axis switching member with an optical path of the first fixation light flux;

a second fixation optical system including a second lens and configured to project a second fixation light flux onto the subject's right eye; and a second optical path coupling member including a second dichroic mirror and configured to optically couple the optical path of the measurement light deflected by the optical axis switching member with an optical path of the second fixation light flux.

3. The ophthalmic apparatus of claim 2, wherein the processing circuitry is further configured as a first adjustment unit configured to change an orientation of the first measurement optical axis and an orientation of the second measurement optical axis, by changing an orientation of an optical path coupling plane of the first optical path coupling member and an orientation of an optical path coupling plane of the second optical path coupling member.

4. The ophthalmic apparatus of claim 1, wherein
the optical axis switching member is configured to deflect an optical path of the measurement light, and
the ophthalmic apparatus further includes:
a fixation optical system including a first lens and configured to project a fixation light flux onto any one of the subject's left eye and the subject's right eye;
an optical path coupling member including a first dichroic mirror and configured to optically couple an optical path of the fixation light flux with an optical path of the measurement light, and to guide the fixation light flux to the objective lens;
a first reflection member including a first reflective mirror and configured to deflect the optical path of the measurement light deflected by the optical axis switching member toward the subject's left eye; and
a second reflection member including a second reflective mirror and configured to deflect the optical path of the measurement light deflected by the optical axis switching member toward the subject's right eye.

5. The ophthalmic apparatus of claim 4, wherein
the processing circuitry is further configured as a first adjustment unit configured to change an orientation of the first measurement optical axis and an orientation of the second measurement optical axis, by changing an orientation of a reflective surface of the first reflection member and an orientation of a reflective surface of the second reflection member.

6. The ophthalmic apparatus of claim 4, wherein
the processing circuitry is further configured as a third adjustment unit configured to change a distance between the first measurement optical axis and the second measurement optical axis, by moving the optical axis switching member along the first measurement optical axis or the second measurement optical axis.

7. The ophthalmic apparatus of claim 1, wherein
the optical axis switching member is configured to deflect an optical path of the measurement light, and
the ophthalmic apparatus further includes:
a first optical path coupling member including a first dichroic mirror and configured to deflect the optical path of the measurement light deflected by the optical axis switching member toward the subject's left eye, and to transmit a first fixation light flux from a transmission direction to guide the first fixation light flux to the subject's left eye; and
a second optical path coupling member including a second dichroic mirror and configured to deflect the optical path of the measurement light deflected by the optical axis switching member toward the subject's right eye, and to transmit a second fixation light flux from a transmission direction to guide the second fixation light flux to the subject's right eye.

8. The ophthalmic apparatus of claim 7, wherein
the processing circuitry is further configured as a first adjustment unit configured to change an orientation of the first measurement optical axis and an orientation of the second measurement optical axis, by changing an orientation of an optical path coupling plane of the first optical path coupling member and an orientation of an optical path coupling plane of the second optical path coupling member.

9. The ophthalmic apparatus of claim 7, wherein
the processing circuitry is further configured as a third adjustment unit configured to change a distance between the first measurement optical axis and the second measurement optical axis, by moving the optical axis switching member along the first measurement optical axis or the second measurement optical axis.

10. The ophthalmic apparatus of claim 1, further comprising
two or more imaging units configured to photograph an anterior segment of the subject's left eye and an anterior segment of the subject's right eye from different directions each other; and
a movement mechanism including an actuator and configured to move at least the OCT optical system three-dimensionally, wherein
the controller is configured to change a relative position of the OCT optical system relative to the subject's left eye and the subject's right eye, and to change an orientation of the first measurement optical axis, an orientation of the second measurement optical axis, and a distance between the first measurement optical axis and the second measurement optical axis so that the first measurement optical axis coincides with a visual axis of the subject's left eye and the second measurement optical axis coincides with a visual axis of the subject's right eye, based on two or more images obtained by the two or more imaging units.

11. The ophthalmic apparatus of claim 10, wherein
the two or more imaging units includes:
a first imaging unit including a first camera and configured to photograph the anterior segment of the subject's left eye;
a second imaging unit including a second camera and configured to photograph the anterior segment of the subject's left eye and the anterior segment of the subject's right eye; and
a third imaging unit including a third camera and configured to the anterior segment of the subject's right eye.

12. An ophthalmic apparatus, comprising:
an objective lens:
an Optical Coherence Tomography (OCT) optical system configured to split light from a light source into measurement light and reference light, to project the measurement light onto a subject's left eye or a subject's right eye via the objective lens, the subject's left eye being arranged on a first measurement optical axis, the subject's right eye being arranged on a second measurement optical axis, and to detect interference light between returning light of the measurement light from the subject's left eye or the subject's right eye and the reference light having traveled through a reference optical path;
an optical axis switching member including a movable optical deflection surface and configured to switch an optical axis of the OCT optical system so that the optical axis of the OCT optical system approximately coincides with any one of the first measurement optical axis and the second measurement optical axis;
processing circuitry configured as a controller configured to control the optical axis switching member; and
the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis,
wherein
the optical axis switching member is configured to deflect an optical path of the measurement light,
the ophthalmic apparatus further includes:
a first fixation optical system including a first lens and configured to project a first fixation light flux onto the subject's left eve;
a first optical path coupling member including a first dichroic mirror and configured to optically couple the optical path of the measurement light deflected by the optical axis switching member with an optical path of the first fixation light flux;
a second fixation optical system including a second lens and configured to project a second fixation light flux onto the subject's right eye; and
a second optical path coupling member including a second dichroic mirror and configured to optically couple the optical path of the measurement light deflected by the optical axis switching member with an optical path of the second fixation light flux, and
the processing circuitry is further configured as a second adjustment unit configured to change an arrangement direction of the first measurement optical axis and the second measurement optical axis, by changing a deflection direction of the optical axis switching member, an orientation of an optical path coupling plane of the first optical path coupling member, and an orientation of an optical path coupling plane of the second optical path coupling member.

13. An ophthalmic apparatus, comprising:
an objective lens;
an Optical Coherence Tomography (OCT) optical system configured to split light from a light source into measurement light and reference light, to project the measurement light onto a subject's left eye or a subject's right eye via the objective lens, the subject's left eye being arranged on a first measurement optical axis, the subject's right eye being arranged on a second measurement optical axis, and to detect interference light between returning light of the measurement light from the subject's left eye or the subject's right eye and the reference light having traveled through a reference optical path;
an optical axis switching member including a movable optical deflection surface and configured to switch an optical axis of the OCT optical system so that the optical axis of the OCT optical system approximately coincides with any one of the first measurement optical axis and the second measurement optical axis;
processing circuitry configured as a controller configured to control the optical axis switching member; and
the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis,
wherein
the optical axis switching member is configured to deflect an optical path of the measurement light,
the ophthalmic apparatus further includes:
a first optical path coupling member including a first dichroic mirror and configured to deflect the optical path of the measurement light deflected by the optical axis switching member toward the subject's left eye, and to transmit a first fixation light flux from a transmission direction to guide the first fixation light flux to the subject's left eye; and
a second optical path coupling member including a second dichroic mirror and configured to deflect the optical path of the measurement light deflected by the optical axis switching member toward the subject's right eye, and to transmit a second fixation light flux from a transmission direction to guide the second fixation light flux to the subject's right eye, and
the processing circuitry is further configured as a second adjustment unit configured to change an arrangement direction of the first measurement optical axis and the second measurement optical axis, by changing a deflection direction of the optical axis switching member, an orientation of an optical path coupling plane of the first optical path coupling member, and an orientation of an optical path coupling plane of the second optical path coupling member.

14. An ophthalmic apparatus, comprising:
an objective lens;
an Optical Coherence Tomography (OCT) optical system configured to split light from a light source into measurement light and reference light, to project the measurement light onto a subject's left eye or a subject's right eve via the objective lens, the subject's left eve being arranged on a first measurement optical axis, the subject's right eye being arranged on a second measurement optical axis, and to detect interference light between returning light of the measurement light from the subject's left eye or the subject's right eye and the reference light having traveled through a reference optical path;
an optical axis switching member including a movable optical deflection surface and configured to switch an optical axis of the OCT optical system so that the optical axis of the OCT optical system approximately coincides with any one of the first measurement optical axis and the second measurement optical axis;
processing circuitry configured as a controller configured to control the optical axis switching member; and
the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis, wherein the optical axis switching member is configured to deflect an optical path of the measurement light, the ophthalmic apparatus further includes:

a fixation optical system including a first lens and configured to project a fixation light flux onto any one of the subject's left eye and the subject's right eye:

an optical path coupling member including a first dichroic mirror and configured to optically couple an optical path of the fixation light flux with an optical path of the measurement light, and to guide the fixation light flux to the objective lens;

a first reflection member including a first reflective mirror and configured to deflect the optical path of the measurement light deflected by the optical axis switching member toward the subject's left eye; and a second reflection member including a second reflective mirror and configured to deflect the optical path of the measurement light deflected by the optical axis switching member toward the subject's right eye, and the processing circuitry is further configured as a second adjustment unit configured to change an arrangement direction of the first measurement optical axis and the second measurement optical axis, by changing a deflection direction of the optical axis switching member, an orientation of a reflective surface of the first reflection member, and an orientation of a reflective surface of the second reflection member.

15. An ophthalmic apparatus, comprising:

an objective lens;

an Optical Coherence Tomography (OCT) optical system configured to split light from a light source into measurement light and reference light, to project the measurement light onto a subject's left eye or a subject's right eye via the objective lens, the subject's left eye being arranged on a first measurement optical axis, the subject's right eve being arranged on a second measurement optical axis, and to detect interference light between returning light of the measurement light from the subject's left eye or the subject's right eye and the reference light having traveled through a reference optical path;

an optical axis switching member including a movable optical deflection surface and configured to switch an optical axis of the OCT optical system so that the optical axis of the OCT optical system approximately coincides with any one of the first measurement optical axis and the second measurement optical axis;

processing circuitry configured as a controller configured to control the optical axis switching member; and the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis,

wherein the optical axis switching member is configured to deflect an optical path of the measurement light, the ophthalmic apparatus further includes:

a first fixation optical system including a first lens and configured to project a first fixation light flux onto the subject's left eve;

a first optical path coupling member including a first dichroic mirror and configured to optically couple the optical path of the measurement light deflected by the optical axis switching member with an optical path of the first fixation light flux;

a second fixation optical system including a second lens and configured to project a second fixation light flux onto the subject's right eye; and a second optical path coupling member including a second dichroic mirror and configured to optically couple the optical path of the measurement light deflected by the optical axis switching member with an optical path of the second fixation light flux, and the processing circuitry is further configured as a third adjustment unit configured to change a distance between the first measurement optical axis and the second measurement optical axis, by moving the optical axis switching member along the first measurement optical axis or the second measurement optical axis.

16. An ophthalmic apparatus, comprising:

an objective lens;

an Optical Coherence Tomography (OCT) optical system configured to split light from a light source into measurement light and reference light, to project the measurement light onto a subject's left eye or a subject's right eve via the objective lens, the subject's left eve being arranged on a first measurement optical axis, the subject's right eye being arranged on a second measurement optical axis, and to detect interference light between returning light of the measurement light from the subject's left eye or the subject's right eye and the reference light having traveled through a reference optical path:

an optical axis switching member including a movable optical deflection surface and configured to switch an optical axis of the OCT optical system so that the optical axis of the OCT optical system approximately coincides with any one of the first measurement optical axis and the second measurement optical axis;

processing circuitry configured as a controller configured to control the optical axis switching member;

the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis;

a refractive power measurement optical system including a light projector and configured to project a first measurement pattern light flux along the first measurement optical axis onto the subject's left eye via the objective lens, to project a second measurement pattern light flux along the second measurement optical axis onto the subject's right eye via the objective lens, and to detect returning light of the first measurement pattern light flux from the subject's left eye and returning light of the second measurement pattern light flux from the subject's right eye; and the processing circuitry further configured as an eye refractive power calculator configured to a refractive power of the subject's left eye based on a light receiving result of the returning light of the first measurement pattern light flux and a refractive power of the subject's right eye based on a light receiving result of the returning light of the second measurement pattern light flux.

17. The ophthalmic apparatus of claim 16, wherein the processing circuitry is further configured as the refractive power measurement optical system is configured to project the first measurement pattern light flux and the second measurement pattern light flux so that a focal position is at a position corresponding to an intermediate power between the refractive power of the subject's left eye and the refractive power of the subject's right eye.

18. An ophthalmic apparatus, comprising:

an objective lens;

an Optical Coherence Tomography (OCT) optical system configured to split light from a light source into measurement light and reference light, to project the measurement light onto a subject's left eye or a subject's right eye via the objective lens, the subject's left eye being arranged on a first measurement optical axis, the subject's right eye being arranged on a second measurement optical axis, and to detect interference light between returning light of the measurement light from the subject's left eye or the subject's right eye and the reference light having traveled through a reference optical path;

an optical axis switching member including a movable optical deflection surface and configured to switch an optical axis of the OCT optical system so that the optical axis of the OCT optical system approximately coincides with any one of the first measurement optical axis and the second measurement optical axis;

processing circuitry configured as a controller configured to control the optical axis switching member; and the processing circuitry further configured as an intraocular parameter calculator configured to calculate an intraocular parameter of the subject's left eye based on a detection result of the interference light acquired in a state where the optical axis of the OCT optical system is switched so that the optical axis of the OCT optical system approximately coincides with the first measurement optical axis, and to calculate an intraocular parameter of the subject's right eye based on a detection result of the interference light acquired in a state where the optical axis of the OCT optical system is switched so that the optical axis of the OCT optical system approximately coincides with the second measurement optical axis, wherein the processing circuitry is further configured as a first adjustment unit configured to change an orientation of the first measurement optical axis and an orientation of the second measurement optical axis, by changing an orientation of an optical path coupling plane of the first optical path coupling member and an orientation of an optical path coupling plane of the second optical path coupling member, and the processing circuitry is further configured as a second adjustment unit configured to change an arrangement direction of the first measurement optical axis and the second measurement optical axis, by changing a deflection direction of the optical axis switching member, an orientation of an optical path coupling plane of the first optical path coupling member, and an orientation of an optical path coupling plane of the second optical path coupling member.

* * * * *